US010160795B2

(12) United States Patent
Sullivan et al.

(10) Patent No.: US 10,160,795 B2
(45) Date of Patent: Dec. 25, 2018

(54) NEUTRALIZING ANTIBODIES TO EBOLA VIRUS GLYCOPROTEIN AND THEIR USE

(71) Applicants: The United States of America, as represented by the Secretary, Department of Health and Human Services, Washington, DC (US); Institute for Research in Biomedicine, Bellinzona (CH); The United States of America as represented by the Secretary of the Army, Washington, DC (US); Humabs BioMed SA, Bellinzona (CH)

(72) Inventors: Nancy Sullivan, Bethesda, MD (US); Sabue Mulangu, Bethesda, MD (US); Davide Corti, Bellinzona (CH); Antonio Lanzavecchia, Bellinzona (CH); Barney Graham, Bethesda, MD (US); Jean-Jacques Muyembe-Tamfun, Kinshasa (CD); John Trefry, Frederick, MD (US); Julie Ledgerwood, Bethesda, MD (US); Daphne Stanley, Bethesda, MD (US)

(73) Assignees: The United States of America, as represented by the Secretary, Department of Health and Human Services, Washington, DC (US); Institute for Research in Biomedicine, Bellinzona (CH); The United States of America as represented by the Secretary of the Army, Washington, DC (US); Humabs BioMed SA, Bellinzona (CH)

( * ) Notice: Subject to any disclaimer, the term of this patent is extended or adjusted under 35 U.S.C. 154(b) by 25 days.

(21) Appl. No.: 15/526,661

(22) PCT Filed: Nov. 13, 2015

(86) PCT No.: PCT/US2015/060733

§ 371 (c)(1),
(2) Date: May 12, 2017

(87) PCT Pub. No.: WO2016/077789

PCT Pub. Date: May 19, 2016

(65) Prior Publication Data

US 2018/0291088 A1 Oct. 11, 2018

Related U.S. Application Data

(60) Provisional application No. 62/087,087, filed on Dec. 3, 2014, provisional application No. 62/080,094, filed on Nov. 14, 2014.

(51) Int. Cl.

| | |
|---|---|
| *C07K 16/10* | (2006.01) |
| *A61K 39/00* | (2006.01) |
| *A61K 39/395* | (2006.01) |
| *A61K 45/06* | (2006.01) |
| *C07K 16/00* | (2006.01) |
| *G01N 33/569* | (2006.01) |

(52) U.S. Cl.

CPC ....... *C07K 16/10* (2013.01); *G01N 33/56983* (2013.01); *A61K 2039/505* (2013.01); *C07K 2317/52* (2013.01); *C07K 2317/56* (2013.01); *C07K 2317/565* (2013.01); *C07K 2317/567* (2013.01); *C07K 2317/72* (2013.01); *C07K 2317/732* (2013.01); *C07K 2317/76* (2013.01); *G01N 2333/08* (2013.01); *G01N 2800/26* (2013.01)

(58) Field of Classification Search

CPC .............. A61K 2039/505; A61K 45/06; C07K 2317/565; C07K 2317/56; C07K 2317/34

See application file for complete search history.

(56) References Cited

U.S. PATENT DOCUMENTS

| | | | |
|---|---|---|---|
| 6,875,433 | B2 | 4/2005 | Hart et al. |
| 8,513,391 | B2 | 8/2013 | Jones et al. |
| 9,097,713 | B2 | 8/2015 | Dye et al. |

FOREIGN PATENT DOCUMENTS

| | | |
|---|---|---|
| WO | WO 2004/018649 | 3/2004 |
| WO | WO 2011/071574 | 6/2011 |
| WO | WO 2016/075546 | 5/2016 |

OTHER PUBLICATIONS

International Search Report and Written Opinion for PCT/IB2015/0023432, mailed by the European Patent Office acting as International Searching Authority dated Feb. 23, 2016 (13 pages).

Lee, et al. "Neutralizing ebolavirus: structural insights into the envelope glycoprotein and antibodies targeted against it." *Current Opinion in Structural Biology* 19, No. 4 (2009): 408-417.

Qiu, et al. "Characterization of Zaire ebolavirus glycoprotein-specific monoclonal antibodies." *Clinical Immunology* 141, No. 2 (2011): 218-227.

Qiu, et al. "Successful treatment of Ebola virus-infected cynomoigus macaques with monoclonal antibodies." *Science Translational Medicine* 4, No. 138 (2012): 138ra81-138ra81.

*Primary Examiner* — Barry A Chestnut

(74) *Attorney, Agent, or Firm* — Klarquist Sparkman, LLP

(57) ABSTRACT

Neutralizing antibodies and antigen binding fragments that specifically bind to Ebola virus glycoprotein are disclosed. Nucleic acids encoding these antibodies, vectors and host cells are also provided. Methods for detecting Ebola virus using the antibodies and antigen binding fragments are disclosed. The antibodies, antigen binding fragments, nucleic acids, and vectors, can be used, for example, to prevent and/or treat Ebola virus infection in a subject.

39 Claims, 33 Drawing Sheets

Specification includes a Sequence Listing.

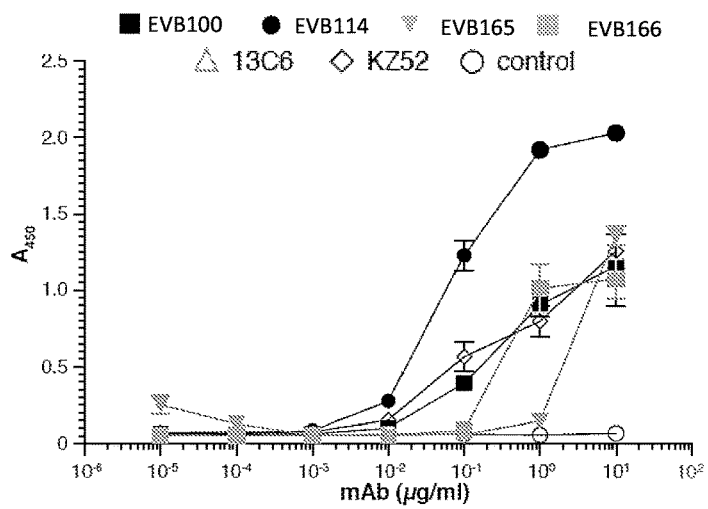
FIG. 2A
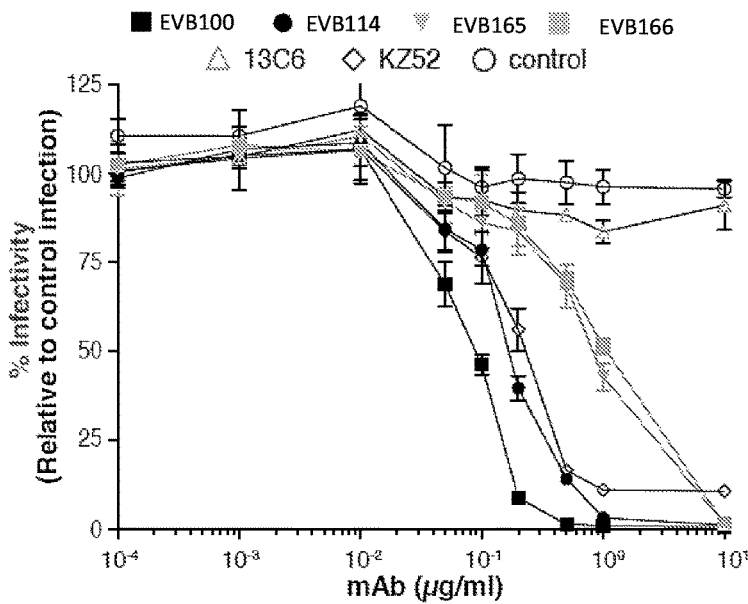
FIG. 2B
FIG. 2C
| | VH | Identity % | D | JH | VL | Identity % | JL | HCDR3 length | IgG subclass |
|---|---|---|---|---|---|---|---|---|---|
| EVB100 | V4-59*01 | 94.74% | D3-16*02 | J4*02 | VL3-1*01 | 92.11% | J2*01 | 19 | IgG3 |
| EVB114 | V3-13*01 | 87.37% | D6-19*01 | J4*02 | VK1-27*01 | 92.83% | J4*01 | 13 | IgG1 |
| EVB165 | V3-7*01 | 89.93% | D2-2*02 | J4*02 | VK1-39*01 | 89.96% | J1*01 | 21 | IgG1 |
| EVB166 | V1-69*04 | 92.01% | D3-22*01 | J6*03 | VK3-20*01 | 97.16% | J3*01 | 16 | IgG3 |

FIG. 2D

```
EVB100 VH UCA   QVQLQESGPGLVKPSETLSLTCTVSGGSISSYYWSWIRQPPGKGLEWIGYIYYSGSTNYNPSLKSRVTIS 70
         gH    ................................................................... 70
      gH-FR    ..........................L..F...............P...............E....M. 70
   gH-FR1-2-4  ..........................L..F...............P.S.............E....M. 70
         sH    .................D........L..F...............P.S..................... 70

EVB100 VH UCA   VDTSKNQFSLKLSSVTAADTAVYYCARASRSYVWGSYRPTAFDYWGQGTLVTVSS 125
         gH    .........................V....Y...S................... 125
      gH-FR    ...TR..I.....D...........V....Y...S................... 125
   gH-FR1-2-4  ...TR..I.....D...........V....Y...S................... 125
         sH    .........................V....Y...S................... 125
```

FIG. 2E

```
EVB100 VL UCA   SYELTQPPSVSVSPGQTASITCSGDKLGDKYACWYQQKPGQSPVLVIYQDSKRPSGIPERFSGSNSGNTA 70
         gL    ....................................N...........N..................... 70
      gL-FR    ........L......IF......N......V..F..R......M.L...N..................... 70
         sL    ........................................................................ 70

EVB100 VL UCA   TLTISGTQAMDEADYYCQAWDSTVVFGGGTKLTVL 105
         gL    .............T..................... 105
      gL-FR    .......ST....T..................... 105
         sL    .............T..................... 105
```

|  | Analyte | | | | |
|---|---|---|---|---|---|
| Competitor | KZ52 | EVB100 | 13c6 | EVB114 | Control |
| KZ52 | 83.4% | 73.1% | 7.9% | -6.1% | NB |
| EVB100 | 85.9% | 92.0% | -2.7% | -4.4% | NB |
| 13c6 | 3.8% | 12.8% | 104.0% | 84.4% | NB |
| EVB114 | 14.8% | 8.1% | 102.5% | 97.4% | NB |
| Control | 28.1% | 5.2% | -5.0% | -10.8% | NB |

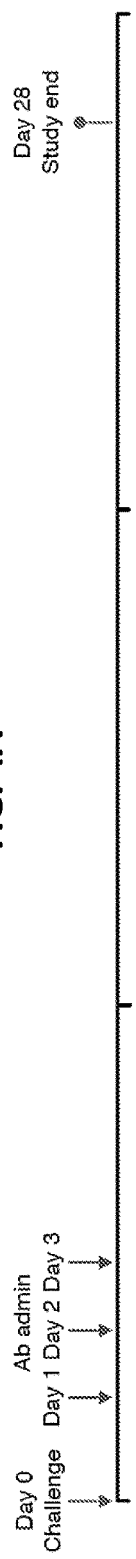
FIG. 4A
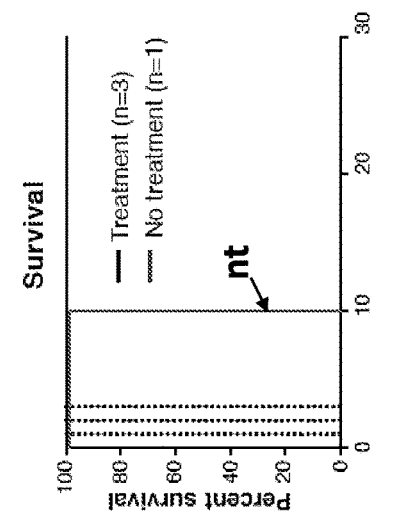
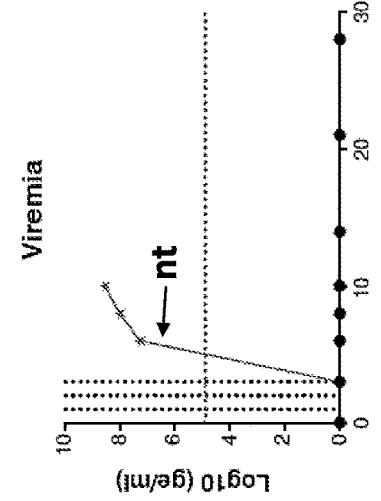
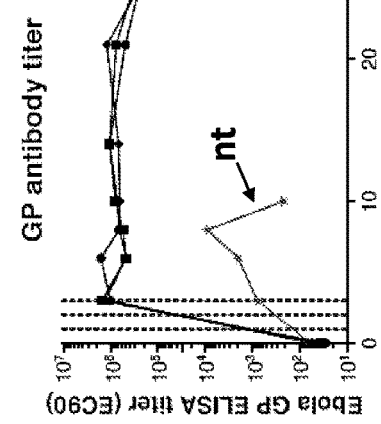

EVB114 monotherapy
FIG. 4G

EBOV mAbs neutralization at IC50 concentration in presence or absence of sGP

Direct WB

NEUTRALIZING ANTIBODIES TO EBOLA VIRUS GLYCOPROTEIN AND THEIR USE

CROSS REFERENCE TO RELATED APPLICATIONS

This is the U.S. National Stage of International Application No. PCT/US2015/060733, filed Nov. 13, 2015, which was published in English under PCT Article 21(2), which in turn claims the benefit of U.S. Provisional Application No. 62/087,087, filed Dec. 3, 2014, and U.S. Provisional Application No. 62/080,094, filed Nov. 14, 2014; each of the provisional applications is incorporated by reference herein in its entirety.

PARTIES TO A JOINT RESEARCH AGREEMENT

This invention was made under Research Collaboration Agreement No. 2007-0166 between the National Institutes of Health National Institute of Allergy and Infectious Disease and Institute for Research in Biomedicine.

FIELD OF THE DISCLOSURE

This relates to monoclonal antibodies and antigen binding fragments that specifically bind to Ebola virus (EBOV) glycoprotein (GP) and their use, for example, in methods of treating or preventing EBOV infection or EBOV disease (EVD) in a subject.

BACKGROUND

EVD is a disease in humans, chimpanzees, and monkeys, caused by infection with EBOV. This virus was first recognized in Zaire, Africa in 1976. EBOV is a member of the Filoviridae family of RNA viruses and causes a severe hemorrhagic fever with a high mortality rate. For example, infection with the Ebola virus Zaire (ZEBOV) strain of the virus is associated with a mortality rate of up to 90% in humans. Currently, there are no licensed vaccines or therapeutics approved for human use.

An enveloped virus, EBOV hides from humoral recognition behind a wide array of protective mechanisms. EBOV GP, the major envelope glycoprotein of EBOV is approximately 165 kD in size. During infection proteases of the host cell cleave a precursor of GP, termed $GP_0$, into $GP_1$ and $GP_2$. $GP_1$ is an integral membrane protein, while $GP_1$ protrudes from the mature virus. Together $GP_1$ and $GP_2$ make up the EBOV envelope spike, which is a target for neutralizing antibodies. Although certain EBOV neutralizing antibodies that bind to the EBOV GP have been identified, there is a need to develop additional neutralizing antibodies for EBOV with varying EBOV GP recognition profiles and increased neutralization potency.

SUMMARY

Isolated monoclonal antibodies and antigen binding fragments that specifically bind to an epitope on EBOV GP are provided herein. The antibodies and antigen binding fragments can neutralize EBOV infection.

In some embodiments, the antibody or antigen binding fragment comprises a heavy chain variable region ($V_H$) comprising a HCDR1, a HCDR2, and a HCDR3 of the $V_H$ set forth as SEQ ID NO: 1 (EVB114 VH) and/or a light chain variable region ($V_L$) comprising a LCDR1, a LCDR2, and a LCDR3 of the $V_L$ set forth as SEQ ID NO: 2 (EVB114 VL) and can specifically bind to EBOV GP and neutralize EBOV. In additional embodiments, the antibody or antigen binding fragment comprises a $V_H$ comprising a HCDR1, a HCDR2, and a HCDR3 of the $V_H$ set forth as SEQ ID NO: 3 (EVB100 VH) and/or a $V_L$ comprising a LCDR1, a LCDR2, and a LCDR3 of the $V_L$ set forth as SEQ ID NO: 4 (EVB100 VL) and can specifically bind to EBOV GP and neutralize EBOV. In some embodiments, the antibody or antigen binding fragment comprises a $V_H$ and a $V_L$ comprising the amino acid sequences set forth as SEQ ID NOs: 1 and 2, respectively, or SEQ ID NOs: 3 and 4, respectively.

In additional embodiments, the glycosylation (for example, fucosylation) or sequence of a disclosed antibody or antigen binding fragment can be altered compared to that observed in nature. For example the glycosylation or sequence of a disclosed of the antibody or antigen binding fragment can be altered compared to that of native antibodies to increase half-life, antibody-dependent cell-mediated cytotoxic activity, and/or EBOV neutralization or EBOV GP binding profile.

Also disclosed are compositions including the antibodies and antigen binding fragments, nucleic acids encoding the antibodies and antigen binding fragments, expression vectors comprising the nucleic acids, and isolated host cells that comprise the nucleic acids. In several embodiments, the nucleic acid molecule encoding a disclosed antibody or antigen binding fragment can be a cDNA molecule that encodes the antibody or antigen binding fragment. In additional embodiments, the nucleic acid molecule can be a bicistronic expression construct encoding the antibody or antigen binding fragment.

Surprisingly, the disclosed antibodies and antigen binding fragments potently neutralize EBOV infection in vitro and in vivo. Accordingly, a method is disclosed for treating or preventing an EBOV infection (e.g., ZEBOV infection) in a subject comprising administering a therapeutically effective amount of one or more of the disclosed antibodies or antigen binding fragments to the subject, for example to a subject at risk of or having an EBOV infection.

The antibodies, antigen binding fragments, nucleic acid molecules, vectors, and compositions disclosed herein can be used for a variety of additional purposes, such as for detecting an EBOV infection or diagnosing EVD in a subject, or detecting EBOV GP in a sample.

The foregoing and other features and advantages of this disclosure will become more apparent from the following detailed description of several embodiments which proceeds with reference to the accompanying figures.

BRIEF DESCRIPTION OF THE FIGURES

FIGS. 2A-2I are a set of graphs and tables concerning characterization of purified EBOV GP monoclonal antibodies. (2A) EBOV GP ELISA in the presence of purified monoclonal antibodies as indicated, A450. (2B) Lentivirus particles pseudotyped EBOV GP particles were incubated with increasing amounts of purified monoclonal antibodies and infection measured as in FIG. 1B. Infection %=(RLU with antibody/RLU without antibody)×100% (n=3). (2C) V gene usage, sequence analysis and IgG subclass of antibodies from Survivor 1. (2D-2G) Amino acid sequence of EVB100, EVB114 and variants descended from a putative unmutated common ancestor (UCA) for heavy and light chains. Shaded regions represent complementary determination regions 1-3. (2H) and (2I) Binding to EBOV GP expressed on the surface of MDCK-SIAT cells by different EVB100 (2H) and EVB114 (2I) versions in which all or subsets of somatic mutations in the wild type sH, sL (EVB100) or sK (EVB114) chain were reverted to the germline sequence. Shown is the ratio between the EC50 values of the variants and EC50 values of the wild-type sH/sL (EVB100) or sH/sK (EVB114). UCA, unmutated common ancestor; gH or gL, germline V-gene revertants of sH, sL, or sK in which the HCDR or LCDR3 are mature; gH-FR or gL-FR, germline V347 gene revertants of sH, sL or sK in which the HCDRs or LCDRs are mature; gH-FR1-2-4, germline V-gene revertants of sH in which the HCDRs and HFR3 are mature; gH-FR3, germline V-gene revertants of sH in which the HCDRs and HFR1, HFR2 and HFR4 are mature; wild type, somatically mutated are sH, sL, or sK. EC50 ratio values above 100 indicate lack of detectable binding.

FIGS. 4A-4I are a set of graphs showing that passive transfer of EBOV GP-specific antibodies can inhibit EBOV disease. (4A) Experimental challenge. Animals were challenged with a lethal dose of EBOV GP on Day 0 and given injections of antibody totaling 50 mg/kg at 24, 48 and 72 hours post-exposure. Surviving animals were euthanized at the conclusion of the study (Day 28). Challenge data from monoclonal antibody EVB114/EVB100 mixture (4B-4E), or EVB114 monotherapy (4F-4I). Treatment animal in black, untreated control in grey. (4B) and (4F) Ebola GP specific ELISA titer (EC90). (4C) and (4G) Viremia in blood by qRT-PCR expressed as genome equivalents (ge) per mL. (4D) and (4H) Survival. (4E) and (4I) Selected hematologic and chemistry data. Platelets (PLT), alanine transaminase (ALT), creatinine (CRE). "nt" is used to indicate data concerning the no treatment (control) animal.

FIG. 12 shows a graph illustrating the neutralization properties of the EVB100, EVB114, EVB165, and EVB166 antibodies in the presence of soluble GP (sGP), which is believed to interfere with the natural immune response to EBOV in human subjects. sGP is a GP splice variant that lacks a transmembrane domain and is therefore secreted from infected cells. Pseudotyped lentiviral vectors expressing EBOV GP were incubated with the IC50 concentration of each antibody (as shown in FIG. 2B) and sGP prior to infection of 293T cells, and infection inhibition was calculated as a percent of infection in the absence of antibody.

FIG. 13 shows a Western blot indicating that the EVB100, EVB114, EVB165, and EVB166 antibodies can immunoprecipitate several different forms of EBOV GP, including the $GP_0$, $GP_1$, $GP_2$, pre-$GP_{er}$, and $GP_{CatL}$ forms of GP. KZ52 was used as a positive control.

SEQUENCES

Figure 1A:
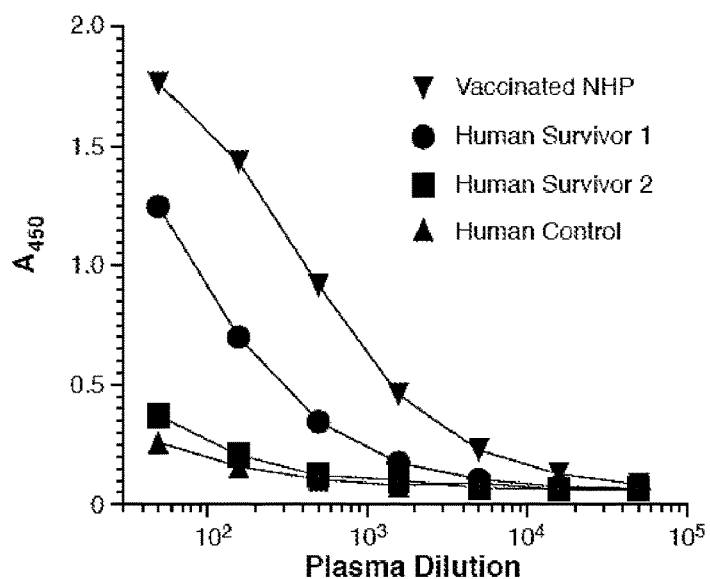
FIGS. 1A-1D are a set of graphs concerning isolation of antigen-specific monoclonal antibodies from an Ebola virus disease survivor. (1A) Plasma obtained from two human survivors, an uninfected human donor and a non-human primate (NHP) vaccinated against EBOV GP were serially diluted and analyzed by GP ELISA, A450 (n=1). (1B) Lentivirus particles expressing luciferase and bearing EBOV GP were incubated in the presence of heat inactivated serum for 1 hour prior to addition to HEK293T. Infection was determined by measuring relative luminescence (RLU) after 3 days. Infection %=(RLU with serum/RLU without serum)×100% (n=3). (1C) Immortalized B cell supernatants isolated from Survivor 1 were screened by EBOV GP ELISA A450 (n=1). (1D) Immortalized B cell supernatants from (1C) were diluted 1:50, incubated with Lentivirus particles pseudotyped with EBOV GP and infection determined as in (1B). Infection %=(RLU with supernatant/RLU without supernatant)×100% (n=1).

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~60 kb), which was created on May 10, 2017, which is incorporated by reference herein.

SEQ ID NO: 1 is the amino acid sequence of the $V_H$ of the EVB114 mAb.
EVQLVESGGGLIQPGGSLRLSCAASgfalrmydMHWVRQTIDKRLEWVSAvgpsgdtYYADSVKGRFAVSR ENAKNSLSLQMNSLTAGDTAIYYCvrsdrgvaglfdsWGQGILVTVSS SEQ ID NO: 2 is the amino acid sequence of the $V_L$ of the EVB114 mAb.
DIQMTQSPSSLSASVGDRITITCRASqafdnyVAWYQQRPGKVPKLLISaasALHAGVPSRFSGSGSGTHF TLTISSLQPEDVATYYCqnynsapltFGGGTKVEIK SEQ ID NO: 3 is the amino acid sequence of the $V_H$ of the EVB100 mAb.
QVQLQESGPGLVKPSDTLSLTCTVSggslssfyWSWIRQPPGKGLEWIGYiyysgspNYSPSLESRVTMSV DTTRNQISLKLDSVTAADTAVYYCvrasrsyywgsyrptafdsWGQGTLVTVSS SEQ ID NO: 4 is the amino acid sequence of the $V_L$ of the EVB100 mAb.
SYELTQPLSVSVSPGQTAIFTCSGDnlgdkyVCWFQQRPGQSPMLLIYqdnKRPSGIPERFSGSNSGNTAT LTISGTQSTDEADYYCqtwdstvvFGGGTKLTVL SEQ ID NO: 5 is the amino acid sequence of the $V_H$ of the EVB166 mAb.
QVQLVQSGAEVKKPGSSVKVSCKTSggtlsnyaISWVRQAPGQGLEWMGGtiptlgmsTYAPNFQGRVAIT ADKSTSTAYMELSSLRSDDTAVYYCatmgsadtsfyfymdvWGKGTTVTVSS SEQ ID NO: 6 is the amino acid sequence of the $V_L$ of the EVB166 mAb.
EIVLTQSPGTLSLSPGERATLSCRASqsvsssyLAWYQQKPGQAPRLLIYgtsSRATGIPDRFSGSASGTD FTLTISRLEPEDFAVYYCqqyayspftFGPGTKVDIK SEQ ID NO: 7 is an exemplary nucleotide sequence encoding the $V_H$ of the EVB114 mAb.
gaggtgcagctggtggagtctggggaggtttaattcagccggggggtccctgagactctcctgtgcagc ctctGGATTCGCCCTCAGAATGTACGACatgcactgggtccgtcagacaatagataaacgtctcgagtggg tctcagctGTGGGTCCTTCTGGTGACACCtactatgcagactccgtgaagggccgattcgccgtctccaga gagaatgccaagaactccttgtctcttcagatgaacagcctgacagccggggacacggctatatactattg tGTAAGGTCTGACCGAGGAGTGGCTGGCCTTTTTGACAGCtggggccagggaatcctggtcaccgtctctt cag SEQ ID NO: 8 is an exemplary nucleotide sequence encoding the $V_L$ of the EVB114 mAb.
gacatccagatgacccagtctccatcatccctgtctgcatctgtgggagacagaatcaccatcacttgccg ggcgagtCAGGCCTTTGACAATTATgtagcctggtatcaacagagaccagggaaggttcctaagctcctga tctctGCTGCATCCgctttgcacgcagggtcccatctcgcttcagcggcagtggctctgggacacatttc actctcaccatcagcagcctgcagcctgaagatgttgcaacttattactgtCAAAACTATAACAGTGCCCC

GCTCACTttcggcggagggaccaaggtggagatcaaac

SEQ ID NO: 9 is an exemplary nucleotide sequence encoding the $V_H$ of the EVB100 mAb.
caggtgcagctgcaggagtcgggcccaggactggtgaagccttcggataccctgtccctcacctgtactgt ctctGGTGGCTCCCTCAGTAGTTTCTACtggagctggatccggcagcccccagggaagggactggagtgga ttgggtatATCTATTACAGTGGGAGCCCCaactacagcccctccctcgagagtcgagtcaccatgtcagta gacacgaccaggaaccagatctccctgaagttggactctgtgaccgcggcggacacggccgtgtattactg tGTGAGAGCCTCCCGAAGTTACTATTGGGGGAGTTATCGCCCAACGGCTTTTGACTCCtggggccagggaa ccctggtcaccgtctcctcag SEQ ID NO: 10 is an exemplary nucleotide sequence encoding the $V_L$ of the EVB100 mAb.
tcctatgagctgactcagccactctcagtgtccgtgtccccaggccagacagccatcttcacctgctctgg agatAATTTGGGGGATAAGTATgtttgctggtttcaacagaggccaggccagtcccctatgctgctcatct atCAAGACAATaagcggccctcggggatccctgagcgattctctggctccaactctgggaacacagccact ctgactatcagcgggacccagtctacagatgaggctgactattactgtCAGACGTGGGACAGCACCGTGGT

Gttcggcggagggaccaaactgaccgtcctgg

SEQ ID NO: 11 is an exemplary nucleotide sequence encoding the $V_H$ of the EVB166 mAb.
caggtccagctggtgcagtctggggctgaggtgaagaagcctgggtcctcggtgaaagtctcctgcaagac -continued ttctGGAGGCACCCTCAGCAACTATGCTatcagctgggtgcgacaggccctggacaagggcttgagtgga tgggaggcACCATTCCTACCCTTGGTATGTCCacctacgcaccgaacttccagggcagagtcgcgattacc gcggacaaatccacgagcacagcctacatggagttgagtagtctgaggtctgacgacacggccgtttatta ttgtGCGACTATGGGCAGTGCGGACACTAGTTTCTACTTCTACATGGACGTCtggggcaaagggaccacgg tcaccgtctcctcag SEQ ID NO: 12 is an exemplary nucleotide sequence encoding a variant V$_L$ of the EVB166 mAb
that includes a K104T substitution.
Gaaattgtgttgacgcagtctccaggcaccctgtctttgtctccaggggagagagccaccctctcctgcag ggccagtCAGAGTGTTAGTAGCAGCTACttagcctggtaccagcagaaacctggccaggctcccagactcc tcatctatGGTACATCCagcagggccactggcatcccagacaggttcagtggcagtgcgtctgggacagac ttcactctcaccatcagcagactggagcctgaagattttgcagtgtattactgtCAGCAGTATGCTTACTC ACCATTCACTttcggccctgggaccacagtggatatcaaac SEQ ID NO: 13 is an exemplary amino acid sequence of a precursor of the GP from Bundibugyo
EBOV (GENBANK Acc. No. ACI28624.1, which is incorporated by reference herein in its entirety).
MVTSGILQLPRERFRKTSFFVWVIILFHKVFPIPLGVVHNNTLQVSDIDKLVCRDKLSSTSQLKSVGLNLE

GNGVATDVPTATKRWGFRAGVPPKVVNYEAGEWAENCYNLDIKKADGSECLPEAPEGVRGFPRCRYVHKVS

GTGPCPEGYAFHKEGAFFLYDRLASTIIYRSTTFSEGVVAFLILPETKKDFFQSPPLHEPANMTTDPSSYY

HTVTLNYVADNFGTNMTNFLFQVDHLTYVQLEPRFTPQFLVQLNETIYTNGRRSNTTGTLIWKVNPTVDTG

VGEWAFWENKKNFTKTLSSEELSVIFVPRAQDPGSNQKTKVTPTSFANNQTSKNHEDLVPEDPASVVQVRD

LQRENTVPTPPPDTVPTTLIPDTMEEQTTSHYEPPNISRNHQERNNTAHPETLANNPPDNTTPSTPPQDGE

RTSSHTTPSPRPVPTSTIHPTTRETHIPTTMTTSHDTDSNRPNPIDISESTEPGPLTNTTRGAANLLTGSR

RTRREITLRTQAKCNPNLHYWTTQDEGAAIGLAWIPYFGPAAEGIYTEGIMHNQNGLICGLRQLANETTQA

LQLFLRATTELRTFSILNRKAIDFLLQRWGGTCHILGPDCCIEPHDWTKNITDKIDQIIHDFIDKPLPDQT

DNDNWWTGWRQWVPAGIGITGVIIAVIALLCICKFLL

SEQ ID NO: 14 is an exemplary amino acid sequence of a precursor of the GP from Sudan
EBOV (GENBANK Acc. No. ACR33190.1, which is incorporated by reference herein in its entirety).
MEGLSLLQLPRDKFRKSSFFVWVIILFQKAFSMPLGVVTNSTLEVTEIDQLVCKDHLASTDQLKSVGLNLE

GSGVSTDIPSATKRWGFRSGVPPKVFSYEAGEWAENCYNLEIKKPDGSECLPPPPDGVRGFPRCRYVHKAQ

GTGPCPGDYAFHKDGAFFLYDRLASTVIYRGVNFAEGVIAFLILAKPKETFLQSPPIREAVNYTENTSSYY

ATSYLEYEIENFGAQHSTTLFKINNNTFVLLDRPHTPQFLFQLNDTIHLHQQLSNTTGKLIWTLDANINAD

IGEWAFWENKKNLSEQLRGEELSFETLSLNETEDDDATSSRTTKGRISDRATRKYSDLVPKDSPGMVSLHV

PEGETTLPSQNSTEGRRVDVNTQETITETTATIIGTNGNNMQISTIGTGLSSSQILSSSPTMAPSPETQTS

TTYTPKLPVMTTEESTTPPRNSPGSTTEAPTLTTPENITTAVKTVLPQESTSNGLITSTVTGILGSLGLRK

RSRRQVNTRATGKCNPNLHYWTAQEQHNAAGIAWIPYFGPGAEGIYTEGLMHNQNALVCGLRQLANETTQA

LQLFLRATTELRTYTILNRKAIDFLLRRWGGTCRILGPDCCIEPHDWTKNITDKINQIIHDFIDNPLPNQD

NDDNWWTGWRQWIPAGIGITGIIIAIIALLCVCKLLC

SEQ ID NO: 15 is an exemplary amino acid sequence of a precursor of the GP from Zaire EBOV
(GENBANK Acc. No. AIO11753.1, which is incorporated by reference herein in its entirety).
MGVTGILQLPRDRFKKTSFFLWVIILFQRTFSIPLGVIHNSTLQVSDVDKLVCRDKLSSTNQLRSVGLNLE

GNGVATDVPSATKRWGFRSGVPPKVVNYEAGEWAENCYNLEIKKPDGSECLPAAPDGIRGFPRCRYVHKVS

GTGPCAGDFAFHKEGAFFLYDRLASTVIYRGTTFAEGVVAFLILPQAKKDFFSSHPLREPVNATEDPSSGY

YSTTIRYQATGFGTNETEYLFEVDNLTYVQLESRFTPQFLLQLNETIYTSGKRSNTTGKLIWKVNPEIDTT

IGEWAFWETKKNLTRKIRSEELSFTAVSNRAKNISGQSPARTSSDPGTNTTTEDHKIMASENSSAMVQVHS

QGREAAVSHLTTLATISTSPQPPTTKPGPDNSTHNTPVYKLDISEATQAEQHHRRTDNDSTTSDTPPAMTA

AGPPKAENTNTSKGTDLPDPATTTSPQNHSETAGNNNTHHQDTGEESASSGKLGLITNTIAGVAGLITGGR

RTRREAIVNAQPKCNPNLHYWTTQDEGAAIGLAWIPYFGPAAEGIYTEGLMHNQDGLICGLRQLANETTQA

LQLFLRATTELRTFSILNRKAIDFLLQRWGGTCHILGPDCCIEPHDWTKNITDKIDQIIHDFVDKTLPDQG

DNDNWWTGWRQWIPAGIGVTGVIIAVIALFCICKFVF

SEQ ID NO: 16 is an exemplary amino acid sequence of a precursor of the GP from Reston EBOV (GENBANK Acc. No. AAC54891.1, which is incorporated by reference herein in its entirety).
MGSGYQLLQLPRERFRKTSFLVWVIILFQRAISMPLGIVTNSTLKATEIDQLVCRDKLSSTSQLKSVGLNL

EGNGIATDVPSATKRWGFRSGVPPKVVSYEAGEWAENCYNLEIKKSDGSECLPLPPDGVRGFPRCRYVHKV

QGTGPCPGDLAFHKNGAFFLYDRLASTVIYRGTTFTEGVVAFLILSEPKKHFWKATPAHEPVNTTDDSTSY

YMTLTLSYEMSNFGGKESNTLFKVDNHTYVQLDRPHTPQFLVQLNETLRRNNRLSNSTGRLTWTLDPKIEP

DVGEWAFWETKKNFSQQLHGENLHFQILSTHTNNSSDQSPAGTVQGKISYHPPTNNSELVPTDSPPVVSVL

TAGRTEEMSTQGLTNGETITGFTANPMTTTIAPSPTMTSEVDNNVPSEQPNNTASIEDSPPSASNETIDHS

EMNPIQGSNNSAQSPQTKTTPAPTASPMTQDPQETANSSKLGTSPGSAAEPSQPGFTINTVSKVADSLSPT

RKQKRSVRQNTANKCNPDLHYWTAVDEGAAVGLAWIPYFGPAAEGIYIEGVMHNQNGLICGLRQLANETTQ

ALQLFLRATTELRTYSLLNRKAIDFLLQRWGGTCRILGPSCCIEPHDWTKNITDEINQIKHDFIDNPLPDH

GDDLNLWTGWRQWIPAGIGIIGVIIAIIALLCICKILC

SEQ ID NO: 17 is an exemplary amino acid sequence of a precursor of the GP from Taï Forest EBOV (GENBANK Acc. No. ACI28632.1, which is incorporated by reference herein in its entirety).
MGASGILQLPRERFRKTSFFVWVIILFHKVFSIPLGVVHNNTLQVSDIDKFVCRDKLSSTSQLKSVGLNLE

GNGVATDVPTATKRWGFRAGVPPKVVNCEAGEWAENCYNLAIKKVDGSECLPEAPEGVRDFPRCRYVHKVS

GTGPCPGGLAFHKEGAFFLYDRLASTIIYRGTTFAEGVIAFLILPKARKDFFQSPPLHEPANMTTDPSSYY

HTTTINYVVDNFGTNTTEFLFQVDHLTYVQLEARFTPQFLVLLNETIYSDNRRSNTTGKLIWKINPTVDTS

MGEWAFWENKKNFTKTLSSEELSFVPVPETQNQVLDTTATVSPPISAHNHAAEDHKELVSEDSTPVVQMQN

IKGKDTMPTTVTGVPTTTPSPFPINARNTDHTKSFIGLEGPQEDHSTTQPAKTTSQPTNSTESTTLNPTSE

PSSRGTGPSSPTVPNTTESHAELGKTTPTTLPEQHTAASAIPRAVHPDELSGPGFLTNTIRGVTNLLTGSR

RKRRDVTPNTQPKCNPNLHYWTALDEGAAIGLAWIPYFGPAAEGIYTEGIMENQNGLICGLRQLANETTQA

LQLFLRATTELRTFSILNRKAIDFLLQRWGGTCHILGPDCCIEPQDWTKNITDKIDQIIHDFVDNNLPNQN

DGSNWWTGWKQWVPAGIGITGVIIAIIALLCICKFML

SEQ ID NO: 18 is an exemplary amino acid sequence of a precursor of the soluble form of GP from Zaire EBOV (GENBANK Acc. No. AAD14584.1, which is incorporated by reference herein in its entirety).
MGVTGILQLPRDRFKRTSFFLWVIILFQRTFSIPLGVIHNSTLQVSDVDKLVCRDKLSSTNQLRSVGLNLE

GNGVATDVPSATKRWGFRSGVPPKVVNYEAGEWAENCYNLEIKKPDGSECLPAAPDGIRGFPRCRYVHKVS

GTGPCAGDFAFHKEGAFFLYDRLASTVIYRGTTFAEGVVAFLILPQAKKDFFSSHPLREPVNATEDPSSGY

YSTTIRYQATGFGTNETEYLFEVDNLTYVQLESRFTPQFLLQLNETIYTSGKRSNTTGKLIWKVNPEIDTT

IGEWAFWETKKTSLEKFAVKSCLSQLYQTEPKTSVVRVRRELLPTQGPTQQLKTTKSWLQKIPLQWFKCTV

KEGKLQCRI

SEQ ID NO: 19 is the amino acid sequence of the V$_H$ of the EVB165 mAb.
DVQLVESGGGVVQPGGSLKLACVVSgfrfsdywMSWVRQAPGKGLEWVANikqdgsgkYYVDSVKGRFTVS RDNAKNSLYLHMTSLGAEDTAVYFCaraaptgsytnilvdnvhfdyWGQGILVAVSS SEQ ID NO: 20 is the amino acid sequence of the V$_L$ of the EVB165 mAb.
GIQLTQSPGSLSASVGDSVTITCRPNqniatyINWYQQTPGKAPKLLIYaasILQSGVPSRFSGAGSGTHF TLIISTLQPEDSATYYCqqsystpwtFGQGTKVEIK SEQ ID NO: 21 is an exemplary nucleotide sequence encoding the V$_H$ of the EVB165 mAb.
gatgtgcagttggtggagtctggggggaggcgtggtccagccggggggtccctgaaactcgcctgtgtagt ctctGGATTCAGGTTTAGTGACTACTGGatgagttgggtccgccaggccccagggaaggggctggaatggg tggccaacATAAAACAAGATGGAAGTGGGAAGtactatgtggactccgtgaagggccgattcaccgtctcc agagacaacgccaagaactcactgtatctacacatgaccagcctgggagccgaggacacggccgtatactt ctgcGCGAGAGCAGCCCCCACCGGCTCCTACACTAATATCCTAGTCGACAACGTCCACTTCGACTACtggg gccagggaatcctggtcgccgtctcctcag SEQ ID NO: 22 is an exemplary nucleotide sequence encoding the V$_L$ of the EVB165 mAb.
ggcatccagctgacccagtctccaggctccctgtctgcatctgtaggagacagtgtcaccatcacttgccg gccaaatCAGAACATCGCCACCTATataaattggtatcagcagacaccagggaaagcccctaagctcctga tctatGCCGCATCCattttgcagagtggggtcccatcaaggttcagtggcgctggatctgggacacatttc actctcatcatcagtacccctacaacctgaggattctgcaacttactactgcCAACAGAGTTACAGTACCCC

GTGGACAttcggccaagggaccaaagtggaaatcaaac

SEQ ID NO: 23 is the amino acid sequence of the V$_H$ of the EVB167 mAb.
AVQLVQSGAEVKKPGTTVKISCKVSgytfiqeyIHWVQQAPGKGLVWMGLgdpennetLYSEDFQGRVTMT ADTSSDTAYLELRSLTFADTAVYFCtsrkswWGQGTLVTVAS SEQ ID NO: 24 is the amino acid sequence of the V$_L$ of the EVB167 mAb.
ELVLTQSPGTLSLSPGESATLSCRASqslssdsVSWFQQKPGQAPRLVIHgtsKRATGIPDRFSGGGSGTD FTLTIARLEPEDFAVYYCqrsgygmsvtwtFGQGTTVEIK SEQ ID NO: 25 is an exemplary nucleotide sequence encoding the V$_H$ of the EVB167 mAb.
gcggtccagttggtacaatctggggctgaggtgaagaagcctgggaccaccgtcaaaatctcctgcaaagt ttctGGATACACCTTCATTCAAGAATACatacactgggtgcaacaggcccctggaaaagggcttgtgtgga tgggacttGGTGACCCTGAAAATAATGAGACTctatattcagaggatttccaaggcagagtcaccatgacc gcggacacatcctcagacacagcctatctggaactgcgcagcctgacatttgcagacacggccgtctattt ctgtACATCACGAAAGTCCTGGtggggccagggaaccctggtcaccgtcgcctcag SEQ ID NO: 26 is an exemplary nucleotide sequence encoding the V$_L$ of the EVB167 mAb.
gaacttgtgttgacgcagtctccaggcaccctgtctttgtctccaggggaaagcgccaccctctc ctgtagggccagtCAGAGTCTTAGCAGCGACTCTgtatcttggttccagcagaaacctggccagg ctcccaggctcgtcatccatGGTACATCAaagagggccactggcatcccagacaggttcagtggc ggtgggtctgggacagacttcactctcaccatcgccagactggagcctgaggattttgcagtcta ttattgtCAGCGGTCTGGGTATGGTATGTCAGTCACGTGGACGttcggccaagggaccacggtgg agatcaaac SEQ ID NO: 27 is an exemplary nucleotide sequence encoding the V$_L$ of the EVB167 mAb.
gaacttgtgttgacgcagtctccaggcaccctgtctttgtctccaggggaaagcgccaccctctc ctgtagggccagtCAGAGTCTTAGCAGCGACTCTgtatcttggttccagcagaaacctggccagg ctcccaggctcgtcatccatGGTACATCAaagagggccactggcatcccagacaggttcagtggc ggtgggtctgggacagacttcactctcaccatcgccagactggagcctgaggattttgcagtcta ttattgtCAGCGGTCTGGGTATGGTATGTCAGTCACGTGGACGtttggccaagggaccacggtgg agatcaaac SEQ ID NO: 28 is the amino acid sequence of the V$_H$ of the EVB114 version 2 mAb.
EVQLVESGGGLIQPGGSLRLSCAASgfalrsydMHWVRQTIDKRLEWVSAvgpsgdtYYADSVKGRFAVSR ENAKNSLSLQMNSLTAGDTAIYYCvrsdrgvaglfdsWGQGILVTVSS SEQ ID NO: 29 is the amino acid sequence of the V$_L$ of the EVB114 version 2 mAb.
DIQMTQSPSSLSASVGDRITITCRASqafsnyVAWYQQRPGKVPKLLISaasALHAGVPSRFSGSGSGTHF TLTISSLQPEDVATYYCqnynsapltFGGGTKVEI SEQ ID NO: 30 is an exemplary nucleotide sequence encoding the V$_H$ of the EVB114 version 2 mAb.
gaagtgcagctggtggagtctggaggaggtctgattcagcccggggggttccctgcgtctgagttgtgccgc atctGGATTTGCTCTGCGAAGCTACGACatgcactgggtgagacagactatcgataagcgcctggagtggg

```
tgtctgctGTCGGCCCCAGTGGAGACACCtactatgcagattcagtgaaggggaggttcgcagtctcccgg gaaaacgccaaaaattccctgagcctgcagatgaactctctgaccgccggcgacacagctatctactattg cGTCAGGAGCGATAGAGGGGTCGCAGGACTGTTTGATTCAtggggtcagggtattctggtcaccgtgtctt ca
```

SEQ ID NO: 31 is an exemplary nucleotide sequence encoding the V$_L$ of the EVB114 version 2 mAb.
```
gatattcagatgactcagagcccttcctcactgtccgcatccgtgggagaccgtattactattacttgtag agcttctCAGGCTTTTTCTAACTACgtggcttggtatcagcagaggcccggcaaggtccctaaactgctga tctccGCCGCTTCTgcactgcatgctggagtgccaagccggttctctggaagtggatcagggactcacttc accctgacaatttccagcctgcagcccgaggatgtcgcaacctactattgcCAGAACTACAACAGTGCTCC CCTGACAttcggtggtggaacaaaggtcgagatc
```

SEQ ID NOs: 32-61 are amino acid sequences of antibody heavy and light chain CDRs by IMGT positioning.
SEQ ID NO: 62 is the amino acid sequence of a variant V$_L$ of the EVB166 mAb that includes a K104T substitution.
```
EIVLTQSPGTLSLSPGERATLSCRASQSVSSSYLAWYQQKPGQAPRLLIYGTSSRATGIPDRFSGSASGTD

FTLTISRLEPEDFAVYYCQQYAYSPFTFGPGTTVDIK
```

SEQ ID NOs: 63-65 are primer and probe sequences.

SEQ ID NO: 66 is the amino acid sequence of a modified fragment of EBOV GP.

For SEQ ID NOs: 1-6, 19-20, 23-24, and 28-29 the amino acid sequence of the IMGT CDRs are shown in bold and lower case letters. For SEQ ID NOs: 7-12, 21-22, 25-27, and 30-31, the nucleotide sequences encoding IMGT CDRs are shown in bold and upper case letters.

DETAILED DESCRIPTION

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition into a subject by a chosen route.

Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for inhibiting EBOV infection in a subject. Agents include proteins, antibodies, nucleic acid molecules, compounds, small molecules, organic compounds, inorganic compounds, or other molecules of interest. An agent can include a therapeutic agent, a diagnostic agent or a pharmaceutical agent. In some embodiments, the agent is a polypeptide agent (such as an EBOV-neutralizing antibody), or an anti-viral agent. Some agents may be useful to achieve more than one result.

Amino acid substitution: The replacement of one amino acid in peptide with a different amino acid.

Antibody: An immunoglobulin, antigen-binding fragment, or derivative thereof, that specifically binds and recognizes an analyte (antigen) such as EBOV GP. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2$^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., Immunology, $3^{rd}$ Ed., W.H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the $V_H$ and $V_L$ combine to specifically bind the antigen. In additional embodiments, only the $V_H$ is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). Any of the disclosed antibodies can include a heterologous constant domain. For example the antibody can include constant domain that is different from a native constant domain, such as a constant domain including one or more modifications (such as the "LS" mutations) to increase half-life.

References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions which have substantially no effect on antigen binding or other immunoglobulin functions. (See, for example, Harlow & Lane, *Antibodies, A Laboratory Manual*, 2$^{nd}$ ed. Cold Spring Harbor Publications, New York (2013).)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel*. 1$^{st}$ Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008)

Antibody or antigen binding fragment that neutralizes EBOV: An antibody or antigen binding fragment that specifically binds to EBOV GP (such as ZEBOV GP) in such a way as to inhibit a biological function associated with EBOV GP (such as binding to its target receptor). In several embodiments, an antibody or antigen binding fragment that neutralizes EBOV reduces the infectious titer of EBOV. In some embodiments, an antibody or antigen binding fragment that specifically binds to EBOV GP can neutralize two or more (such as 3, 4, 5, 6, 7, 8, 9, 10, or more) strains of EBOV.

Biological sample: A sample obtained from a subject. Biological samples include all clinical samples useful for detection of disease or infection (for example, EVD or EBOV infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having an Ebola infection.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), or combinations thereof. A bispecific antibody can include one or more constant domains, but does not necessarily include a constant domain.

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, Antibodies, *A Laboratory Manual*, 2$^{nd}$ ed. Cold Spring Harbor Publications, New York (2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intraorganismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Conjugate: A complex of two molecules linked together, for example, linked together by a covalent bond. In one embodiment, an antibody is linked to an effector molecule; for example, an antibody that specifically binds to EBOV GP covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, an EBOV-specific antibody can include up to 1, 2, 3, 4, 5, 6, 7, 8, 9, or up to 10 conservative substitutions compared to a reference antibody sequence and retain specific binding activity for EBOV antigen, and/or EBOV neutralization activity. The term conservative variation also includes the use of a substituted amino acid in place of an unsubstituted parent amino acid.

Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are known. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the EBOV-specific antibody, such as the ability to specifically bind to EBOV GP. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control sample obtained from a healthy patient. In other embodiments, the control is a positive control sample obtained from a patient diagnosed with EBOV infection. In still other embodiments, the control is a historical control or standard reference value or range of values (such as a previously tested control sample, such as a group of EBOV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a protein (for example, an antibody that specifically binds EBOV GP) that includes a sequence that is degenerate as a result of the genetic code. There are twenty natural amino acids, most of which are specified by more than one codon. Therefore, all degenerate nucleotide sequences are included as long as the amino acid sequence of the antibody that binds EBOV GP encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013).

Detecting: To identify the existence, presence, or fact of something. General methods of detecting are known and may be supplemented with the protocols and reagents disclosed herein. For example, included herein are methods of detecting a cell that expresses EBOV GP in a subject.

Ebola Virus (EBOV): An enveloped, non-segmented, negative, single-stranded RNA virus that causes Ebola virus disease (EVD), formerly known as Ebola hemorrhagic fever (EHF), in humans. EBOV spreads through human-to-human transmission, with infection resulting from direct contact with blood, secretions, organs or other bodily fluids of infected people, and indirect contact with environments contaminated by such fluids (see, e.g., Baize et al., N Engl J Med., 371, 1418-1425, 2014, which is incorporated by reference herein).

The symptoms of EBOV infection and disease are well-known. Briefly, in humans, EBOV has an initial incubation period of 2 to 21 days (7 days on average, depending on the strain) followed by a rapid onset of non-specific symptoms such as fever, extreme fatigue, gastrointestinal complaints, abdominal pain, anorexia, headache, myalgias and/or arthralgias. These initial symptoms last for about 2 to 7 days after which more severe symptoms related to hemorrhagic fever occur, including hemorrhagic rash, epistaxis, mucosal bleeding, hematuria, hemoptysis, hematemesis, melena, conjunctival hemorrhage, tachypnea, confusion, somnolence, and hearing loss. In general, the symptoms last for about 7 to 14 days after which recovery may occur. Death can occur 6 to 16 days after the onset of symptoms (Geisbert and Jahrling, Nat Med., 10, S110-21. 2004; Hensley et al., Curr Mol Med, 5, 761-72, 2005). People are infectious as long as their blood and secretions contain the virus; the virus was isolated from semen 61 days after onset of illness in a man who was infected in a laboratory (Baize et al., N Engl J Med., 371, 1418-1425, 2014).

Immunoglobulin M (IgM) antibodies to the virus appear 2 to 9 days after infection whereas immunoglobulin G (IgG) antibodies appear approximately 17 to 25 days after infection, which coincides with the recovery phase. In survivors of EVD, both humoral and cellular immunity are detected, however, their relative contribution to protection is unknown (Sullivan, Yang, and Nabel, J Virol, 77, 9733-7, 2003).

Five distinct EBOV species are known, including Bundibugyo (BDBV), Reston (RESTV), Sudan (SUDV), Tai Forest (TAFV), and Zaire (ZEBOV) (Kuhn, J. H., et al., Arch Virol, 2013. 158(1): p. 301-11). BDBV, EBOV, and SUDV have been associated with large outbreaks of EVD in Africa and reported case fatality rates of up to 90%. Exemplary amino acid sequences of EBOV GP from the BDBV, RESTV, SUDV, TAFV, and ZEBOV strains are set forth as SEQ ID NOs: 13-17.

The EBOV genome includes about 19K nucleotides, which encode seven structural proteins including NP (a nucleoprotein), VP35 (a polymerase cofactor), VP30 (a transcription activator), VP24, L (a RNA polymerase), and GP (a glycoprotein).

EBOV glycoprotein (GP): The virion-associated transmembrane glycoprotein of EBOV is initially synthesized as a precursor protein of about 675 amino acids in size, designated $GP_0$. Individual $GP_0$ polypeptides form a homotrimer and undergo glycosylation within the Golgi apparatus as well as processing to remove the signal peptide, and cleavage by a cellular protease between approximately positions 500/501 to generate separate $GP_1$ and $GP_2$ polypeptide chains, which remain associated as $GP_1/GP_2$ protomers within the homotrimer. The extracellular $GP_1$ polypeptide (approx. 140 kDa) is derived from the amino-terminal portion of the $GP_0$ precursor, and the $GP_2$ polypeptide (approx. 26 kDa), which includes extracellular, transmembrane, and cytosolic domains, is derived from the carboxyl-terminal portion of the $GP_0$ precursor. $GP_1$ is responsible for attachment to new host cells while $GP_2$ mediates fusion with those cells.

A splice variant of the gene encoding EBOV GP encodes a soluble glycoprotein (sGP) that is secreted from the viral host cell. (Volchkov et al., Virology, 245, 110-119, 1998). sGP and $GP_1$ are identical in their first 295 N-terminal amino acids, whereas the remaining 69 C-terminal amino acids of sGP and 206 amino acids of $GP_1$ are encoded by different reading frames. It has been suggested that secreted sGP may effectively bind antibodies that might otherwise be protective (see, e.g., Sanchez el al., Proc. Natl. Acad. Sci. U.S.A., 93, 3602-3607, 1996; and Volchkov et al., Virology, 245, 110-119, 1998, each of which is incorporated by reference herein in its entirety).

Comparisons of the predicted amino acid sequences for the GPs of the different EBOV strains show conservation of amino acids in the amino-terminal and carboxy-terminal regions with a highly variable region in the middle of the protein (Feldmann el al., Virus Res. 24: 1-19, 1992). The GP of Ebola viruses are highly glycosylaled and contain both N-linked and O-linked carbohydrates that contribute up to 50% of the molecular weight of the protein. Most of the glycosylation sites are found in the central variable region of GP.

The numbering used in the disclosed EBOV GPs and fragments thereof is relative to the EBOV GP protein from the Zaire strain set forth as SEQ ID NO: 15, unless context indicates otherwise. Effector molecule: A molecule intended to have or produce a desired effect; for example, a desired effect on a cell to which the effector molecule is targeted. Effector molecules can include, for example, polypeptides and small molecules. In one non-limiting example, the effector molecule is a toxin. Some effector molecules may have or produce more than one desired effect.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on EBOV GP.

Expression: Transcription or translation of a nucleic acid sequence. For example, an encoding nucleic acid sequence (such as a gene) can be expressed when its DNA is transcribed into an RNA or RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc polypeptide: The polypeptide including the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region includes immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to include residues C226 or P230 to its carboxyl-terminus, wherein the numbering is according to the EU index as in Kabat. For IgA, the Fc region includes immunoglobulin domains Calpha2 and Calpha3 (Cα2 and Cα3) and the lower part of the hinge between Calpha1 (Cα1) and Cα2.

Heterologous: Originating from a different genetic source. A nucleic acid molecule that is heterologous to a cell originated from a genetic source other than the cell in which it is expressed.

IgA: A polypeptide belonging to the class of antibodies that are substantially encoded by a recognized immunoglobulin alpha gene. In humans, this class or isotype comprises $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece. IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$. In mice, this class comprises $IgG_1$, $IgG_2a$, $IgG_2b$, $IgG_3$.

Immune complex: The binding of antibody or antigen binding fragment (such as a scFv) to a soluble antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link an effector molecule to an antibody. In some embodiments, the provided conjugates include a linker between the effector molecule or detectable marker and an antibody. In some cases, a linker is a peptide within an antigen binding fragment (such as an Fv fragment) which serves to indirectly bond the variable heavy chain to the variable light chain. Non-limiting examples of peptide linkers include glycine, serine, and glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Nucleic acid (molecule or sequence): A deoxyribonucleotide or ribonucleotide polymer or combination thereof including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. "cDNA"

refers to a DNA that is complementary or identical to an mRNA, in either single stranded or double stranded form.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Science*, 22th ed., Pharmaceutical Press, London, UK (2012), describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as on-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation, such as at least 80%, at least 90%, at least 95% or greater of the total peptide or protein content.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide (such as an insect ferritin heavy or light chain) are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Specifically bind: When referring to an antibody or antigen binding fragment, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an antigen present on the surface of a pathogen, for example EBOV GP) and does not bind in a significant amount to other proteins or polysaccharides present in the sample or subject. With reference to an antibody-antigen complex, specific binding of the antigen and antibody has a $K_d$ of less than about $10^{-7}$ Molar, such as less than about $10^{-8}$ Molar, $10^{-9}$, or even less than about $10^{-10}$ Molar.

$K_d$ refers to the dissociation constant for a given interaction, such as a polypeptide ligand interaction or an antibody antigen interaction. For example, for the bimolecular interaction of an antibody or antigen binding fragment (such as EVB114 or an antigen binding fragment thereof) and an antigen (such as EBOV GP) it is the concentration of the individual components of the bimolecular interaction divided by the concentration of the complex.

The antibodies disclosed herein specifically bind to a defined target (or multiple targets, in the case of a bispecific antibody). Thus, an antibody that specifically binds to an epitope on EBOV GP is an antibody that binds substantially to EBOV GP, including cells or tissue expressing EBOV GP, substrate to which the EBOV GP is attached, or EBOV GP in a biological specimen. It is, of course, recognized that a certain degree of non-specific interaction may occur between an antibody or conjugate including an antibody (such as an antibody that specifically binds EBOV GP or conjugate including such antibody) and a non-target (such as a cell that does not express EBOV GP). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, 2$^{nd}$ ed., Cold Spring Harbor Publications, New York (2013), for a description of immunoassay formats and conditions that can be used to determine specific immunoreactivity.

Subject: Living multi-cellular vertebrate organisms, a category that includes human and non-human mammals. In an example, a subject is a human. In an additional example, a subject is selected that is in need of inhibiting of an EBOV infection. For example, the subject is either uninfected and at risk of EBOV infection or is infected in need of treatment.

Therapeutically effective amount: The amount of agent, such as a disclosed EBOV GP specific antibody or antigen binding fragment that is sufficient to prevent, treat (including prophylaxis), reduce and/or ameliorate the symptoms and/or underlying causes of a disorder or disease, for example to prevent, inhibit, and/or treat EBOV infection. In some embodiments, a therapeutically effective amount is sufficient to reduce or eliminate a symptom of a disease, such as EVD. For instance, this can be the amount necessary to inhibit or prevent EBOV replication or to measurably alter outward symptoms of the EBOV infection. Ideally, a therapeutically effective amount provides a therapeutic effect without causing a substantial cytotoxic effect in the subject.

In some embodiments, a desired response is to inhibit or reduce or prevent EBOV infection. The EBOV infection does not need to be completely eliminated or reduced or prevented for the method to be effective. For example, administration of a therapeutically effective amount of the agent can reduce or inhibit the EBOV infection (for example, as measured by infection of cells, or by number or percentage of subjects infected by EBOV, or by an increase in the survival time of infected subjects) by a desired amount, for example by at least 10%, at least 20%, at least 50%, at least 60%, at least 70%, at least 80%, at least 90%, at least 95%, at least 98%, or even at least 100% (elimination or prevention of detectable EBOV infection, as compared to a suitable control.

A therapeutically effective amount of an antibody or antigen binding fragment that specifically binds EBOV GP that is administered to a subject will vary depending upon a number of factors associated with that subject, for example the overall health and/or weight of the subject. A therapeutically effective amount encompasses a fractional dose that contributes in combination with previous or subsequent administrations to attaining a therapeutic response. For example, a therapeutically effective amount of an agent can be administered in a single dose, or in several doses, for example daily, during a course of treatment lasting several days or weeks. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Transformed: A transformed cell is a cell into which a nucleic acid molecule has been introduced by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Treating or preventing a disease: Inhibiting the full development of a disease or condition, for example, in a subject who is at risk of or has an EBOV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease for the purpose of reducing the risk of developing pathology.

The term "reduces" is a relative term, such that an agent reduces a disease or condition (or a symptom of a disease or condition) if the disease or condition is quantitatively diminished following administration of the agent, or if it is diminished following administration of the agent, as compared to a reference agent. Similarly, the term "prevents" does not necessarily mean that an agent completely eliminates the disease or condition, so long as at least one characteristic of the disease or condition is eliminated. Thus, an antibody that reduces or prevents an infection, can, but does not necessarily completely, eliminate such an infection, so long as the infection is measurably diminished, for example, by at least about 50%, such as by at least about 70%, or about 80%, or even by about 90% the infection in the absence of the agent, or in comparison to a reference agent.

Under conditions sufficient for: A phrase that is used to describe any environment that permits a desired activity. In one example the desired activity is formation of an immune complex. In particular examples the desired activity is treatment of EBOV infection.

Vector: Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. In some embodiments, a viral vector is provided that comprises one or more nucleic acid molecules encoding a disclosed antibody or antigen binding fragment that specifically binds to EBOV GP and neutralizes EBOV. In some embodiments, the viral vector can be an adeno-associated virus (AAV) vector. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

II. Description of Several Embodiments

Isolated monoclonal antibodies and antigen binding fragments that specifically bind an epitope on EBOV GP protein are provided. The antibodies and antigen binding fragments can be fully human. In several embodiments, the antibodies and antigen binding fragments can be used to neutralize EBOV infection. Also disclosed herein are compositions including the antibodies and antigen binding fragments and a pharmaceutically acceptable carrier. Nucleic acids encoding the antibodies or antigen binding fragments, expression vectors including these nucleic acids, and isolated host cells that express the nucleic acids are also provided.

The antibodies, antigen binding fragments, nucleic acid molecules, host cells, and compositions can be used for research, diagnostic and therapeutic purposes. For example, the monoclonal antibodies and antigen binding fragments can be used to diagnose or treat a subject with an EBOV, or can be administered prophylactically to prevent EBOV infection in a subject. In some embodiments, the antibodies can be used to determine EBOV titer in a subject.

A. Neutralizing Monoclonal Antibodies and Antigen Binding Fragments

This disclosure provides the novel EVB114, EVB114 version 2, EVB100, EVB165, EVB166, and EVB167 antibodies and variants thereof (including antigen binding fragments), which specifically bind to EBOV GP. The disclosed antibodies and antigen binding fragments are surprisingly effective for neutralization of EBOV. For example, as discussed in Example 1, the EVB114 antibody or a combination of EVB114 and EVB100 neutralize EBOV in in vitro assays and were 100% effective in preventing lethality in a primate model of human EBOV infection.

In some embodiments, the antibodies and antigen binding fragments include a $V_H$ and a $V_L$ and specifically bind to EBOV GP and neutralize EBOV infection. In several embodiments, the antibody or antigen binding fragment can include a $V_H$ comprising a HCDR1, a HCDR2 and a HCDR3, and a $V_L$ comprising a LCDR1, a LCDR2, and a LCDR3, and specifically bind to EBOV GB and neutralize EBOV infection. In several embodiments, the antibody or antigen binding fragment includes a $V_H$ and a $V_L$ including the HCDR1, HCDR2, HCDR3, LCDR1, LCDR2, and LCDR3, respectively, of one of the EVB114, EVB114 version 2, EVB100, EVB165, EVB166, or EVB167 antibodies, and can specifically bind to EBOV GP and neutralize EBOV.

In some embodiments, the antibody or antigen binding fragment includes a HCDR1, a HCDR2, a HCDR3, a LCDR1, a LCDR2, and a LCDR3 comprising amino acid sequences that are at least 90% (for example, at least 91%, at least 92%, at least 93%, at least 94%, at least 95%, at least 96%, at least 97%, at least 98%, or at least 99%) identical to the amino acid sequences of the CDRs of one of the EVB114, EVB114 version 2, EVB100, EVB165, EVB166, or EVB167 antibodies, and can specifically bind to EBOV GP and neutralize EBOV.

Various CDR numbering schemes (such as the Kabat, Chothia or IMGT numbering schemes) can be used to determine CDR positions. The discussion of monoclonal antibodies below refers to monoclonal antibodies that include a $V_H$ and a $V_L$ including CDRs with reference to the IMGT numbering scheme (unless the context indicates otherwise). The amino acid sequence and the CDR positions of the heavy and light chain of the EVB114, EVB114 version 2, EVB100, EVB165, EVB166, or EVB167 antibodies according to the IMGT numbering scheme are shown in Table 1. In several embodiments, an antibody or antigen binding fragment is provided that includes the IMGT CDRs of an antibody listed in Table 1, and can specifically bind to EBOV GP and neutralize EBOV.

TABLE 2

IMGT CDR sequences of EBOV GP specific antibodies

EVB114 $V_H$

| $V_H$ | SEQ ID NO: 1 positions | A.A. Sequence | CDR SEQ ID NO |
|---|---|---|---|
| HCDR1 | 26-33 | GFALRMYD | 32 |
| HCDR2 | 51-57 | VGPSGDT | 33 |
| HCDR3 | 96-108 | VRSDRGVAGLFDS | 34 |

TABLE 2-continued

IMGT CDR sequences of EBOV GP specific antibodies

EVB114 V$_L$

| V$_L$ | SEQ ID NO: 2 positions | A.A. Sequence | CDR SEQ ID NO |
|---|---|---|---|
| LCDR1 | 27-32 | QAFDNY | 35 |
| LCDR2 | 50-52 | AAS | 36 |
| LCDR3 | 89-97 | QNYNSAPLT | 37 |

EVB114 version 2 V$_H$

| V$_H$ | SEQ ID NO: 28 positions | A.A. Sequence | CDR SEQ ID NO |
|---|---|---|---|
| HCDR1 | 26-33 | GFALRSYD | 38 |
| HCDR2 | 51-57 | VGPSGDT | 33 |
| HCDR3 | 96-108 | VRSDRGVAGLFDS | 34 |

EVB114 version 2 V$_L$

| V$_L$ | SEQ ID NO: 29 positions | A.A. Sequence | CDR SEQ ID NO |
|---|---|---|---|
| LCDR1 | 27-32 | QAFSNY | 39 |
| LCDR2 | 50-52 | AAS | 36 |
| LCDR3 | 89-97 | QNYNSAPLT | 37 |

EVB100 V$_H$

| V$_H$ | SEQ ID NO: 3 positions | A.A. Sequence | CDR SEQ ID NO |
|---|---|---|---|
| HCDR1 | 26-33 | GGSLSSFY | 40 |
| HCDR2 | 51-57 | IYYSGSP | 41 |
| HCDR3 | 96-114 | VRASRSYYWGSYRPTAFDS | 42 |

EVBb100 V$_L$

| V$_L$ | SEQ ID NO: 4 positions | A.A. Sequence | CDR SEQ ID NO |
|---|---|---|---|
| LCDR1 | 26-31 | NLGDKY | 43 |
| LCDR2 | 49-51 | QDN | 44 |
| LCDR3 | 88-95 | QTWDSTVV | 45 |

EVB165 V$_H$

| V$_H$ | SEQ ID NO: 19 positions | A.A. Sequence | CDR SEQ ID NO |
|---|---|---|---|
| HCDR1 | 26-33 | GFRFSDYW | 46 |
| HCDR2 | 51-58 | IKQDGSGK | 47 |
| HCDR3 | 97-117 | ARAAPTGSYTNILVDNVHFDY | 48 |

EVB165 V$_L$

| V$_L$ | SEQ ID NO: 20 positions | A.A. Sequence | CDR SEQ ID NO |
|---|---|---|---|
| LCDR1 | 27-32 | QNIATY | 49 |
| LCDR2 | 50-52 | AAS | 36 |
| LCDR3 | 89-97 | QQSYSTPWT | 50 |

EVB166 V$_H$

| V$_H$ | SEQ ID NO: 5 positions | A.A. Sequence | CDR SEQ ID NO |
|---|---|---|---|
| HCDR1 | 26-33 | GGTLSNYA | 51 |
| HCDR2 | 51-58 | TIPTLGMS | 52 |
| HCDR3 | 97-112 | ATMGSADTSFYFYMDV | 53 |

EVB166 V$_L$

| V$_L$ | SEQ ID NO: 6 positions | A.A. Sequence | CDR SEQ ID NO |
|---|---|---|---|
| LCDR1 | 27-33 | QSVSSSY | 54 |
| LCDR2 | 51-53 | GTS | 55 |
| LCDR3 | 90-98 | QQYAYSPFT | 56 |

EVB167 V$_H$

| V$_H$ | SEQ ID NO: 23 positions | A.A. Sequence | CDR SEQ ID NO |
|---|---|---|---|
| HCDR1 | 26-33 | GYTFIQEY | 57 |
| HCDR2 | 51-58 | GDPENNET | 58 |
| HCDR3 | 97-102 | TSRKSW | 59 |

EVB167 V$_L$

| V$_L$ | SEQ ID NO: 24 positions | A.A. Sequence | CDR SEQ ID NO |
|---|---|---|---|
| LCDR1 | 27-33 | QSLSSDS | 60 |
| LCDR2 | 51-53 | GTS | 55 |
| LCDR3 | 90-101 | QRSGYGMSVTWT | 61 |

In several embodiments, the antibody or antigen binding fragment includes IMGT CDRs, such as those listed in Table 1, and can specifically bind to EBOV GP and neutralize EBOV.

EVB114

In some embodiments, the antibody or antigen binding fragment can be based on or derived from the EVB114 antibody, and can specifically bind to EBOV GP and neutralize EBOV. For example, in some embodiments, the antibody or antigen binding fragment can comprise a $V_H$ comprising a HCDR1, a HCDR2, and a HCDR3 of the $V_H$ set forth as SEQ ID NO: 1 (EVB114 $V_H$), and a $V_L$ comprising a LCDR1, a LCDR2, and a LCDR3 of the $V_L$ set forth as SEQ ID NO: 2 (EVB114 $V_L$), and can specifically bind to EBOV GP and neutralize EBOV. In some embodiments, the antibody or antigen binding fragment includes a $V_H$ including a HCDR1, a HCDR2, and a HCDR3 including amino acids 26-33, 51-57, and 96-108 of SEQ ID NO: 1, respectively, and can specifically bind to EBOV GP and neutralize EBOV. In further embodiments, the antibody or antigen binding fragment includes a $V_L$ including a LCDR1, a LCDR2, and a LCDR3 including amino acids 27-32, 50-52, and 89-97 of SEQ ID NO: 2, respectively, and can specifically bind to EBOV GP and neutralize EBOV. In additional embodiments, the antibody or antigen binding fragment includes a $V_H$ including a HCDR1, a HCDR2, and a HCDR3 including amino acids 26-33, 51-57, and 96-108 of SEQ ID NO: 1, respectively, and a $V_L$ including a LCDR1, a LCDR2, and a LCDR3 including amino acids 27-32, 50-52, and 89-97 of SEQ ID NO: 2, respectively, and can specifically bind to EBOV GP and neutralize EBOV.

In some embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-57, and 96-108, respectively, of SEQ ID NO: 1, and can specifically bind to EBOV GP and neutralize EBOV. In some embodiments, the antibody or antigen binding fragment includes a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-32, 50-52, and 89-97, respectively, of SEQ ID NO: 2, and can specifically bind to EBOV GP and neutralize EBOV. In additional embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-57, and 96-108, respectively, of SEQ ID NO: 1, and a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-32, 50-52, and 89-97, respectively, of SEQ ID NO: 2, and can specifically bind to EBOV GP and neutralize EBOV.

In some embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 1, and can specifically bind to EBOV GP and neutralize EBOV. In more embodiments, the antibody or antigen binding fragment includes a $V_L$ including an amino acid sequence at least 80%, 90%, 95%, 96%, 97%, 98%, or 99% identical to the amino acid sequence set forth as SEQ ID NO: 2, and can specifically bind to EBOV GP and neutralize EBOV. In additional embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 1, and a $V_L$ including an amino acid sequence at least 80%, 90%, 95%, 96%, 97%, 98%, or 99% identical to the amino acid sequence set forth as SEQ ID NO: 2, and can specifically bind to EBOV GP and neutralize EBOV.

In additional embodiments, the antibody or antigen binding fragment includes a $V_H$ including the amino acid sequence set forth as one of SEQ ID NO: 1, and can specifically bind to EBOV GP and neutralize EBOV. In more embodiments, the antibody or antigen binding fragment includes a $V_L$ including the amino acid sequence set forth as SEQ ID NO: 2, and can specifically bind to EBOV GP and neutralize EBOV. In some embodiments, the antibody or antigen binding fragment includes a $V_H$ and a $V_L$ including the amino acid sequences set forth as SEQ ID NOs: 1 and 2, respectively, and can specifically bind to EBOV GP and neutralize EBOV.

In some embodiments, the antibody or antigen binding fragment includes a HCDR1, a HCDR2, and a HCDR3, comprising the amino acid sequences set forth as SEQ ID NOs: 32, 33, and 34, respectively, and can specifically bind to EBOV GP and neutralize EBOV. In some embodiments, the antibody or antigen binding fragment includes a LCDR1, a LCDR2, and a LCDR3, comprising the amino acid sequences set forth as SEQ ID NOs: 35, 36, and 37, respectively, and can specifically bind to EBOV GP and neutralize EBOV. In some embodiments, the antibody or antigen binding fragment includes a HCDR1, a HCDR2, a HCDR3, a LCDR1, a LCDR2, and a LCDR3, comprising the amino acid sequences set forth as SEQ ID NOs: 32, 33, 34, 35, 36, and 37, respectively, and can specifically bind to EBOV GP and neutralize EBOV.

In some embodiments, the $V_H$ of any of the disclosed antibodies or antigen binding fragments based on the EVB114 antibody can further include a M31S substitution (kabat numbering) and/or the $V_L$ of any of the disclosed antibodies or antigen binding fragments based on the EVB114 antibody can further include a D30S substitution (kabat numbering), and can specifically bind to EBOV GP and neutralize EBOV. For example, the antibody or antigen binding fragment can includes a HCDR1, a HCDR2, a HCDR3, a LCDR1, a LCDR2, and a LCDR3, comprising the amino acid sequences set forth as SEQ ID NOs: 38, 33, 34, 35, 36, and 37, respectively, SEQ ID NOs: 32, 33, 34, 39, 36, and 37, respectively, or SEQ ID NOs: 38, 33, 34, 39, 36, and 37, respectively, and can specifically bind to EBOV GP and neutralize EBOV. In some embodiments, the antibody or antigen binding fragment can include a $V_H$ comprising the amino acid sequence set forth as SEQ ID NO: 1 further including a M31S substitution, and a $V_L$ comprising the amino acid sequence set forth as SEQ ID NO: 2 further comprising a D30S substitution.

In some embodiments, the $V_H$ of any of the disclosed antibodies or antigen binding fragments based on the EVB114 antibody can comprise a valine residue at kabat position 96 and a serine residue at kabat position 108.

EVB114 Version 2

In some embodiments, the antibody or antigen binding fragment can be based on or derived from the EVB114 version 2 antibody, and can specifically bind to EBOV GP and neutralize EBOV. For example, in some embodiments, the antibody or antigen binding fragment can comprise a $V_H$ comprising a HCDR1, a HCDR2, and a HCDR3 of the $V_H$ set forth as SEQ ID NO: 28 (EVB114 version 2 $V_H$), and a $V_L$ comprising a LCDR1, a LCDR2, and a LCDR3 of the $V_L$ set forth as SEQ ID NO: 29 (EVB114 version 2 $V_L$). In some embodiments, the antibody or antigen binding fragment includes a $V_H$ including a HCDR1, a HCDR2, and a HCDR3 including amino acids 26-33, 51-57, and 96-108 of SEQ ID NO: 28, respectively, and can specifically bind to EBOV GP and neutralize EBOV. In further embodiments, the antibody or antigen binding fragment includes a $V_L$ including a LCDR1, a LCDR2, and a LCDR3 including amino acids 27-32, 50-52, and 89-97 of SEQ ID NO: 29, respectively, and can specifically bind to EBOV GP and neutralize EBOV. In additional embodiments, the antibody or antigen binding fragment includes a $V_H$ including a HCDR1, a HCDR2, and a HCDR3 including amino acids 26-33, 51-57, and 96-108 of SEQ ID NO: 28, respectively, and a $V_L$ including a LCDR1, a LCDR2, and a LCDR3 including amino acids 27-32, 50-52, and 89-97 of SEQ ID NO: 29, respectively, and can specifically bind to EBOV GP and neutralize EBOV.

In some embodiments, the antibody or antigen binding fragment includes a $V_H$ including a
HCDR1, a HCDR2, and a HCDR3 including amino acid sequences at least 90% (such as at least 95%, at least 96%, at least 97%, at least 98%, or at least 99%) identical to amino acids 26-33, 51-57, and 96-108, respectively, of SEQ ID NO: 28, and can specifically bind to EBOV GP and neutralize EBOV. In some embodiments, the antibody or antigen binding fragment includes a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-32, 50-52, and 89-97, respectively, of SEQ ID NO: 29, and can specifically bind to EBOV GP and neutralize EBOV. In additional embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-57, and 96-108, respectively, of SEQ ID NO: 28, and a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-32, 50-52, and 89-97, respectively, of SEQ ID NO: 29, and can specifically bind to EBOV GP and neutralize EBOV.

In some embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 28, and can specifically bind to EBOV GP and neutralize EBOV. In more embodiments, the antibody or antigen binding fragment includes a $V_L$ including an amino acid sequence at least 80%, 90%, 95%, 96%, 97%, 98%, or 99% identical to the amino acid sequence set forth as SEQ ID NO: 29, and can specifically bind to EBOV GP and neutralize EBOV. In additional embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 28, and a $V_L$ including an amino acid sequence at least 80%, 90%, 95%, 96%, 97%, 98%, or 99% identical to the amino acid sequence set forth as SEQ ID NO: 29, and can specifically bind to EBOV GP and neutralize EBOV.

In additional embodiments, the antibody or antigen binding fragment includes a $V_H$ including the amino acid sequence set forth as one of SEQ ID NO: 28, and can specifically bind to EBOV GP and neutralize EBOV. In more embodiments, the antibody or antigen binding fragment includes a $V_L$ including the amino acid sequence set forth as SEQ ID NO: 29, and can specifically bind to EBOV GP and neutralize EBOV. In some embodiments, the antibody or antigen binding fragment includes a $V_H$ and a $V_L$ including the amino acid sequences set forth as SEQ ID NOs: 28 and 29, respectively, and can specifically bind to EBOV GP and neutralize EBOV.

In some embodiments, the antibody or antigen binding fragment includes a HCDR1, a HCDR2, and a HCDR3, comprising the amino acid sequences set forth as SEQ ID NOs: 38, 33, and 34, respectively, and can specifically bind to EBOV GP and neutralize EBOV. In some embodiments, the antibody or antigen binding fragment includes a LCDR1, a LCDR2, and a LCDR3, comprising the amino acid sequences set forth as SEQ ID NOs: 39, 36, and 37, respectively, and can specifically bind to EBOV GP and neutralize EBOV. In some embodiments, the antibody or antigen binding fragment includes a HCDR1, a HCDR2, a HCDR3, a LCDR1, a LCDR2, and a LCDR3, comprising the amino acid sequences set forth as SEQ ID NOs: 38, 33, 34, 39, 36, and 37, respectively, and can specifically bind to EBOV GP and neutralize EBOV.

In some embodiments, the $V_H$ of any of the disclosed antibodies or antigen binding fragments based on the EVB114 version 2 antibody can further include a S31M substitution (kabat numbering) and/or the $V_L$ of any of the disclosed antibodies or antigen binding fragments based on the EVB114 antibody can further include a S30D substitution (kabat numbering). For example, in some embodiments, the antibody or antigen binding fragment can include a $V_H$ comprising the amino acid sequence set forth as SEQ ID NO: 28 further including a S31M substitution, and a $V_L$ comprising the amino acid sequence set forth as SEQ ID NO: 29 further comprising a S30D substitution.

EVB100

In some embodiments, the antibody or antigen binding fragment can be based on or derived from the EVB100 antibody, and can specifically bind to EBOV GP and neutralize EBOV. For example, in some embodiments, the antibody or antigen binding fragment can comprise a $V_H$ comprising a HCDR1, a HCDR2, and a HCDR3 of the $V_H$ set forth as SEQ ID NO: 3 (EVB100 $V_H$), and a $V_L$ comprising a LCDR1, a LCDR2, and a LCDR3 of the $V_L$ set forth as SEQ ID NO: 4 (EVB100 $V_L$). In some embodiments, the antibody or antigen binding fragment includes a $V_H$ including a HCDR1, a HCDR2, and a HCDR3 including amino acids 26-33, 51-57, and 96-114 of SEQ ID NO: 3, respectively, and can specifically bind to EBOV GP and neutralize EBOV. In further embodiments, the antibody or antigen binding fragment includes a $V_L$ including a LCDR1, a LCDR2, and a LCDR3 including amino acids 26-31, 49-51, and 88-95 of SEQ ID NO: 4, respectively, and can specifically bind to EBOV GP and neutralize EBOV. In additional embodiments, the antibody or antigen binding fragment includes a $V_H$ including a HCDR1, a HCDR2, and a HCDR3 including amino acids 26-33, 51-57, and 96-114 of SEQ ID NO: 3, respectively, and a $V_L$ including a LCDR1, a LCDR2, and a LCDR3 including amino acids 26-31, 49-51, and 88-95 of SEQ ID NO: 4, respectively, and can specifically bind to EBOV GP and neutralize EBOV.

In some embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-57, and 96-114, respectively, of SEQ ID NO: 3, and can specifically bind to EBOV GP and neutralize EBOV. In some embodiments, the antibody or antigen binding fragment includes a $V_L$ including a LCDR1, a LCDR2, and a LCDR3 including amino acid sequences at least 90% (such as at least 95%, at least 96%, at least 97%, at least 98%, or at least 99%) identical to amino acids amino acids 26-31, 49-51, and 88-95, respectively, of SEQ ID NO: 4, and can specifically bind to EBOV GP and neutralize EBOV. In additional embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-57, and 96-114, respectively, of SEQ ID NO: 3, and a $V_L$ including a LCDR1, a LCDR2, and a LCDR3 including amino acid sequences at least 90% (such as at least 95%, at least 96%, at least 97%, at least 98%, or at least 99%) identical to amino acids amino acids 26-31, 49-51, and 88-95, respectively, of SEQ ID NO: 4, and can specifically bind to EBOV GP and neutralize EBOV.

In some embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 3, and can specifically bind to EBOV GP and neutralize EBOV. In more embodiments, the antibody or antigen binding fragment includes a $V_L$ including an amino acid sequence at least 80%, 90%, 95%, 96%, 97%, 98%, or 99% identical to the amino acid sequence set forth as SEQ ID NO: 4, and can specifically bind to EBOV GP and neutralize EBOV. In additional embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 3, and a $V_L$ including an amino acid sequence at least 80%, 90%, 95%, 96%, 97%, 98%, or 99% identical to the amino acid sequence set forth as SEQ ID NO: 4, and can specifically bind to EBOV GP and neutralize EBOV.

In additional embodiments, the antibody or antigen binding fragment includes a $V_H$ including the amino acid sequence set forth as one of SEQ ID NO: 3, and can specifically bind to EBOV GP and neutralize EBOV. In more embodiments, the antibody or antigen binding fragment includes a $V_L$ including the amino acid sequence set forth as SEQ ID NO: 4, and can specifically bind to EBOV GP and neutralize EBOV. In some embodiments, the antibody or antigen binding fragment includes a $V_H$ and a $V_L$ including the amino acid sequences set forth as SEQ ID NOs: 3 and 4, respectively, and can specifically bind to EBOV GP and neutralize EBOV.

In some embodiments, the antibody or antigen binding fragment includes a HCDR1, a HCDR2, and a HCDR3, comprising the amino acid sequences set forth as SEQ ID NOs: 40, 41, and 42, respectively, and can specifically bind to EBOV GP and neutralize EBOV. In some embodiments, the antibody or antigen binding fragment includes a LCDR1, a LCDR2, and a LCDR3, comprising the amino acid sequences set forth as SEQ ID NOs: 43, 44, and 45, respectively, and can specifically bind to EBOV GP and neutralize EBOV. In some embodiments, the antibody or antigen binding fragment includes a HCDR1, a HCDR2, a HCDR3, a LCDR1, a LCDR2, and a LCDR3, comprising the amino acid sequences set forth as SEQ ID NOs: 40, 41, 42, 43, 44, and 45, respectively, and can specifically bind to EBOV GP and neutralize EBOV.

In some embodiments, the $V_H$ of any of the disclosed antibodies or antigen binding fragments based on the EVB100 antibody can comprise a valine residue at kabat position 96, a tyrosine residue at kabat position 103 and a serine residue at kabat position 114.

EVB165

In some embodiments, the antibody or antigen binding fragment can be based on or derived from the EVB165 antibody, and can specifically bind to EBOV GP and neutralize EBOV. For example, in some embodiments, the antibody or antigen binding fragment can comprise a $V_H$ comprising a HCDR1, a HCDR2, and a HCDR3 of the $V_H$ set forth as SEQ ID NO: 19 (EVB165 $V_H$), and a $V_L$ comprising a LCDR1, a LCDR2, and a LCDR3 of the $V_L$ set forth as SEQ ID NO: 20 (EVB165 $V_L$). In some embodiments, the antibody or antigen binding fragment includes a $V_H$ including a HCDR1, a HCDR2, and a HCDR3 including amino acids 26-33, 51-58, and 97-117 of SEQ ID NO: 19, respectively, and can specifically bind to EBOV GP and neutralize EBOV. In further embodiments, the antibody or antigen binding fragment includes a $V_L$ including a LCDR1, a LCDR2, and a LCDR3 including amino acids 27-32, 50-52, and 89-97 of SEQ ID NO: 20, respectively, and can specifically bind to EBOV GP and neutralize EBOV. In additional embodiments, the antibody or antigen binding fragment includes a $V_H$ including a HCDR1, a HCDR2, and a HCDR3 including amino acids 26-33, 51-58, and 97-117 of SEQ ID NO: 19, respectively, and a $V_L$ including a LCDR1, a LCDR2, and a LCDR3 including amino acids 27-32, 50-52, and 89-97 of SEQ ID NO: 20, respectively, and can specifically bind to EBOV GP and neutralize EBOV.

In some embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-58, and 97-117, respectively, of SEQ ID NO: 19, and can specifically bind to EBOV GP and neutralize EBOV. In some embodiments, the antibody or antigen binding fragment includes a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-32, 50-52, and 89-97, respectively, of SEQ ID NO: 20, and can specifically bind to EBOV GP and neutralize EBOV. In additional embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-58, and 97-117, respectively, of SEQ ID NO: 19, and a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-32, 50-52, and 89-97, respectively, of SEQ ID NO: 20, and can specifically bind to EBOV GP and neutralize EBOV.

In some embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 19, and can specifically bind to EBOV GP and neutralize EBOV. In more embodiments, the antibody or antigen binding fragment includes a $V_L$ including an amino acid sequence at least 80%, 90%, 95%, 96%, 97%, 98%, or 99% identical to the amino acid sequence set forth as SEQ ID NO: 20, and can specifically bind to EBOV GP and neutralize EBOV. In additional embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 19, and a $V_L$ including an amino acid sequence at least 80%, 90%, 95%, 96%, 97%, 98%, or 99% identical to the amino acid sequence set forth as SEQ ID NO: 20, and can specifically bind to EBOV GP and neutralize EBOV.

In additional embodiments, the antibody or antigen binding fragment includes a $V_H$ including the amino acid sequence set forth as one of SEQ ID NO: 19, and can specifically bind to EBOV GP and neutralize EBOV. In more embodiments, the antibody or antigen binding fragment includes a $V_L$ including the amino acid sequence set forth as SEQ ID NO: 20, and can specifically bind to EBOV GP and neutralize EBOV. In some embodiments, the antibody or antigen binding fragment includes a $V_H$ and a $V_L$ including the amino acid sequences set forth as SEQ ID NOs: 19 and 20, respectively, and can specifically bind to EBOV GP and neutralize EBOV.

In some embodiments, the antibody or antigen binding fragment includes a HCDR1, a HCDR2, and a HCDR3, comprising the amino acid sequences set forth as SEQ ID NOs: 46, 47, and 48, respectively, and can specifically bind to EBOV GP and neutralize EBOV. In some embodiments, the antibody or antigen binding fragment includes a LCDR1, a LCDR2, and a LCDR3, comprising the amino acid sequences set forth as SEQ ID NOs: 49, 36, and 50, respectively, and can specifically bind to EBOV GP and neutralize EBOV. In some embodiments, the antibody or antigen binding fragment includes a HCDR1, a HCDR2, a HCDR3, a LCDR1, a LCDR2, and a LCDR3, comprising the amino acid sequences set forth as SEQ ID NOs: 46, 47, 48, 49, 36, and 50, respectively, and can specifically bind to EBOV GP and neutralize EBOV.

EVB166

In some embodiments, the antibody or antigen binding fragment can be based on or derived from the EVB166 antibody, and can specifically bind to EBOV GP and neutralize EBOV. For example, in some embodiments, the antibody or antigen binding fragment can comprise a $V_H$ comprising a HCDR1, a HCDR2, and a HCDR3 of the $V_H$ set forth as SEQ ID NO: 5 (EVB166 $V_H$), and a $V_L$ comprising a LCDR1, a LCDR2, and a LCDR3 of the $V_L$ set forth as SEQ ID NO: 6 (EVB166 $V_L$). In some embodiments, the antibody or antigen binding fragment includes a $V_H$ including a HCDR1, a HCDR2, and a HCDR3 including amino acids 26-33, 51-58, and 97-112 of SEQ ID NO: 5, respectively, and can specifically bind to EBOV GP and neutralize EBOV. In further embodiments, the antibody or antigen binding fragment includes a $V_L$ including a LCDR1, a LCDR2, and a LCDR3 including amino acids 27-33, 51-53, and 90-98 of SEQ ID NO: 6, respectively, and can specifically bind to EBOV GP and neutralize EBOV. In additional embodiments, the antibody or antigen binding fragment includes a $V_H$ including a HCDR1, a HCDR2, and a HCDR3 including amino acids 26-33, 51-58, and 97-112 of SEQ ID NO: 5, respectively, and a $V_L$ including a LCDR1, a LCDR2, and a LCDR3 including amino acids 27-33, 51-53, and 90-98 of SEQ ID NO: 6, respectively, and can specifically bind to EBOV GP and neutralize EBOV.

In some embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-58, and 97-112, respectively, of SEQ ID NO: 5, and can specifically bind to EBOV GP and neutralize EBOV. In some embodiments, the antibody or antigen binding fragment includes a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-33, 51-53, and 90-98, respectively, of SEQ ID NO: 6, and can specifically bind to EBOV GP and neutralize EBOV. In additional embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-58, and 97-112, respectively, of SEQ ID NO: 5, and a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-33, 51-53, and 90-98, respectively, of SEQ ID NO: 6, and can specifically bind to EBOV GP and neutralize EBOV.

In some embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 5, and can specifically bind to EBOV GP and neutralize EBOV. In more embodiments, the antibody or antigen binding fragment includes a $V_L$ including an amino acid sequence at least 80%, 90%, 95%, 96%, 97%, 98%, or 99% identical to the amino acid sequence set forth as SEQ ID NO: 6, and can specifically bind to EBOV GP and neutralize EBOV. In more embodiments, the antibody or antigen binding fragment includes a $V_L$ including an amino acid sequence at least 80%, 90%, 95%, 96%, 97%, 98%, or 99% identical to the amino acid sequence set forth as SEQ ID NO: 62, and can specifically bind to EBOV GP and neutralize EBOV. In additional embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 5, and a $V_L$ including an amino acid sequence at least 80%, 90%, 95%, 96%, 97%, 98%, or 99% identical to the amino acid sequence set forth as SEQ ID NO: 6, and can specifically bind to EBOV GP and neutralize EBOV. In additional embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 5, and a $V_L$ including an amino acid sequence at least 80%, 90%, 95%, 96%, 97%, 98%, or 99% identical to the amino acid sequence set forth as SEQ ID NO: 62, and can specifically bind to EBOV GP and neutralize EBOV.

In additional embodiments, the antibody or antigen binding fragment includes a $V_H$ including the amino acid sequence set forth as one of SEQ ID NO: 5, and can specifically bind to EBOV GP and neutralize EBOV. In more embodiments, the antibody or antigen binding fragment includes a $V_L$ including the amino acid sequence set forth as SEQ ID NO: 6, and can specifically bind to EBOV GP and neutralize EBOV. In more embodiments, the antibody or antigen binding fragment includes a $V_L$ including the amino acid sequence set forth as SEQ ID NO: 62, and can specifically bind to EBOV GP and neutralize EBOV. In some embodiments, the antibody or antigen binding fragment includes a $V_H$ and a $V_L$ including the amino acid sequences set forth as SEQ ID NOs: 5 and 6, respectively, and can specifically bind to EBOV GP and neutralize EBOV. In some embodiments, the antibody or antigen binding fragment includes a $V_H$ and a $V_L$ including the amino acid sequences set forth as SEQ ID NOs: 5 and 62, respectively, and can specifically bind to EBOV GP and neutralize EBOV.

In some embodiments, the antibody or antigen binding fragment includes a HCDR1, a HCDR2, and a HCDR3, comprising the amino acid sequences set forth as SEQ ID NOs: 51, 52, and 53, respectively, and can specifically bind to EBOV GP and neutralize EBOV. In some embodiments, the antibody or antigen binding fragment includes a LCDR1, a LCDR2, and a LCDR3, comprising the amino acid sequences set forth as SEQ ID NOs: 54, 55, and 56, respectively, and can specifically bind to EBOV GP and neutralize EBOV. In some embodiments, the antibody or antigen binding fragment includes a HCDR1, a HCDR2, a HCDR3, a LCDR1, a LCDR2, and a LCDR3, comprising the amino acid sequences set forth as SEQ ID NOs: 51, 52, 53, 54, 55, and 56, respectively, and can specifically bind to EBOV GP and neutralize EBOV.

EVB167

In some embodiments, the antibody or antigen binding fragment can be based on or derived from the EVB167 antibody, and can specifically bind to EBOV GP and neutralize EBOV. For example, in some embodiments, the antibody or antigen binding fragment can comprise a $V_H$ comprising a HCDR1, a HCDR2, and a HCDR3 of the $V_H$ set forth as SEQ ID NO: 23 (EVB167 $V_H$), and a $V_L$ comprising a LCDR1, a LCDR2, and a LCDR3 of the $V_L$ set forth as SEQ ID NO: 24 (EVB167 $V_L$). In some embodiments, the antibody or antigen binding fragment includes a $V_H$ including a HCDR1, a HCDR2, and a HCDR3 including amino acids 26-33, 51-58, and 97-102 of SEQ ID NO: 23, respectively, and can specifically bind to EBOV GP and neutralize EBOV. In further embodiments, the antibody or antigen binding fragment includes a $V_L$ including a LCDR1, a LCDR2, and a LCDR3 including amino acids 27-33, 51-53, and 90-101 of SEQ ID NO: 24, respectively, and can specifically bind to EBOV GP and neutralize EBOV. In additional embodiments, the antibody or antigen binding fragment includes a $V_H$ including a HCDR1, a HCDR2, and a HCDR3 including amino acids 26-33, 51-58, and 97-102 of SEQ ID NO: 23, respectively, and a $V_L$ including a LCDR1, a LCDR2, and a LCDR3 including amino acids 27-33, 51-53, and 90-101 of SEQ ID NO: 24, respectively, and can specifically bind to EBOV GP and neutralize EBOV.

In some embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-58, and 97-102, respectively, of SEQ ID NO: 23, and can specifically bind to EBOV GP and neutralize EBOV. In some embodiments, the antibody or antigen binding fragment includes a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-33, 51-53, and 90-101, respectively, of SEQ ID NO: 24, and can specifically bind to EBOV GP and neutralize EBOV. In additional embodiments, the antibody or antigen binding fragment includes a $V_H$ including a HCDR1, a HCDR2, and a HCDR3 including amino acid sequences at least 90% (such as at least 95%, at least 96%, at least 97%, at least 98%, or at least 99%) identical to amino acids 26-33, 51-58, and 97-102, respectively, of SEQ ID NO: 23, and a $V_L$ including a LCDR1, a LCDR2, and a LCDR3 including amino acid sequences at least 90% (such as at least 95%, at least 96%, at least 97%, at least 98%, or at least 99%) identical to amino acids amino acids 27-33, 51-53, and 90-101, respectively, of SEQ ID NO: 24, and can specifically bind to EBOV GP and neutralize EBOV.

In some embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 23, and can specifically bind to EBOV GP and neutralize EBOV. In more embodiments, the antibody or antigen binding fragment includes a $V_L$ including an amino acid sequence at least 80%, 90%, 95%, 96%, 97%, 98%, or 99% identical to the amino acid sequence set forth as SEQ ID NO: 24, and can specifically bind to EBOV GP and neutralize EBOV. In additional embodiments, the antibody or antigen binding fragment includes a $V_H$ including an amino acid sequence at least 80%, 90%, 95%, 96%, 97%, 98%, or 99% identical to the amino acid sequence set forth as SEQ ID NO: 23, and a $V_L$ including an amino acid sequence at least 80%, 90%, 95%, 96%, 97%, 98%, or 99% identical to the amino acid sequence set forth as SEQ ID NO: 24, and can specifically bind to EBOV GP and neutralize EBOV.

In additional embodiments, the antibody or antigen binding fragment includes a $V_H$ including the amino acid sequence set forth as one of SEQ ID NO: 23, and can specifically bind to EBOV GP and neutralize EBOV. In more embodiments, the antibody or antigen binding fragment includes a $V_L$ including the amino acid sequence set forth as SEQ ID NO: 24, and can specifically bind to EBOV GP and neutralize EBOV. In some embodiments, the antibody or antigen binding fragment includes a $V_H$ and a $V_L$ including the amino acid sequences set forth as SEQ ID NOs: 23 and 24, respectively, and can specifically bind to EBOV GP and neutralize EBOV.

In some embodiments, the antibody or antigen binding fragment includes a HCDR1, a HCDR2, and a HCDR3, comprising the amino acid sequences set forth as SEQ ID NOs: 57, 58, and 59, respectively, and can specifically bind to EBOV GP and neutralize EBOV. In some embodiments, the antibody or antigen binding fragment includes a LCDR1, a LCDR2, and a LCDR3, comprising the amino acid sequences set forth as SEQ ID NOs: 60, 55, and 61, respectively, and can specifically bind to EBOV GP and neutralize EBOV. In some embodiments, the antibody or antigen binding fragment includes a HCDR1, a HCDR2, a HCDR3, a LCDR1, a LCDR2, and a LCDR3, comprising the amino acid sequences set forth as SEQ ID NOs: 57, 58, 59, 60, 55, and 61, respectively, and can specifically bind to EBOV GP and neutralize EBOV.

1. Additional Description of Antibodies and Antigen Binding Fragments

The antibody or antigen binding fragment can be a human antibody or fragment thereof. Chimeric antibodies are also provided. The antibody or antigen binding fragment can include any suitable framework region, such as (but not limited to) a human framework region. Human framework regions, and mutations that can be made in a human antibody framework regions, are known in the art (see, for example, in U.S. Pat. No. 5,585,089, which is incorporated herein by reference). Alternatively, a heterologous framework region, such as, but not limited to a mouse or monkey framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

The antibody can be of any isotype. The antibody can be, for example, an IgM or an IgG antibody, such as IgG$_1$, IgG$_2$, IgG$_3$, or IgG$_4$. The class of an antibody that specifically binds EBOV GP can be switched with another. In one aspect, a nucleic acid molecule encoding V$_L$ or V$_H$ is isolated using methods well-known in the art, such that it does not include any nucleic acid sequences encoding the constant region of the light or heavy chain, respectively. A nucleic acid molecule encoding V$_L$ or V$_H$ is then operatively linked to a nucleic acid sequence encoding a C$_L$ or C$_H$ from a different class of immunoglobulin molecule. This can be achieved using a vector or nucleic acid molecule that comprises a C$_L$ or C$_H$ chain, as known in the art. For example, an antibody that specifically binds EBOV GP, that was originally IgM may be class switched to an IgG. Class switching can be used to convert one IgG subclass to another, such as from IgG$_1$ to IgG$_2$, IgG$_3$, or IgG$_4$.

In some examples, the disclosed antibodies are oligomers of antibodies, such as dimers, trimers, tetramers, pentamers, hexamers, septamers, octomers and so on.

(a) Binding Affinity

In several embodiments, the antibody or antigen binding fragment can specifically bind EBOV GP with an affinity (e.g., measured by K$_d$) of no more than $1.0 \times 10^{-8}$M, no more than $5.0 \times 10^{-8}$M, no more than $1.0 \times 10^{-11}$ M, no more than $5.0 \times 10^{-9}$M, no more than $1.0 \times 10^{-10}$ M, no more than $5.0 \times 10^{-10}$ M, or no more than $1.0 \times 10^{-11}$M. K$_d$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881, 1999, which is incorporated by reference herein in its entirety). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

In another assay, K$_d$ can be measured using surface plasmon resonance assays using a BIACORE®-2000 or a BIACORE®-3000 (BIAcore, Inc., Piscataway, N.J.) at 25° C. with immobilized antigen CMS chips at ~10 response units (RU). Briefly, carboxymethylated dextran biosensor chips (CMS, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates (k$_{on}$) and dissociation rates (k$_{off}$) are calculated using a simple one-to-one Langmuir binding model (BIACORE® Evaluation Software version 3.2) by simultaneously fitting the association and dissociation sensorgrams. The equilibrium dissociation constant (K$_d$) is calculated as the ratio k$_{off}$/k$_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

(b) Neutralization

In several embodiments, the antibodies and antigen binding fragments disclosed herein can neutralize EBOV infection by at least two, at least three, at least four, or at least five strains of EBOV, such as the Bundibugyo (BDBV), Reston (RESTV), Sudan (SUDV), Tai Forest (TAFV), and Zaire (ZEBOV), with an IC50 of less than 50 µg/ml. In more embodiments, the antibodies and antigen binding fragments disclosed herein can neutralize EBOV infection by at least two, at least three, at least four, or at least five strains of EBOV, such as the BDBV, RESTV, SUDV, TAFV, and ZEBOV, with an IC50 of less than 10 µg/ml. In several embodiments the antibodies and antigen binding fragments disclosed herein can neutralize infection by ZEBOV, with an IC50 of less than 50 µg/ml or less than 10 µg/ml. Exemplary methods of assaying EBOV neutralization are provided in the Examples. In some embodiments, neutralization assays can be performed using a single-round EBOV GP-pseudoviruses infection of 293-T cells. In some embodiments, methods to assay for neutralization activity includes a single-cycle infection assay as described in Martin et al. (2003) *Nature Biotechnology* 21:71-76. In this assay, the level of viral activity is measured via a selectable marker whose activity is reflective of the amount of viable virus in the sample, and the IC$_{50}$ is determined.

(c) Multispecific Antibodies

In some embodiments, the antibody or antigen binding fragment is included on a multispecific antibody, such as a bi-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack, *J. Immunol.*, 158:3965-3970, 1997; Mack, *PNAS*, 92:7021-7025, 1995; Kufer, *Cancer Immunol. Immunother.*, 45:193-197, 1997; Loffler, *Blood*, 95:2098-2103, 2000; and Bruhl, *J. Immunol.*, 166:2420-2426, 2001. Production of bispecific Fab-scFv ("bibody") molecules are described, for example, in Schoonjans et al. (*J. Immunol.* 165:7050-57, 2000) and Willems et al. (*J Chromatogr B Analyt Technol Biomed Life Sci.* 786:161-76, 2003). For bibodies, a scFv molecule can be fused to one of the VL-CL (L) or VH-CH1 chains, e.g., to produce a bibody one scFv is fused to the C-term of a Fab chain.

(d) Fragments

Antigen binding fragments are encompassed by the present disclosure, such as Fab, F(ab')$_2$, and Fv which include a heavy chain and light chain variable region and specifically bind EBOV GP. These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the $V_H$ and $V_L$ expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule. A scFv is a fusion protein in which a $V_L$ of an immunoglobulin and a $V_H$ of an immunoglobulin are bound by a linker (see, e.g., Ahmad et al., Clin. Dev. Immunol., 2012, doi:10.1155/2012/980250; Marbry, IDrugs, 13:543-549, 2010). The intramolecular orientation of the $V_H$-domain and the $V_L$-domain in a scFv, is not decisive for the provided antibodies (e.g., for the provided multispecific antibodies). Thus, scFvs with both possible arrangements ($V_H$-domain-linker domain-$V_L$-domain; $V_L$-domain-linker domain-$V_H$-domain) may be used.

(6) A dimer of a single chain antibody (scFV$_2$), defined as a dimer of a scFV. This has also been termed a "miniantibody."

Methods of making these fragments are known in the art (see for example, Harlow and Lane, *Antibodies: A Laboratory Manual*, 2$^{nd}$, Cold Spring Harbor Laboratory, New York, 2013).

In some embodiments, the antigen binding fragment can be an Fv antibody, which is typically about 25 kDa and contain a complete antigen-binding site with three CDRs per each heavy chain and each light chain. To produce Fv antibodies, the $V_H$ and the $V_L$ can be expressed from two individual nucleic acid constructs in a host cell.

If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the $V_H$ and the $V_L$ are chemically linked by disulfide bonds.

In an additional example, the Fv fragments comprise $V_H$ and $V_L$ chains connected by a peptide linker. These single-chain antigen binding proteins (scFv) are prepared by constructing a nucleic acid molecule encoding the $V_H$ and $V_L$ domains connected by an oligonucleotide. The nucleic acid molecule is inserted into an expression vector, which is subsequently introduced into a host cell such as a mammalian cell. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; Ahmad et al., *Clin. Dev. Immunol.*, 2012, doi:10.1155/2012/980250; Marbry, *IDrugs*, 13:543-549, 2010). Dimers of a single chain antibody (scFV$_2$), are also contemplated.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Antigen binding single $V_H$ domains, called domain antibodies (dAb), have also been identified from a library of murine $V_H$ genes amplified from genomic DNA of immunized mice (Ward et al. *Nature* 341:544-546, 1989). Human single immunoglobulin variable domain polypeptides capable of binding antigen with high affinity have also been described (see, for example, PCT Publication Nos. WO 2005/035572 and WO 2003/002609). The CDRs disclosed herein can also be included in a dAb.

In some embodiments, one or more of the heavy and/or light chain complementarity determining regions (CDRs) from a disclosed antibody (such as the EVB100, EVB114, or EVB166 antibody) is expressed on the surface of another protein, such as a scaffold protein. The expression of domains of antibodies on the surface of a scaffolding protein are known in the art (see e.g. Liu et al., *J. Virology* 85(17): 8467-8476, 2011). Such expression creates a chimeric protein that retains the binding for EBOV GP. In some specific embodiments, one or more of the heavy chain CDRs is grafted onto a scaffold protein, such as one or more of heavy chain CDR1, CDR2, and/or CDR3. One or more CDRs can also be included in a diabody or another type of single chain antibody molecule.

(e) Additional Antibodies that Bind to the EVB114, EVB100, EVB165, EVB166, or EVB167 Epitope on EBOV GP.

Also included are antibodies that bind to the same epitope on EBOV GP to which the EVB114, EVB100, EVB165, EVB166, or EVB167 antibody binds. Antibodies that bind to such an epitope can be identified based on their ability to cross-compete (for example, to competitively inhibit the binding of, in a statistically significant manner) with the EVB114, EVB100, EVB165, EVB166, or EVB167 antibodies provided herein in EBOV GP binding assays (such as those described in the Examples). An antibody "competes" for binding when the competing antibody inhibits EBOV GP binding of the EVB114, EVB100, EVB165, EVB166, or EVB167 antibody by more than 50%, in the presence of competing antibody concentrations higher than $10^6 \times K_D$ of the competing antibody. In a certain embodiment, the antibody that binds to the same epitope on EBOV GP as the EVB114, EVB100, EVB165, EVB166, or EVB167 antibody is a human monoclonal antibody. Human antibodies that bind to the same epitope on EBOV GP to which the EVB114, EVB100, EVB165, EVB166, or EVB167 antibody binds can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Such antibodies may be prepared, for example, by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies that bind to the same epitope on EBOV GP to which the EVB114, EVB100, EVB165, EVB166, or EVB167 antibody binds can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3): 185-91 (2005). Human antibodies may also be generated by isolating Fv clone variable domain sequences selected from human-derived phage display libraries. Such variable domain sequences may then be combined with a desired human constant domain.

Antibodies and antigen binding fragments that specifically bind to the same epitope on EBOV GP as EVB114, EVB100, EVB165, EVB166, or EVB167 can also be isolated by screening combinatorial libraries for antibodies with the desired binding characteristics. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

(f) Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, decreased immunogenicity, or improved ADCC or CDC.

The variants typically retain amino acid residues necessary for correct folding and stabilizing between the $V_H$ and the $V_L$ regions, and will retain the charge characteristics of the residues in order to preserve the low pI and low toxicity of the molecules. Amino acid substitutions can be made in the $V_H$ and the $V_L$ regions to increase yield.

In some embodiments, the heavy chain of the antibody includes up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NOs: 1, 3, 5, 19, 23, or 28. In some embodiments, the light chain of the antibody includes up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NOs: 2, 4, 6, 20, 24, or 29.

In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework regions of the heavy chain of the antibody, or the light chain of the antibody, or the heavy and light chains of the antibody, compared to a known framework region, or compared to the framework regions of the EVB114, EVB100, EVB165, EVB166, or EVB167 antibody, and maintain the specific binding activity for EBOV GP.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In certain embodiments of the variant $V_H$ and $V_L$ sequences provided above, each CDR either is unaltered, or contains no more than one, two or three amino acid substitutions.

To increase binding affinity of the antibody, the $V_L$ and $V_H$ segments can be randomly mutated, such as within HCDR3 region or the LCDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the HCDR3 or LCDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for EBOV GP. In particular examples, the $V_H$ amino acid sequence is one of SEQ ID NOs: 1, 3, 5, 19, 23, or 28. In other examples, the $V_L$ amino acid sequence is one of SEQ ID NOs: 2, 4, 6, 20, 24, or 29. Methods of in vitro affinity maturation are known (see, e.g., Chowdhury, *Methods Mol. Biol.* 207:179-196 (2008)), and Hoogenboom et al. in *Methods in Molecular Biology* 178:1-37 (O'Brien et al., ed., Human Press, Totowa, N.J., (2001).)

In certain embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec 13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In several embodiments, the constant region of the antibody includes one or more amino acid substitutions to optimize in vivo half-life of the antibody. The serum half-life of IgG Abs is regulated by the neonatal Fc receptor (FcRn). Thus, in several embodiments, the antibody includes an amino acid substitution that increases binding to the FcRn. Several such substitutions are known, such as substitutions at IgG constant regions T250Q and M428L (see, e.g., Hinton et al., *J Immunol.*, 176:346-356, 2006); M428L and N434S (the "LS" mutation, see, e.g., Zalevsky, et al., *Nature Biotechnology*, 28:157-159, 2010); N434A (see, e.g., Petkova et al., *Int. Immunol.*, 18:1759-1769, 2006); T307A, E380A, and N434A (see, e.g., Petkova et al., *Int. Immunol.*, 18:1759-1769, 2006); and M252Y, S254T, and T256E (see, e.g., Dall'Acqua et al., *J. Biol. Chem.*, 281:23514-23524, 2006). The disclosed antibodies and antigen binding fragments can be linked to a Fc polypeptide including any of the substitutions listed above, for example, the Fc polypeptide can include the M428L and N434S substitutions.

In some embodiments, the constant region of the antibody includes one of more amino acid substitutions to optimize antibody-dependent cell-mediated cytotoxicity (ADCC). ADCC is mediated primarily through a set of closely related Fcγ receptors. In some embodiments, the antibody includes one or more amino acid substitutions that increase binding to FcγRIIIa. Several such substitutions are known, such as substitutions at IgG constant regions S239D and I332E (see, e.g., Lazar et al., *Proc. Natl., Acad. Sci. U.S.A.*, 103:4005-4010, 2006); and S239D, A330L, and I332E (see, e.g., Lazar et al., *Proc. Natl., Acad. Sci. U.S.A.*, 103:4005-4010, 2006).

Combinations of the above substitutions are also included, to generate an IgG constant region with increased binding to FcRn and FcγRIIIa. The combinations increase antibody half-life and ADCC. For example, such combination include antibodies with the following amino acid substitution in the Fc region:

(1) S239D/I332E and T250Q/M428L;
(2) S239D/I332E and M428L/N434S;
(3) S239D/I332E and N434A;
(4) S239D/I332E and T307A/E380A/N434A;
(5) S239D/I332E and M252Y/S254T/T256E;
(6) S239D/A330L/I332E and T250Q/M428L;
(7) S239D/A330L/I332E and M428L/N434S;
(8) S239D/A330L/I332E and N434A;
(9) S239D/A330L/I332E and T307A/E380A/N434A; or
(10) S239D/A330L/I332E and M252Y/S254T/T256E.

In some examples, the antibodies, or an antigen binding fragment thereof is modified such that it is directly cytotoxic to infected cells, or uses natural defenses such as complement, antibody dependent cellular cytotoxicity (ADCC), or phagocytosis by macrophages.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The antibody or antigen binding fragment can be derivatized or linked to another molecule (such as another peptide or protein). In general, the antibody or antigen binding fragment is derivatized such that the binding to EBOV GP is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

B. Conjugates

The monoclonal antibodies and antigen binding fragments that specifically bind to an epitope on EBOV GP can be conjugated to an agent, such as an effector molecule or detectable marker, using any number of means known to those of skill in the art. Both covalent and noncovalent attachment means may be used. One of skill in the art will appreciate that various effector molecules and detectable markers can be used, including (but not limited to) toxins and radioactive agents such as $^{125}$I, $^{32}$P, $^{14}$C, $^{3}$H and $^{35}$S and other labels, target moieties and ligands, etc. The choice of a particular effector molecule or detectable marker depends on the particular target molecule or cell, and the desired biological effect.

The choice of a particular effector molecule or detectable marker depends on the particular target molecule or cell, and the desired biological effect. Thus, for example, the effector molecule can be a cytotoxin that is used to bring about the death of a particular target cell (such as an EBOV infected cell). In other embodiments, the effector molecule can be a cytokine, such as IL-15; conjugates including the cytokine can be used, e.g., to stimulate immune cells locally.

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In view of the large number of methods that have been reported for attaching a variety of radiodiagnostic compounds, radiotherapeutic compounds, labels (such as enzymes or fluorescent molecules), toxins, and other agents to antibodies one skilled in the art will be able to determine a suitable method for attaching a given agent to an antibody or antigen binding fragment or other polypeptide. For example, the antibody or antigen binding fragment can be conjugated with effector molecules such as small molecular weight drugs such as Monomethyl Auristatin E (MMAE), Monomethyl Auristatin F (MMAF), maytansine, maytansine derivatives, including the derivative of maytansine known as DM1 (also known as mertansine), or other agents to make an antibody drug conjugate (ADC). In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

The antibody or antigen binding fragment can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

The antibody or antigen binding fragment can also be conjugated with a radiolabeled amino acid. The radiolabel may be used for both diagnostic and therapeutic purposes. For instance, the radiolabel may be used to detect EBOV GP and EBOV GP expressing cells by x-ray, emission spectra, or other diagnostic techniques. Examples of labels for polypeptides include, but are not limited to, the following radioisotopes or radionucleotides: $^3$ C. Polynucleotides and Expression Nucleic acids molecules (for example, cDNA molecules) encoding the amino acid sequences of antibodies, antigen binding fragments, and conjugates that specifically bind EBOV GP are provided. Nucleic acids encoding these molecules can readily be produced by one of skill in the art, using the amino acid sequences provided herein (such as the CDR sequences and $V_H$ and $V_L$ sequences), sequences available in the art (such as framework or constant region sequences), and the genetic code. In several embodiments, a nucleic acid molecules can encode the $V_H$, the $V_L$, or both the $V_H$ and $V_L$ (for example in a bicistronic expression vector) of a disclosed antibody or antigen binding fragment. In several embodiments, the nucleic acid molecules can be expressed in a host cell (such as a mammalian cell) to produce a disclosed antibody or antigen binding fragment.

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

In a non-limiting example, an isolated nucleic acid molecule encodes the $V_H$ of a disclosed antibody or antigen binding fragment and includes the nucleic acid sequence set forth as any one of SEQ ID NOs: 7, 9, 11, 21, 25, or 30. In a non-limiting example, an isolated nucleic acid molecule encodes the $V_L$ of a disclosed antibody or antigen binding fragment and includes the nucleic acid sequence set forth as any one of SEQ ID NOs: 8, 10, 12, 22, 26, 27, or 31. In a non-limiting example, an isolated nucleic acid molecule encodes the $V_H$ and $V_L$ of a disclosed antibody or antigen binding fragment and includes the nucleic acid sequences set forth as any one of SEQ ID NOs: 7 and 8, respectively, 9 and 11, respectively, 11 and 12, respectively, 21 and 22, respectively, 25 and 26, respectively, 25 and 27, respectively, or 30 and 31, respectively.

Nucleic acid sequences encoding the of antibodies, antigen binding fragments, and conjugates that specifically bind EBOV GP can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques, and instructions sufficient to direct persons of skill through many cloning exercises are known (see, e.g, Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The nucleic acid molecules can be expressed in a recombinantly engineered cell such as bacteria, plant, yeast, insect and mammalian cells. The antibodies, antigen binding fragments, and conjugates can be expressed as individual $V_H$ and/or $V_L$ chain (linked to an effector molecule or detectable marker as needed), or can be expressed as a fusion protein. Methods of expressing and purifying antibodies and antigen binding fragments are known and further described herein (see, e.g., Al-Rubeai (ed), Antibody Expression and Production, Springer Press, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence (Gly$_4$-Ser)$_3$, such that the $V_H$ and $V_L$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed), Antibody Engineering, Vols. 1-2, 2$^{nd}$ Ed., Springer Press, 2010; Harlow and Lane, *Antibodies: A Laboratory Manual*, 2$^{nd}$, Cold Spring Harbor Laboratory, New York, 2013,). Optionally, a cleavage site can be included in a linker, such as a furin cleavage site.

The nucleic acid encoding a $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 20100/093979, incorporated herein by reference. In one example, the immunoadhesin is an IgG$_1$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to EBOV GP and another antigen. The encoded $V_H$ and $V_L$ optionally can include a furin cleavage site between the $V_H$ and $V_L$ domains.

Those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibodies, antigen binding fragments, or conjugates can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For E. coli, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for E. coli and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen biding fragment, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment, the population of cells is a clonal population comprising host cells comprising a recombinant expression vector as described herein Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the antibodies, antigen binding fragments, and conjugates can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin.

Methods for expression of the antibodies, antigen binding fragments, and conjugates, and/or refolding to an appropriate active form, from mammalian cells, and bacteria such as E. coli have been described and are well-known and are applicable to the antibodies disclosed herein. See, e.g., Harlow and Lane, *Antibodies: A Laboratory Manual, 2$^{nd}$*, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

Often, functional heterologous proteins from E. coli or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, In addition to recombinant methods, the antibodies, antigen binding fragments, and/or conjugates can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodiimide) are well known in the art.

D. Methods and Composition

1. Methods of Inhibiting, Treating, and Preventing EBOV Infection and Disease

Methods are disclosed herein for the prevention or treatment of an EBOV infection or EVD, such as a ZEBOV infection, in a subject. Prevention can include inhibition of infection with EBOV. The method can include administering to a subject a therapeutically effective amount of a disclosed antibody, antigen binding fragment, or conjugate that specifically binds EBOV GP, or a nucleic acid encoding such an antibody, antigen binding fragment, conjugate. In some examples, the antibody, antigen binding fragment, conjugate, or nucleic acid molecule, can be used pre-exposure (for example, to prevent or inhibit EBOV infection). In some examples, the antibody, antigen binding fragment, conjugate, or nucleic acid molecule, can be used in post-exposure prophylaxis. In some examples, the antibody, antigen binding fragment, conjugate, or nucleic acid molecule, can be used to eliminate or reduce the viral load of EBOV in a subject infected with EBOV. For example a therapeutically effective amount of an antibody, antigen binding fragment, conjugate, or nucleic acid molecule, can be administered to a subject with an EBOV infection. In some examples the antibody, antigen binding fragment, conjugate, or nucleic acid molecule is modified such that it is directly cytotoxic to infected cells (e.g., by conjugation to a toxin), or uses natural defenses such as complement, antibody dependent cellular cytotoxicity (ADCC), or phagocytosis by macrophages, or can be modified to increase the natural defenses.

The EVD or EBOV infection in the subject does not need to be completely eliminated for the method to be effective. For example, the method can reduce or ameliorate EVD or EBOV infection by a desired amount, for example by at least 10%, at least 20%, at least 50%, at least 60%, at least 70%, at least 80%, at least 90%, at least 95%, at least 98%, or even at least 100% (elimination of detectable EBOV infection or EVD), as compared to EBOV infection or EVD in the absence of the treatment.

In one non-limiting example, the method reduces viral titer in a subject with an EBOV infection. For example, administration of a therapeutically effective amount of a disclosed EBOV GP-specific antibody or antigen binding fragment or conjugate can reduce viral titer by at least 10%, at least 20%, at least 50%, at least 60%, at least 70%, at least 80%, at least 90%, at least 95%, at least 98%, or even at least 100% (elimination of detectable EBOV) in the subject. Methods of determining the EBOV viral titer in the subject are known, and include, for example, obtaining a blood sample from the subject and assaying the sample for EBOV activity.

In several embodiments, administration of a therapeutically effective amount of a disclosed antibody, antigen binding fragment, conjugate, or nucleic acid molecule, results in a reduction in the establishment of EBOV infection and/or reducing subsequent EVD progression in a subject. A reduction in the establishment of EBOV infection and/or a reduction in subsequent EVD progression encompass any statistically significant reduction in EBOV activity.

In several embodiments, the subject can be selected for treatment, for example, a subject at risk of EBOV infection, or known to have an EBOV infection. In some embodiments, a subject can be selected that is at risk of or known to have an infection with a particular strain of EBOV, such as BDBV, RESTV, SUDV, TAFV, or ZEBOV.

In several embodiments, a method of preventing or inhibiting EBOV infection (e.g., ZEBOV infection) of a cell is provided. The method includes contacting the cell with an effective amount of an antibody or antigen binding fragment as disclosed herein. For example the cell can be incubated with the effective amount of the antibody or antigen binding fragment prior to or contemporaneous with incubation with the EBOV. EBOV infection of the cell does not need to be completely eliminated for the method to be effective. For example, a method can reduce EBOV infection by a desired amount, for example by at least 10%, at least 20%, at least 50%, at least 60%, at least 70%, at least 80%, at least 90%, at least 95%, at least 98%, or even at least 100% (elimination of detectable EBOV infected cells), as compared to EBOV infection in the absence of the treatment. In some embodiments, the cell is also contacted with an effective amount of an additional agent, such as anti-viral agent. The cell can be in vivo or in vitro.

Studies in have shown that cocktails of EBOV neutralizing antibodies that target different epitopes of EBOV GP can treat macaques infected with ZEBOV (Qiu et al., *Sci. Transl. Med.*, 4, 138ra81, 2012). Accordingly, in some examples, a subject is further administered one or more additional antibodies that bind EBOV GP and that can neutralize EBOV infection. For example, the subject can be administered a therapeutically effective amount of a set of antibodies including two or more of the EVB100, EVB114 and EVB166 antibodies disclosed herein. The antibodies can be administered as a cocktail (that is, as a single composition including the two or more antibodies), or can be administered in sequence.

In some examples, a subject is administered the DNA encoding the antibody or antigen binding fragments thereof, to provide in vivo antibody production, for example using the cellular machinery of the subject. Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids encoding to an organism. One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof. In some embodiments, a disclosed antibody or antigen binding fragment is expressed in a subject using the pVRC8400 vector (described in Barouch et al., J. Virol, 79, 8828-8834, 2005, which is incorporated by reference herein).

The nucleic acid molecules encoding the disclosed antibodies or antigen binding fragments can be included in a viral vector, for example for expression of the antibody or antigen binding fragment in a host cell, or a subject (such as a subject with or at risk of EBOV infection). A number of viral vectors have been constructed, that can be used to express the disclosed antibodies or antigen binding fragments, such as a retroviral vector, an adenoviral vector, or an adeno-associated virus (AAV) vector. In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

In several embodiments, a subject (such as a human subject with or at risk of HIV-1 infection) can be administered a therapeutically effective amount of an adeno-associated virus (AAV) viral vector that includes one or more nucleic acid molecules encoding a disclosed antibody or antigen binding fragment. The AAV viral vector is designed for expression of the nucleic acid molecules encoding a disclosed antibody or antigen binding fragment, and administration of the therapeutically effective amount of the AAV viral vector to the subject leads to expression of a therapeutically effective amount of the antibody or antigen binding fragment in the subject. Non-limiting examples of AAV viral vectors that can be used to express a disclosed antibody or antigen binding fragment in a subject include those provided in Johnson et al ("Vector-mediated gene transfer engenders long-lived neutralizing activity and protection against SIV infection in monkeys," *Nat. Med.*, 15(8):901-906, 2009) and Gardner et al. ("AAV-expressed eCD4-Ig provides durable protection from multiple SHIV challenges," *Nature*, 519 (7541): 87-91, 2015), each of which is incorporated by reference herein in its entirety.

In one embodiment, a nucleic acid encoding a disclosed antibody, or antigen binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

2. Dosages

A therapeutically effective amount of an EBOV GP-specific antibody, antigen binding fragment, conjugate, or nucleic acid molecule encoding such molecules, will depend upon the severity of the disease and/or infection and the general state of the patient's health. A therapeutically effective amount is that which provides either subjective relief of a symptom(s) or an objectively identifiable improvement as noted by the clinician or other qualified observer. The EBOV GP-specific antibody, antigen binding fragment, conjugate, or nucleic acid molecule encoding such molecules, can be administered in conjunction with another therapeutic agent, either simultaneously or sequentially.

Single or multiple administrations of a composition including a disclosed EBOV GP-specific antibody, antigen binding fragment, conjugate, or nucleic acid molecule encoding such molecules, can be administered depending on the dosage and frequency as required and tolerated by the patient. Compositions including the EBOV GP-specific antibody, antigen binding fragment, conjugate, or nucleic acid molecule encoding such molecules, should provide a sufficient quantity of at least one of the EBOV GP-specific antibodies, antigen binding fragments, conjugates, or nucleic acid molecules to effectively treat the patient. The dosage can be administered once, but may be applied periodically until either a therapeutic result is achieved or until side effects warrant discontinuation of therapy. In one example, a dose of the antibody or antigen binding fragment is infused for thirty minutes every other day. In this example, about one to about ten doses can be administered, such as three or six doses can be administered every other day. In a further example, a continuous infusion is administered for about five to about ten days. The subject can be treated at regular intervals, such as daily, weekly, or monthly, until a desired therapeutic result is achieved. Generally, the dose is sufficient to treat or ameliorate symptoms or signs of disease without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The therapeutically effective dose can be determined from cell culture assays and animal studies.

In certain embodiments, the antibody or antigen binding fragment that specifically binds EBOV GP, or conjugate thereof, or a nucleic acid molecule or vector encoding such a molecule, can be administered at a dose in the range of from about 1 to about 100 mg/kg, such as about 5-50 mg/kg, about 25-75 mg/kg, or about 40-60 mg/kg. In some embodiments, the dosage can be administered at about 1, 2, 3, 4, 5, 6, 7, 8, 9, 10, 20, 30, 40, 50, 60, 70, 80, 90, 100, 150, 200, or 300 mg/kg, or other dose deemed appropriate by the treating physician. Further, the doses described herein can be administered according to the dosing frequency or frequency of administration described herein, including without limitation daily, every other day, 2 or 3 times per week, weekly, every 2 weeks, every 3 weeks, monthly, etc. In some embodiments, the dosage is administered daily beginning at the time of diagnosis with EBOV and until EBOV symptoms are alleviated. Additional treatments, including additional courses of therapy with a disclosed agent can be performed as needed.

3. Modes of Administration

The EBOV GP-specific antibody, antigen binding fragment, conjugate, nucleic acid molecule, or composition, as well as additional agents, can be administered to subjects in various ways, including local and systemic administration, such as, e.g., by injection subcutaneously, intravenously, intra-arterially, intraperitoneally, intramuscularly, intradermally, or intrathecally. In an embodiment, a therapeutic agent is administered by a single subcutaneous, intravenous, intra-arterial, intraperitoneal, intramuscular, intradermal or intrathecal injection once a day. The therapeutic agent can also be administered by direct injection at or near the site of disease.

The therapeutic agent may also be administered orally in the form of microspheres, microcapsules, liposomes (uncharged or charged (e.g., cationic)), polymeric microparticles (e.g., polyamides, polylactide, polyglycolide, poly (lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the therapeutic agent or pharmaceutical composition over a pre-determined period. The osmotic pump or mini-pump can be implanted subcutaneously, or near a target site.

It will be apparent to one skilled in the art that the therapeutic agent or compositions thereof can also be administered by other modes. The therapeutic agent can be administered as pharmaceutical formulations suitable for, e.g., oral (including buccal and sub-lingual), rectal, nasal, topical, pulmonary, vaginal or parenteral (including intramuscular, intraarterial, intrathecal, subcutaneous and intravenous) administration, or in a form suitable for administration by inhalation or insufflation. Depending on the intended mode of administration, the pharmaceutical formulations can be in the form of solid, semi-solid or liquid dosage forms, such as tablets, suppositories, pills, capsules, powders, liquids, suspensions, emulsions, creams, ointments, lotions, and the like. The formulations can be provided in unit dosage form suitable for single administration of a precise dosage. The formulations comprise an effective amount of a therapeutic agent, and one or more pharmaceutically acceptable excipients, carriers and/or diluents, and optionally one or more other biologically active agents.

4. Composition

Compositions are provided that include one or more of the disclosed EBOV GP-specific antibodies, antigen binding fragments, conjugates, or nucleic acid molecules, in a carrier. The compositions are useful, for example, for the treatment or detection of an EBOV infection. The compositions can be prepared in unit dosage forms for administration to a subject. The amount and timing of administration are at the discretion of the treating physician to achieve the desired purposes. The EBOV GP-specific antibody, antigen binding fragment, conjugate, or nucleic acid molecule encoding such molecules can be formulated for systemic or local administration. In one example, the EBOV GP-specific antibody, antigen binding fragment, conjugate, or nucleic acid molecule encoding such molecules, is formulated for parenteral administration, such as intravenous administration.

In some embodiments, the compositions comprise an antibody, antigen binding fragment, or conjugate thereof, in at least 70%, at least 75%, at least 80%, at least 85%, at least 90%, at least 95%, at least 96%, at least 97%, at least 98% or at least 99% purity. In certain embodiments, the compositions contain less than 10%, less than 5%, less than 4%, less than 3%, less than 2%, less than 1% or less than 0.5% of macromolecular contaminants, such as other mammalian (e.g., human) proteins.

The compositions for administration can include a solution of the EBOV GP-specific antibody, antigen binding fragment, conjugate, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as *Remington's Pharmaceutical Science*, 22th ed., Pharmaceutical Press, London, UK (2012). In some embodiments, the composition can be a liquid formulation including one or more antibodies, antigen binding fragments (such as an antibody or antigen binding fragment that specifically binds to EBOV GP), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

The disclosed antibodies, antigen binding fragments, conjugates, and nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antigen binding fragments, can then be added to an infusion bag containing 0.9% sodium chloride, USP, and administered according to standard protocols. Considerable experience is available in the art in the administration of antibody drugs, which have been marketed in the U.S. since the approval of RITUXAN® 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., Colloidal Drug Delivery Systems, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

5. Methods of Detection and Diagnosis

Methods are also provided for the detection of the expression of EBOV GP in vitro or in vivo. In one example, expression of EBOV GP is detected in a biological sample, and can be used to detect EBOV infection as the presence of EBOV in a sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, or administering to a subject, an antibody or antigen binding fragment that specifically binds to EBOV GP, or conjugate there of (e.g. a conjugate including a detectable marker) under conditions sufficient to form an immune complex, and detecting the immune complex (e.g., by detecting a detectable marker conjugated to the antibody or antigen binding fragment.

In several embodiments, a method is provided for detecting EBOV disease and/or an EBOV infection in a subject. The disclosure provides a method for detecting EBOV in a biological sample, wherein the method includes contacting a biological sample from a subject with a disclosed antibody or antigen binding fragment under conditions sufficient for formation of an immune complex, and detecting the immune complex, to detect the EBOV GP in the biological sample. In one example, the detection of EBOV GP in the sample indicates that the subject has an EBOV infection. In another example, the detection of EBOV GP in the sample indicates that the subject has EVD. In another example, detection of EBOV GP in the sample confirms a diagnosis of EVD and/or an EBOV infection in the subject.

In some embodiments, the disclosed antibodies or antigen binding fragments are used to test vaccines. For example to test if a vaccine composition including EBOV GP assumes a conformation including the EBOV GP epitope to which EVB100, EVB114, or EVB166 antibody binds. Thus provided herein is a method for testing a vaccine, wherein the method includes contacting a sample containing the vaccine, such as an EBOV GP immunogen, with a disclosed antibody or antigen binding fragment under conditions sufficient for formation of an immune complex, and detecting the immune complex. Detection of the immune complex confirms that the EBOV GP vaccine includes the epitope to which EVB100, EVB114, or EVB166 antibody, respectively binds. In one example, the detection of the immune complex in the sample indicates that a vaccine component, such as an EBOV GP immunogen assumes a conformation capable of binding the antibody or antigen binding fragment.

In one embodiment, the antibody or antigen binding fragment is directly labeled with a detectable marker. In another embodiment, the antibody that binds EBOV GP (the first antibody) is unlabeled and a second antibody or other molecule that can bind the antibody that binds the first antibody is utilized for detection. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody, antigen binding fragment or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

E. Kits

Kits are also provided. For example, kits for treating a subject with an EBOV infection, or for detecting EBOV GP in a sample or in a subject. The kits will typically include a disclosed EBOV GP-specific antibody, antigen binding fragment, or nucleic acid molecule encoding such molecules, or compositions including such molecules. More than one of the disclosed EBOV GP-specific antibody, antigen binding fragment, conjugate, or nucleic acid molecule encoding such molecules, or compositions including such molecules can be included in the kit.

In one embodiment, the kit is a diagnostic kit and includes an immunoassay. Although the details of the immunoassays may vary with the particular format employed, the method of detecting EBOV GP in a biological sample generally includes the steps of contacting the biological sample with an antibody which specifically reacts, under conditions sufficient to form an immune complex, to EBOV GP. The antibody is allowed to specifically bind under immunologically reactive conditions to form an immune complex, and the presence of the immune complex (bound antibody) is detected directly or indirectly.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, or compositions. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of the antibodies, antigen binding fragments, conjugates, nucleic acid molecules, or compositions included in the kit. The package insert typically includes instructions customarily included in commercial packages of therapeutic products that contain information about the indications, usage, dosage, administration, contraindications and/or warnings concerning the use of such therapeutic products. The instructional materials may be written, in an electronic form or may be visual. The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

III. Examples

The following examples are provided to illustrate particular features of certain embodiments, but the scope of the claims should not be limited to those features exemplified.

Example 1

EBOV GP-Specific Monoclonal Antibodies that Neutralize EBOV Infection

This examples illustrates the isolation and characterization of the EVB100, EVB114, and EVB166 antibodies, which specifically bind to EBOV GP and can neutralize EBOV.

Ebola virus disease (EVD) causes severe illness characterized by rapid onset of fever, vomiting, diarrhea and bleeding diathesis, and was first described in the Democratic Republic of Congo in 1976. The 2014 outbreak in West Africa has affected over 27,000 and claimed at least 11,000 lives. The challenges of a large outbreak and the failure of traditional quarantine and contact tracing measures to control this outbreak highlights the urgency for therapies. The success in nonhuman primates (NHP) of ZMapp, a cocktail of three mouse-human chimeric mAbs derived from immunized mice (Qiu et al., *Clin. Immunol.* 141, 218-27, 2011; Wilson et al., *Science.* 287, 1664-6, 2000), illustrated the potential impact of monoclonal antibody therapies against EVD, and it is currently being evaluated in human trials. To date, efforts to simplify the ZMapp regimen to contain fewer mAbs have not been successful in the macaque EVD model (Qiu et al., *Nature.* 514, 47-53, 2014). Accordingly, mAbs were isolated from human survivors of Ebola virus infection, with the goal of identifying antibodies that confer clinical protection either as single or dual-combination agents.

Figure 1B:
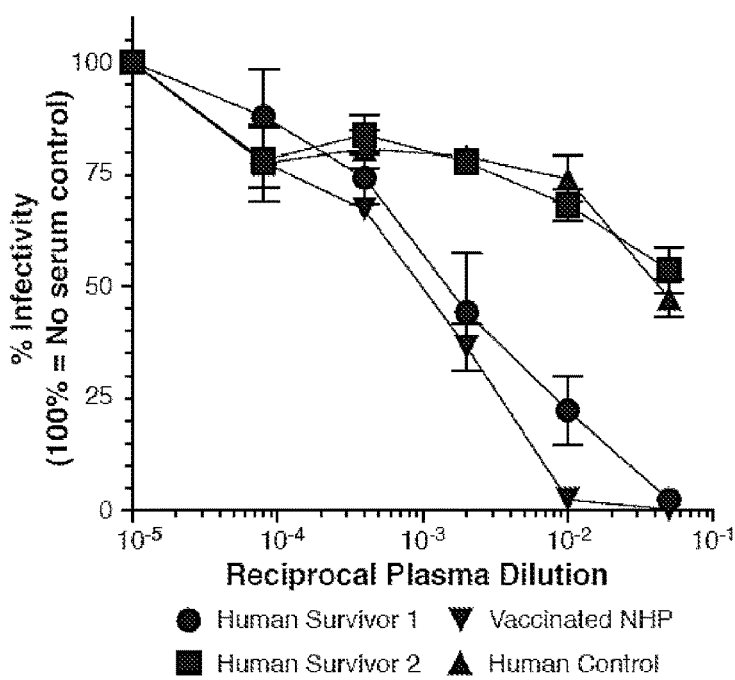

Blood was obtained from two survivors of the 1995 Kikwit EVD outbreak (Muyembe-Tamfum et al., *J. Infect. Dis.* 179 Suppl, S259-S262, 1999) eleven years after infection. These subjects were the sole survivors of a family of 15 people who were infected during the outbreak. At the time of infection, subject 1 (51) was a male 28-year-old who had severe laboratory-confirmed illness and, following recovery, worked for several months in the EVD ward caring for other patients. His sister (S2) was 20-years old and had moderate disease severity that was clinically diagnosed based on contact history and symptoms. To determine if the subjects retained circulating antibodies against Ebola virus (EBOV) glycoprotein (GP), GP-specific antibodies were assessed by ELISA (FIG. 1A). Reciprocal EC90 titers of 2,326 and 275 in the sera of 51 and S2 were observed, respectively. Moreover, the serum from 51, the more severely ill subject, displayed potent virus neutralizing activity (FIG. 1B). The results indicated that these survivors maintained serologic memory against EBOV GP more than a decade following infection, and suggested the potential to clone immunoglobulins with potent neutralizing activity from their memory B cells.

Figure 1C:
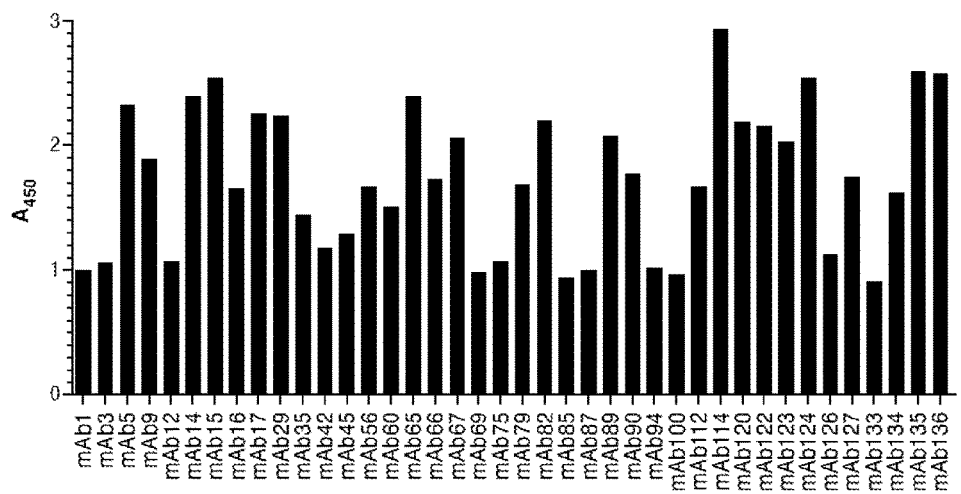
Figure 1D:
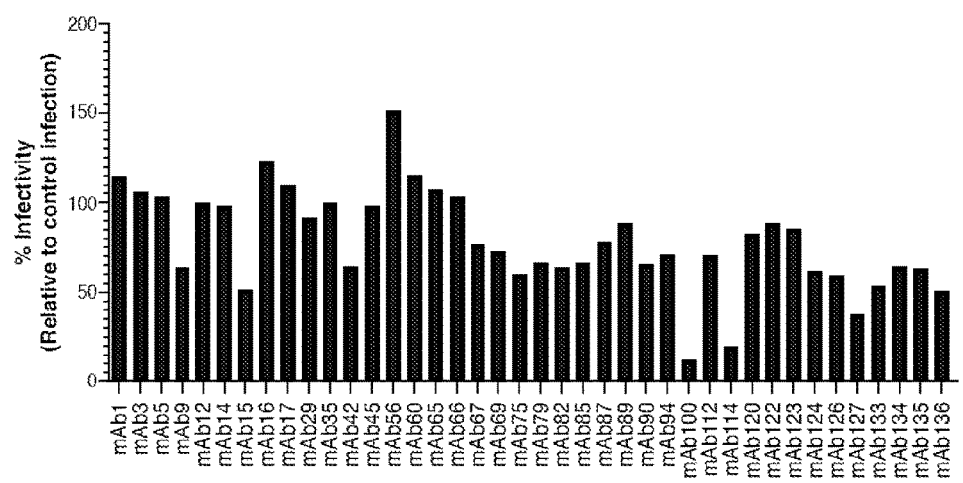

IgG memory B-cells were sorted from S1's peripheral blood mononuclear cells (PBMC), and immortalized individual clones with Epstein-Barr virus (using techniques described in Traggiai et al., *Nat. Med.* 10, 871-875, 2004). Forty immortalized clones whose supernatants displayed a range of GP-binding activity by ELISA were identified (FIG. 1C). Two mAb clones, mAb100 and mAb114 (termed EVB100 and EVB114), expressed antibodies with markedly higher neutralizing activity than all others (FIG. 1D).

A second immortalization yielded 21 clones, from which two additional GP-specific mAb clones, 165 and 166 (termed EVB165 and EVB166), were rescued (see the following table). In the second screening of immortalized memory B-cells from 51, 14 million PBMCs were used to isolate 59,500 IgG memory B cells which were immortalized as in FIGS. 1A-1D. After removal of non-specific binding, 21 culture supernatants were found to specifically bind Ebola GP as measured by ELISA. Shown are ELISA A450 values for undiluted and 1:27 dilutions of the supernatants. Amongst the 21 supernatants, only 2 B cell clones (EVB165, EVB166) were rescued for further analysis.

| Cell line ID | Abs 450 | |
| --- | --- | --- |
| | Und. | 1/27 |
| mAb151 | 1.119 | 0.162 |
| mAb152 | 0.672 | 0.106 |
| mAb153 | 0.854 | 0.131 |
| mAb154 | 2.361 | 0.95 |
| mAb155 | 0.115 | 0.08 |
| mAb156 | 1.111 | 0.161 |
| mAb157 | 2.256 | 0.554 |
| mAb158 | 0.074 | 0.075 |
| mAb159 | 3.298 | 2.529 |
| mAb160 | 1.493 | 0.489 |
| mAb161 | 0.227 | 0.086 |
| mAb162 | 0.083 | 0.074 |
| mAb163 | 3.099 | 1.805 |
| mAb164 | 0.076 | 0.069 |
| EVB165 | 3.171 | 1.722 |
| EVB166 | 2.894 | 2.4 |
| EVB167 | 3.368 | 2.974 |
| mAb168 | 0.507 | 0.114 |
| mAb169 | 0.081 | 0.072 |
| mAb170 | 0.95 | 0.165 |
| mAb171 | 1.998 | 0.895 |

Figures 2F, 2G:
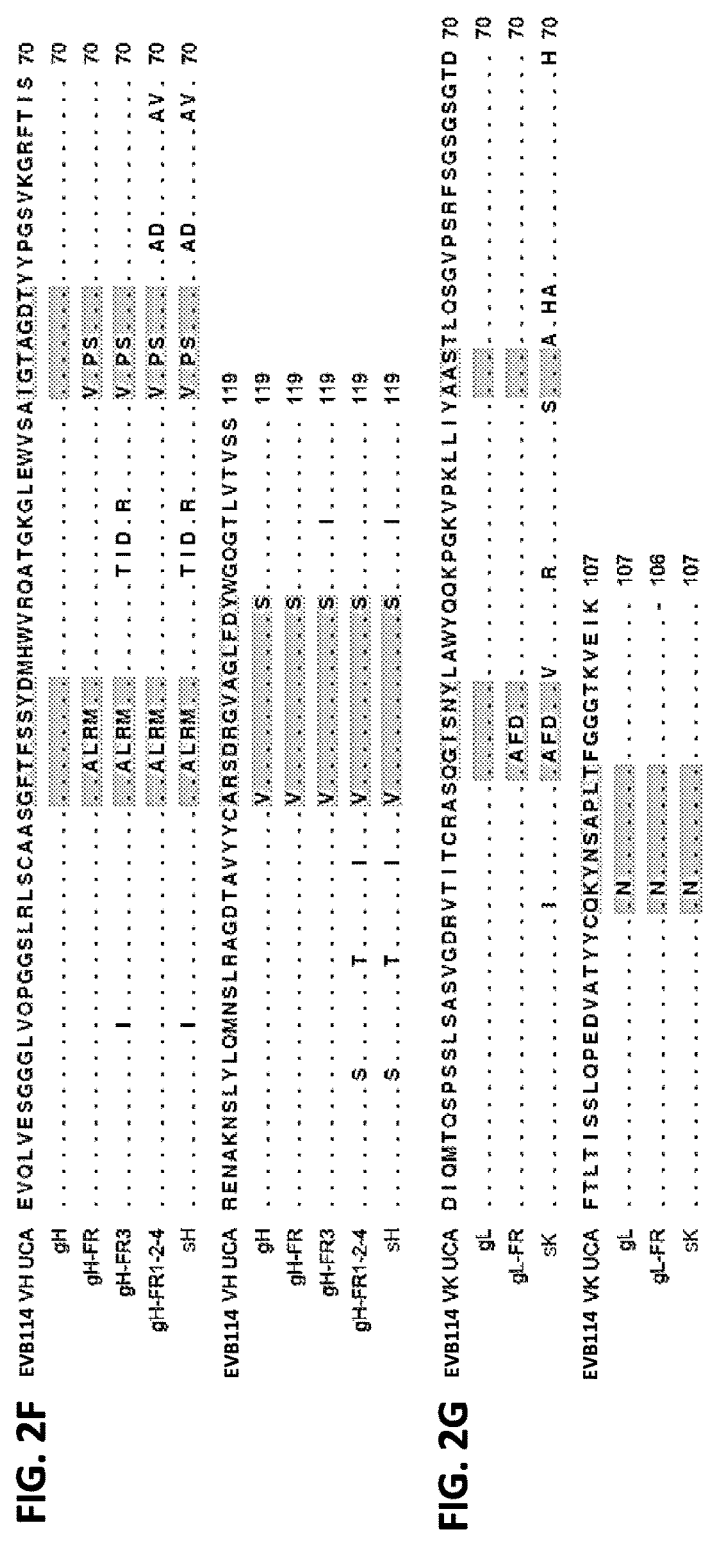
Figure 2H:
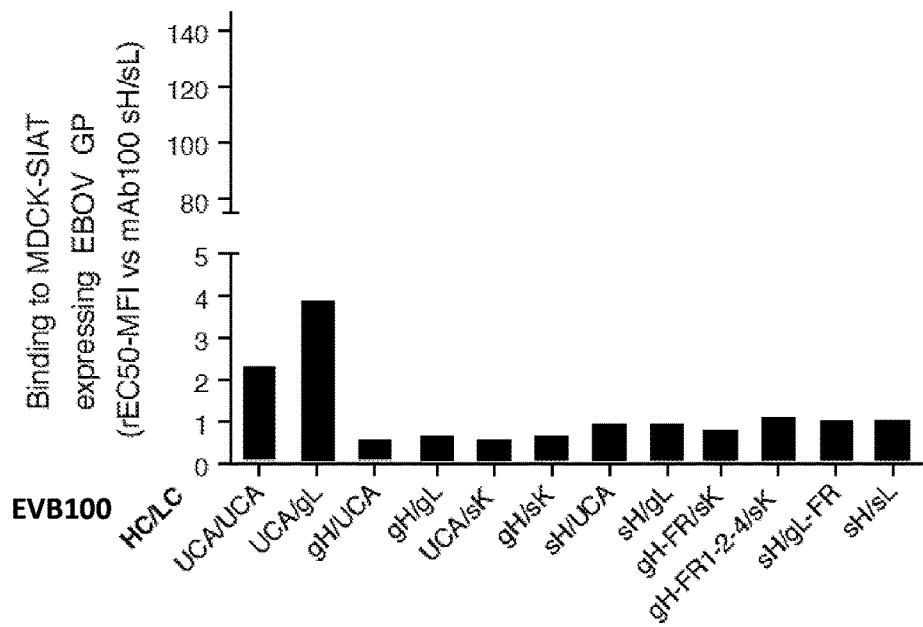

Immunoglobulin sequences were PCR-amplified from the four clones and used to produce EVB100, EVB114, EVB165 and EVB166 by transient transfection. ELISA binding to EBOV GP was assessed and it was observed that one antibody, EVB114, stood apart from the others, displaying nearly 100% higher maximal binding (FIG. 2A). The remaining three antibodies, EVB100, EVB165 and EVB166, exhibited reduced levels of maximal binding compared to EVB114, but were comparable to each other and to KZ52, a prototype human EBOV GP-specific mAb (Maruyama et al., J. Virol. 73, 6024-6030, 1999). EVB114 achieved half maximal binding (EC50) at a concentration of 0.07 µg/mL, which was up to two orders of magnitude lower EC50 than the other mAbs. EVB100 and EVB166 had similar binding profile (0.26 µg/mL, 0.40 µg/mL) while EVB165 bound less well with an EC50>1 Kg/mL.

To test potential functional properties of the mAbs the inhibition of GP mediated entry into HEK293T cells was evaluated in the absence of complement (FIG. 2B) A summary of in vitro neutralization IC data (obtained as described for FIG. 2B) is provided in the following table:

| mAb | IC50 (µg/mL) | 95% CI | IC90 (µg/mL) | 95% CI | IC99 (µg/mL) | 95% CI | n |
|---|---|---|---|---|---|---|---|
| KZ52 | 0.06 | 0.02 to 0.14 | 17.21 | 8.47 to 35.00 | >>1000 | 54,868 | 6 |
| EVB100 | 0.06 | 0.05 to 0.08 | 0.61 | 0.39 to 0.93 | 7.58 | 2.999 to 19.16 | 6 |
| EVB114 | 0.09 | 0.07 to 0.11 | 0.71 | 0.44 to 1.16 | 7.19 | 2.588 to 19.96 | 6 |
| EVB166 | 0.86 | 0.72 to 1.02 | 6.84 | 4.78 to 9.80 | 97.25 | 31.32 to 138.2 | 4 |
| EVB165 | 1.77 | 1.43 to 2.18 | 19.46 | 13.23 to 28.61 | 267.00 | 124.9 to 570.8 | 4 |

Figure 5:
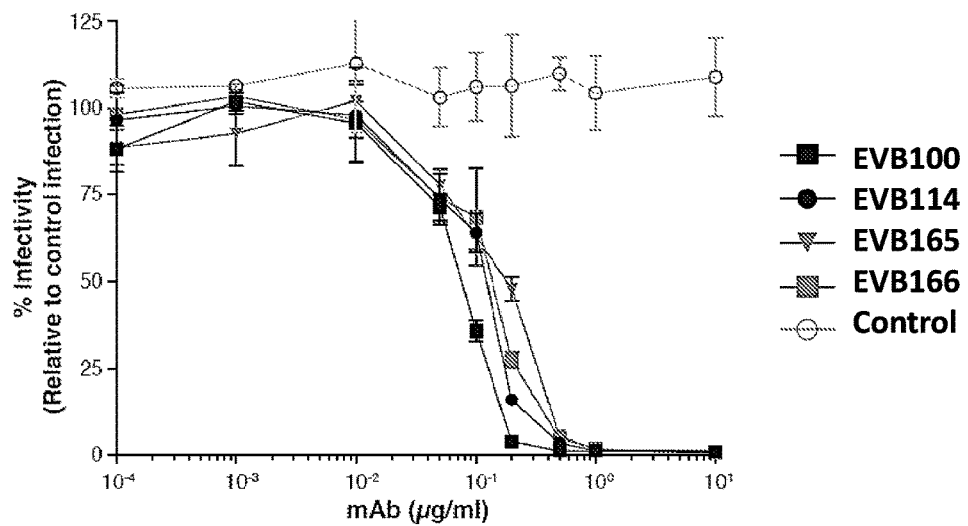
FIG. 5 is a graph illustrating inhibition of EBOV Makona variant by EVB100 and EVB114. Lentivirus particles bearing GPs from EBOV Makona variant were incubated with serially diluted EVB100, EVB114 or isotype control. Infection measured as in FIG. 2B (n=3).
Figure 6:
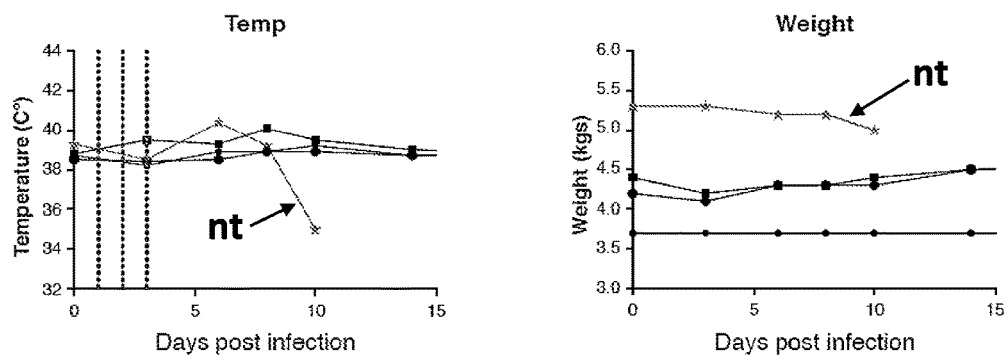
FIGS. 6-8 are a set of graphs showing clinical data from the EBOV challenge study using passive transfer of a combination of EVB114 and EVB100. "nt" is used to indicate data concerning the no treatment (control) animal.
Figure 7A:
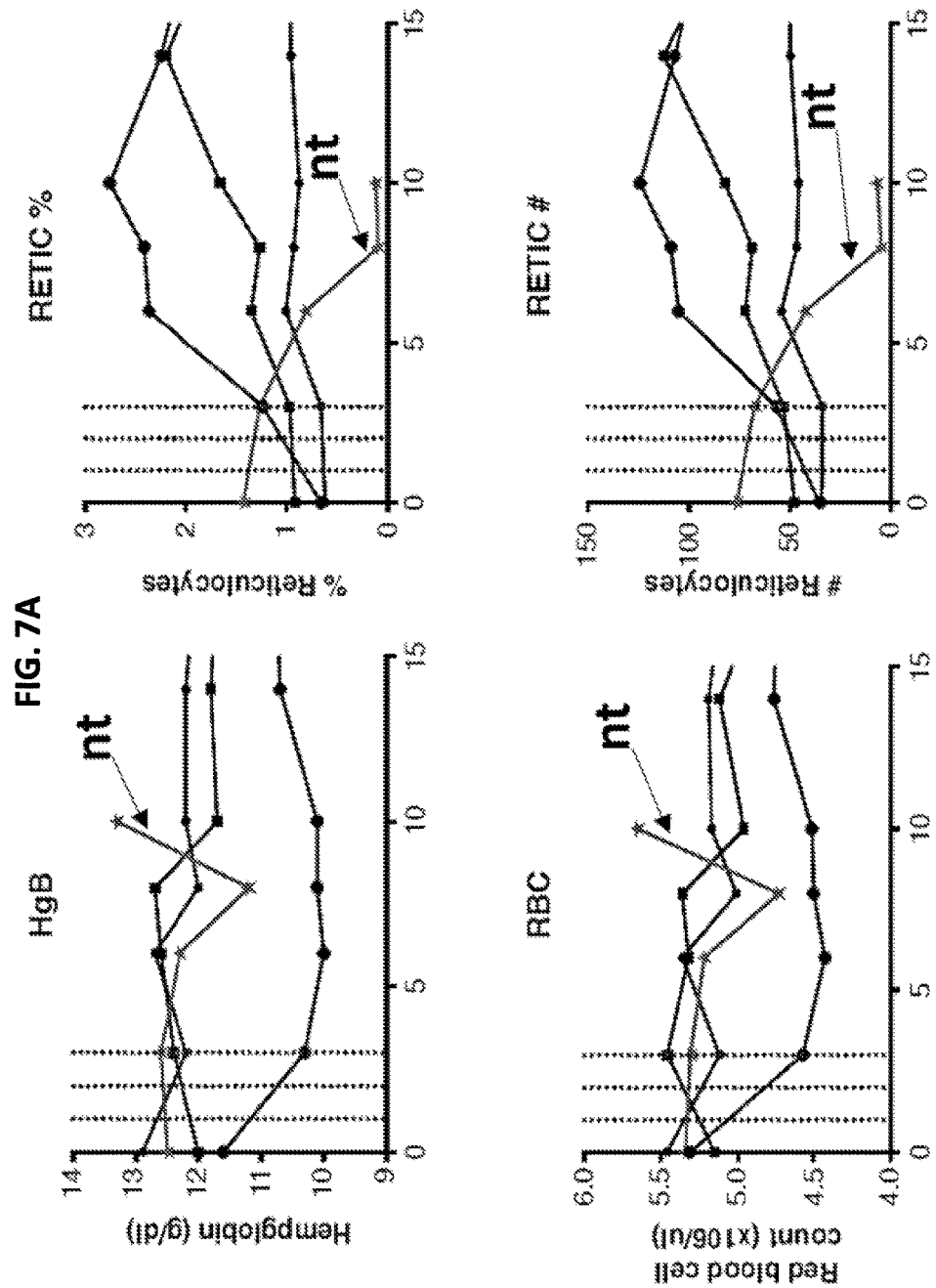
Figure 7B:
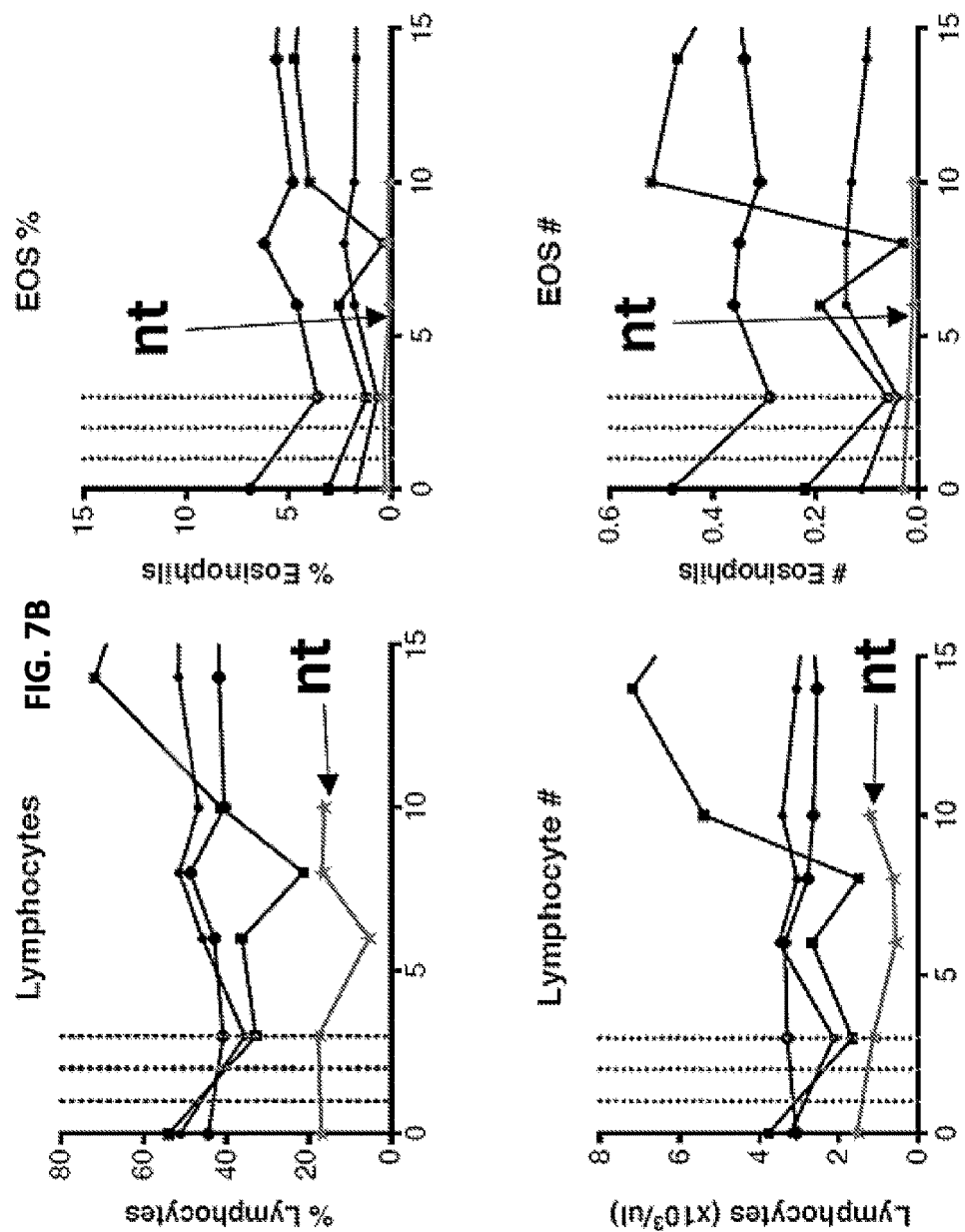
Figure 7C:
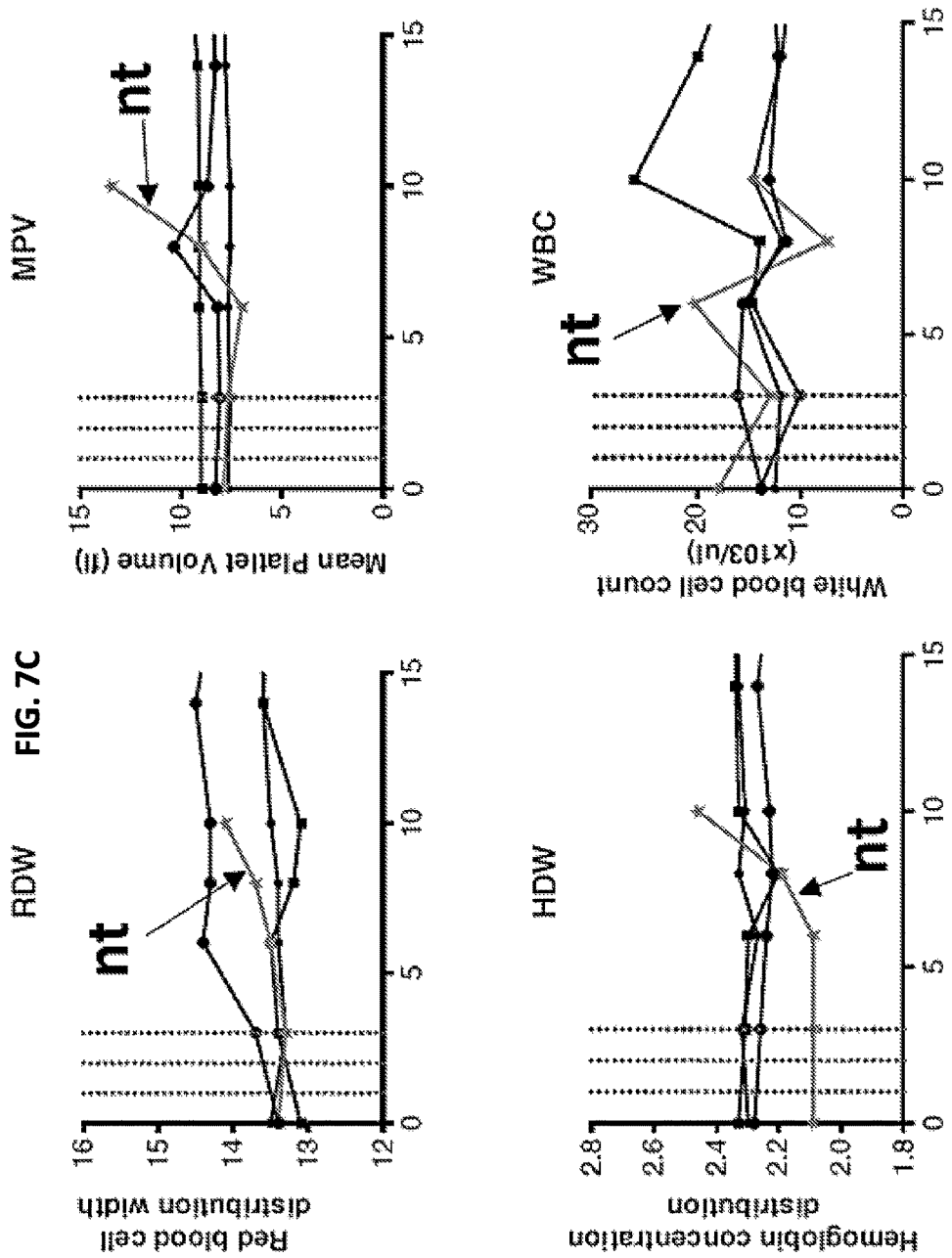
Figure 7D:
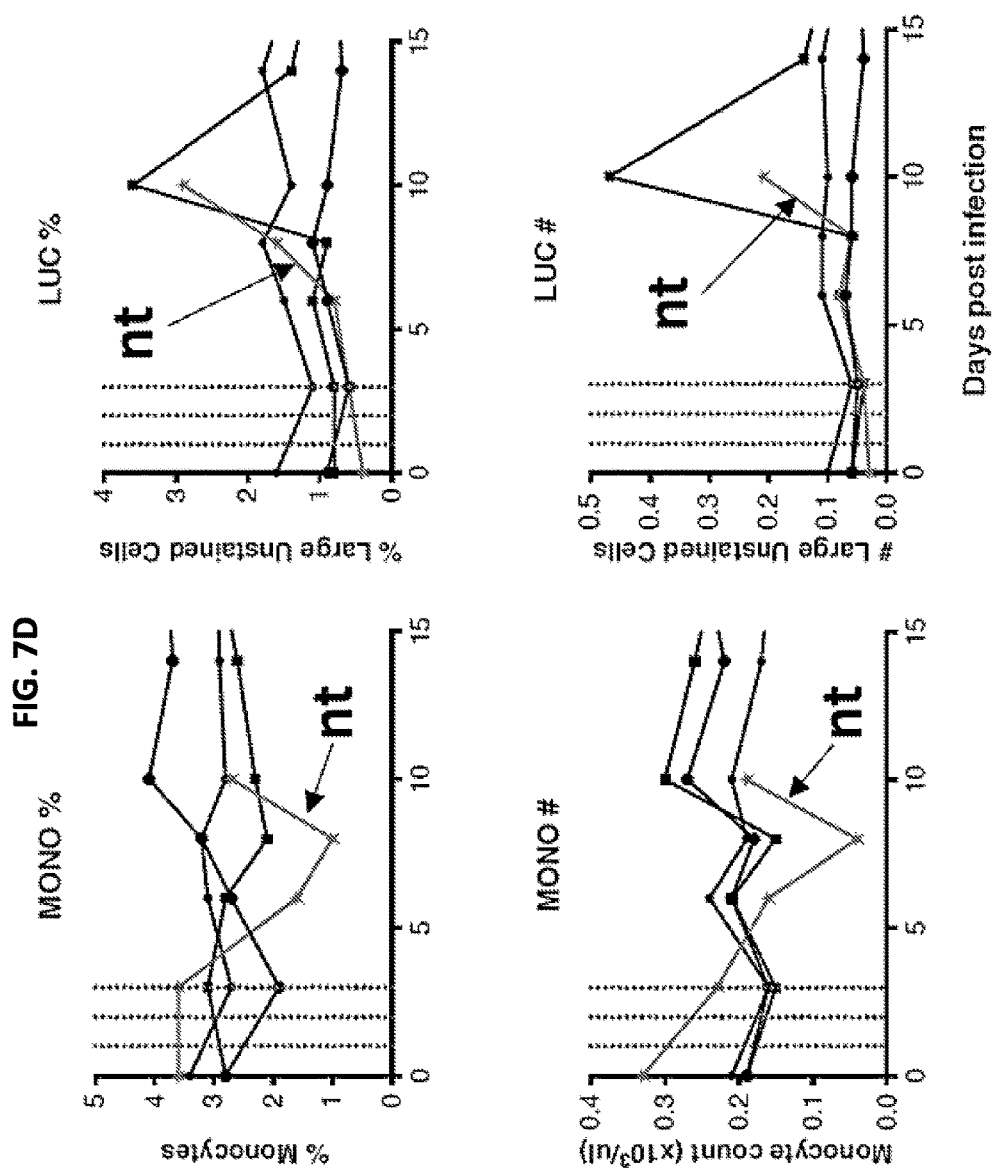
Figure 7E:
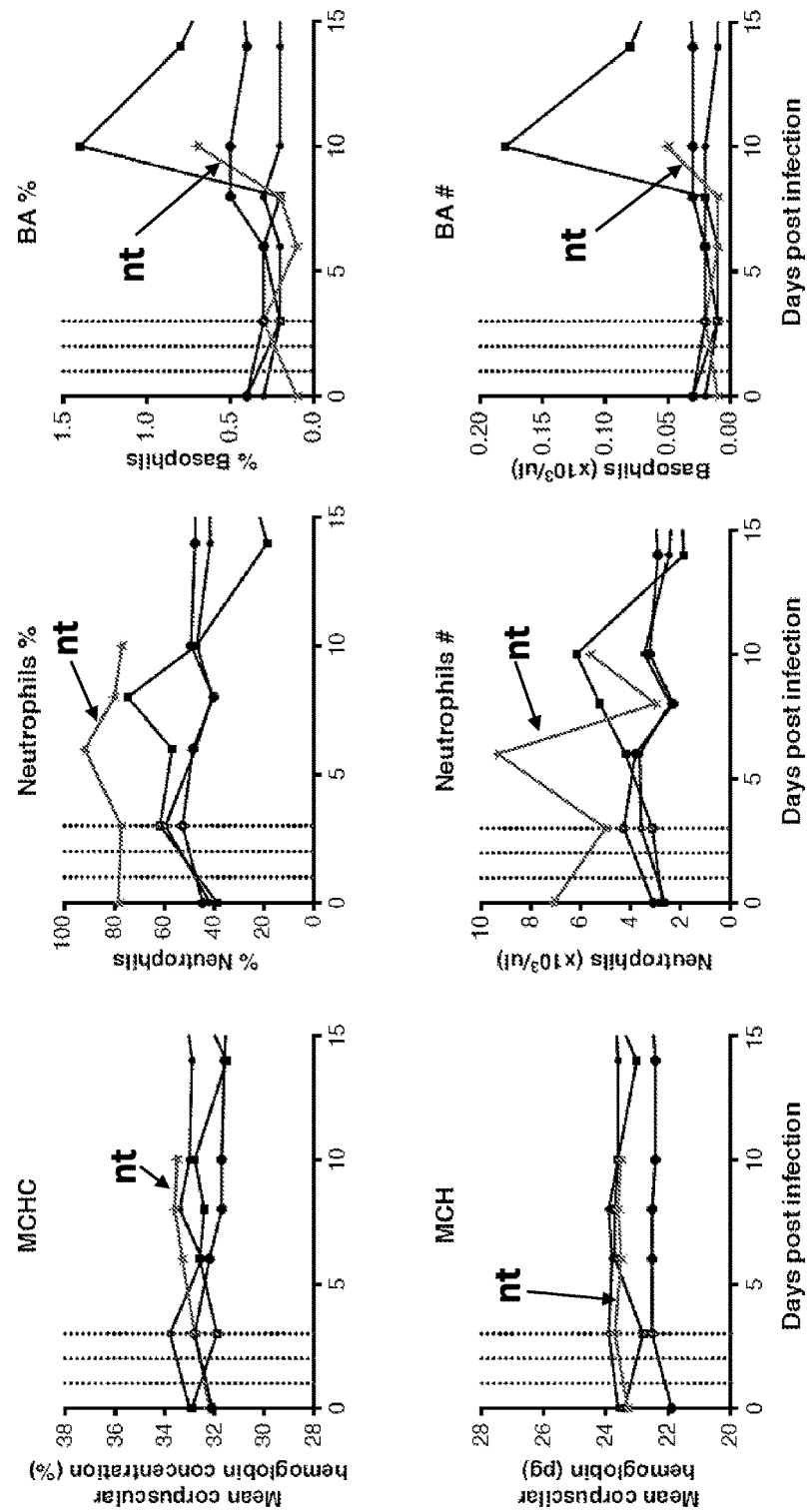
Figure 8A:
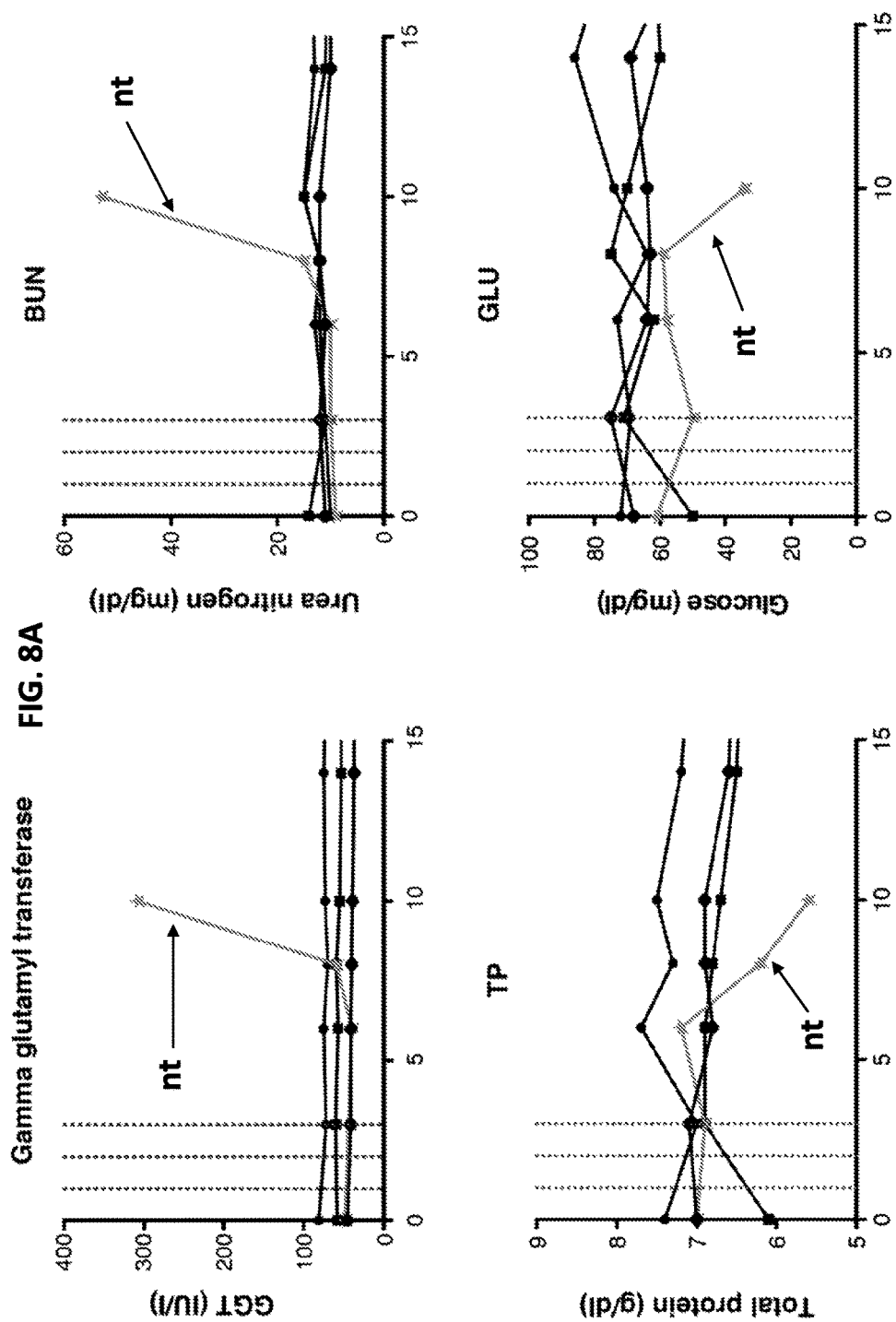
Figure 8B:
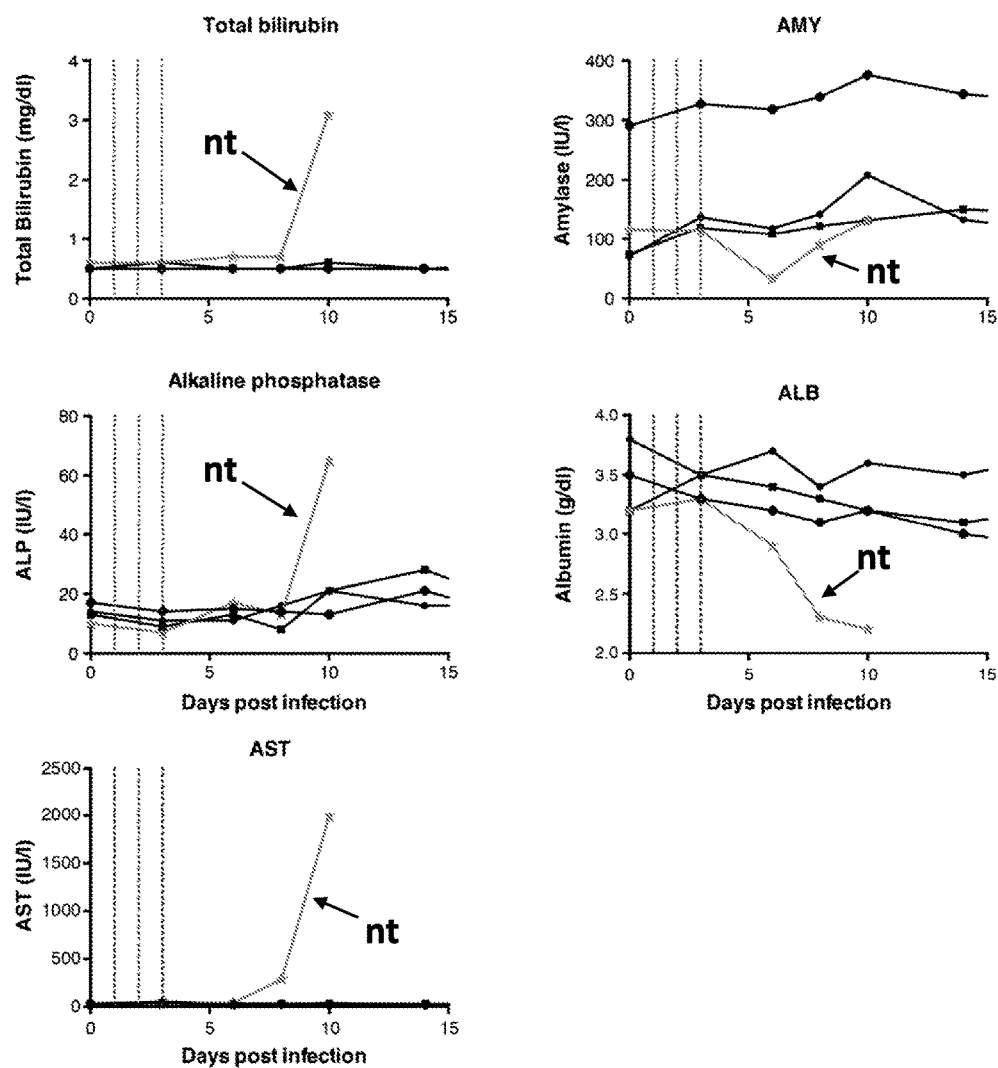
Figure 9:
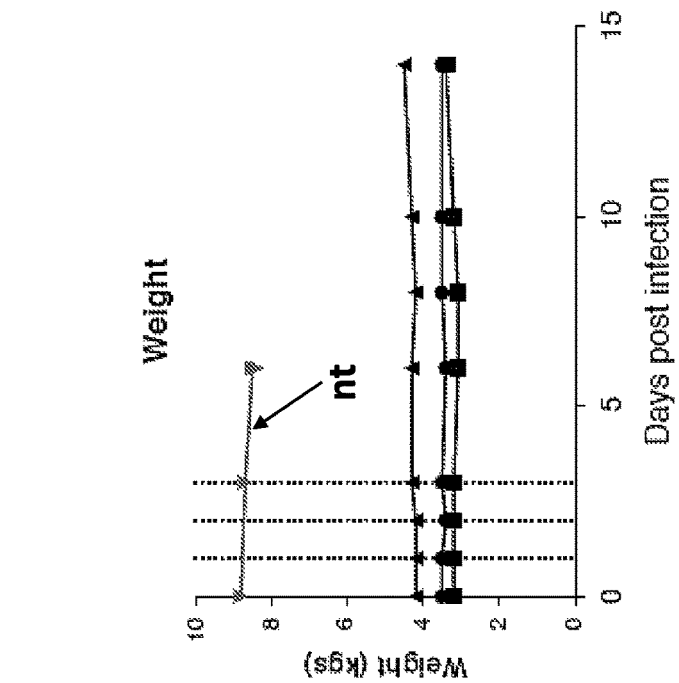
FIGS. 9-11 are a set of graphs showing clinical data from the EBOV challenge study using passive transfer of a monotherapy using EVB114. "nt" is used to indicate data concerning the no treatment (control) animal.
Figure 9:
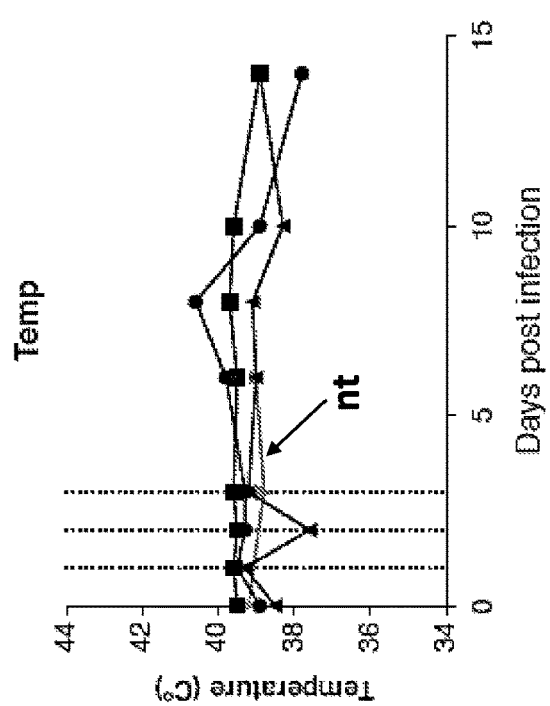
Figure 10A:
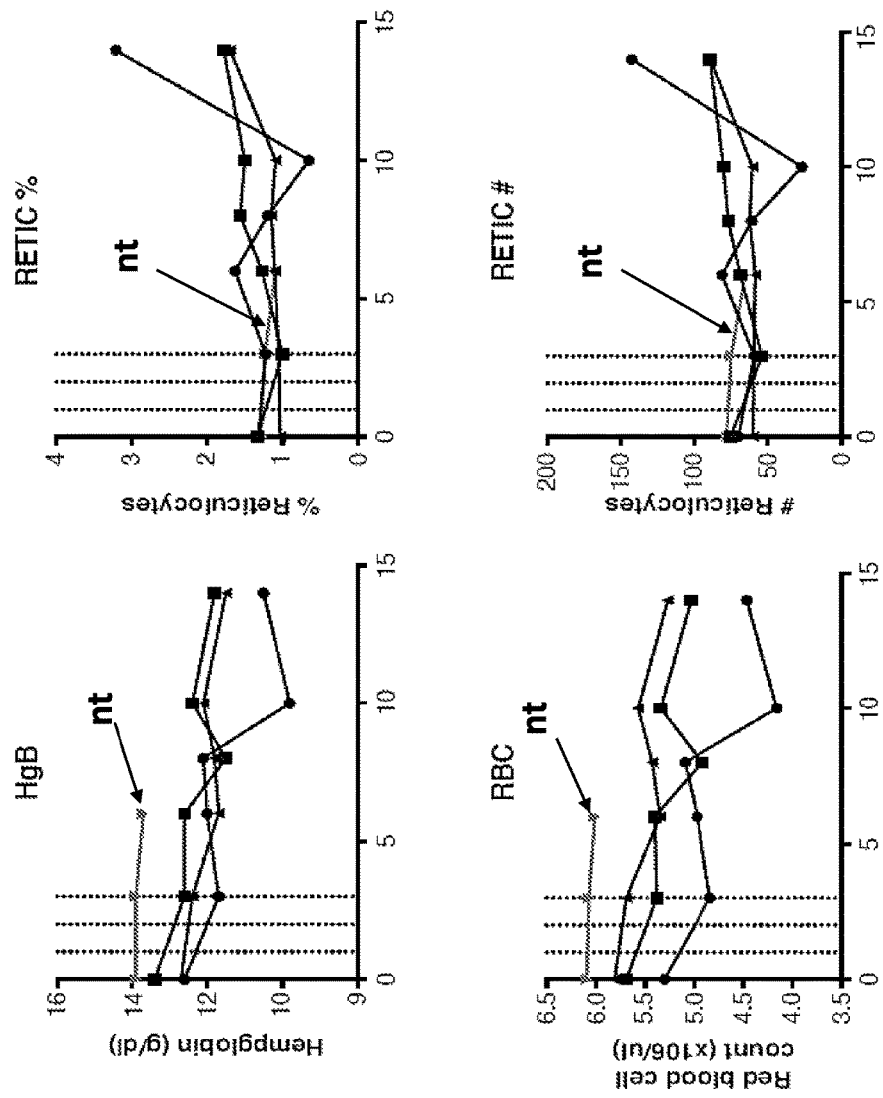
Figure 10B:
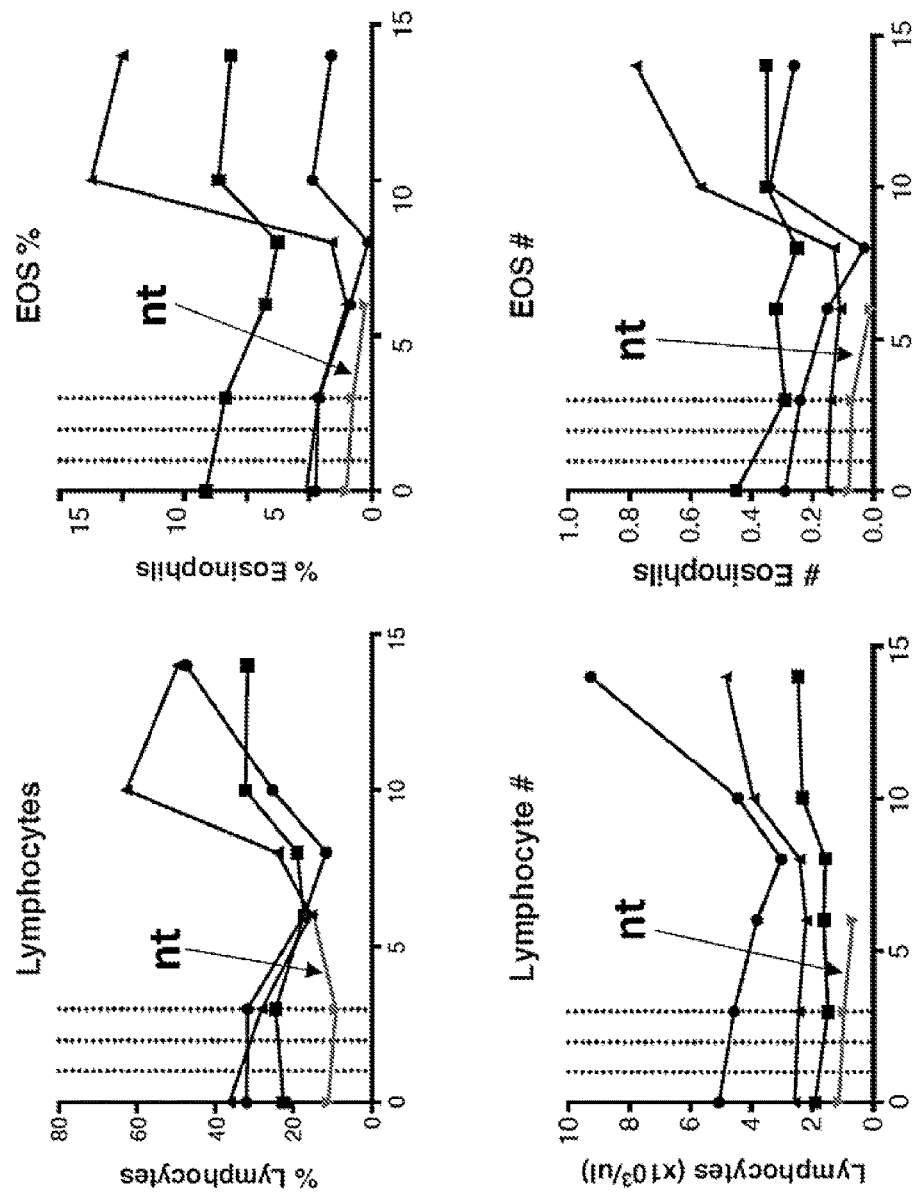
Figure 10C:
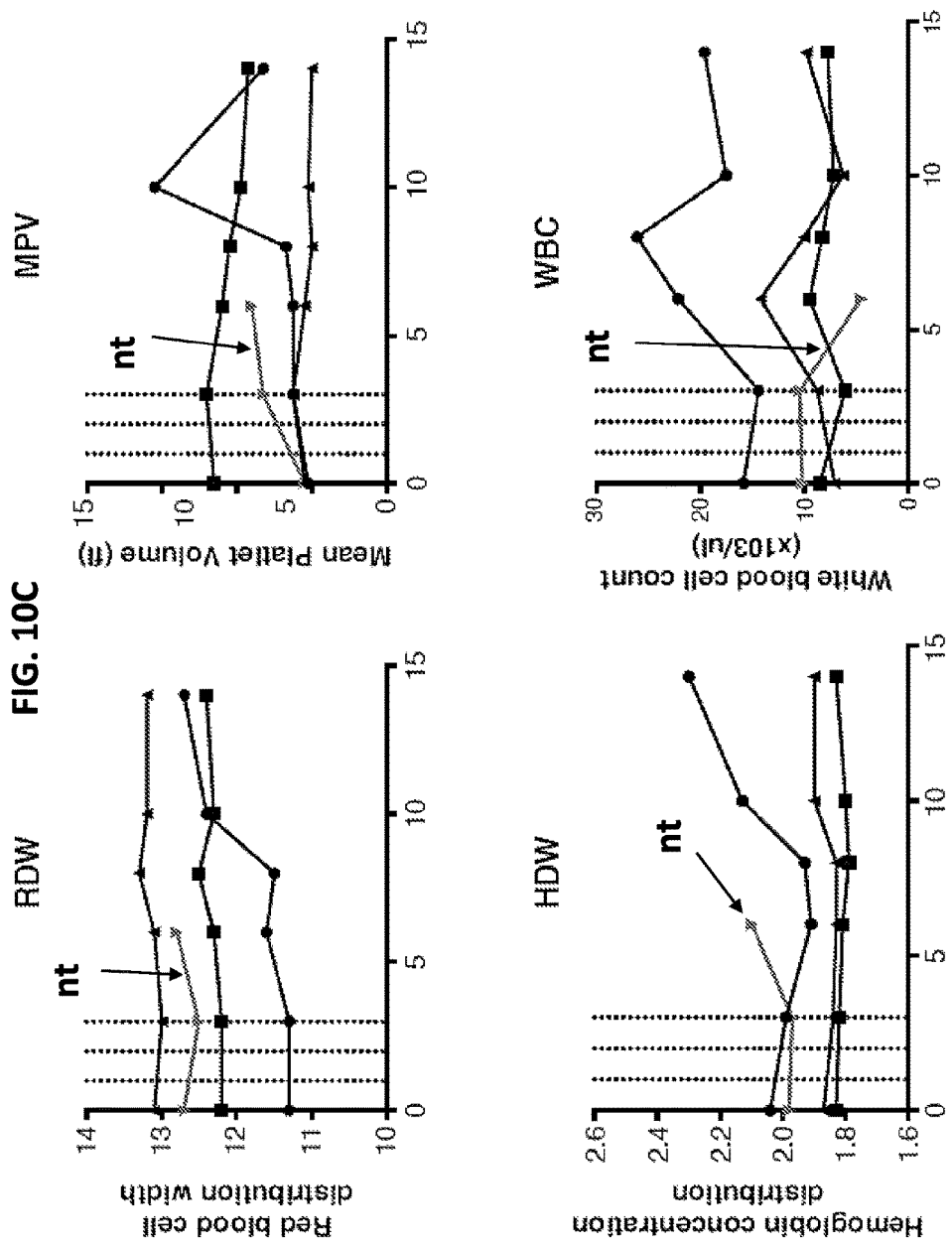
Figure 10D:
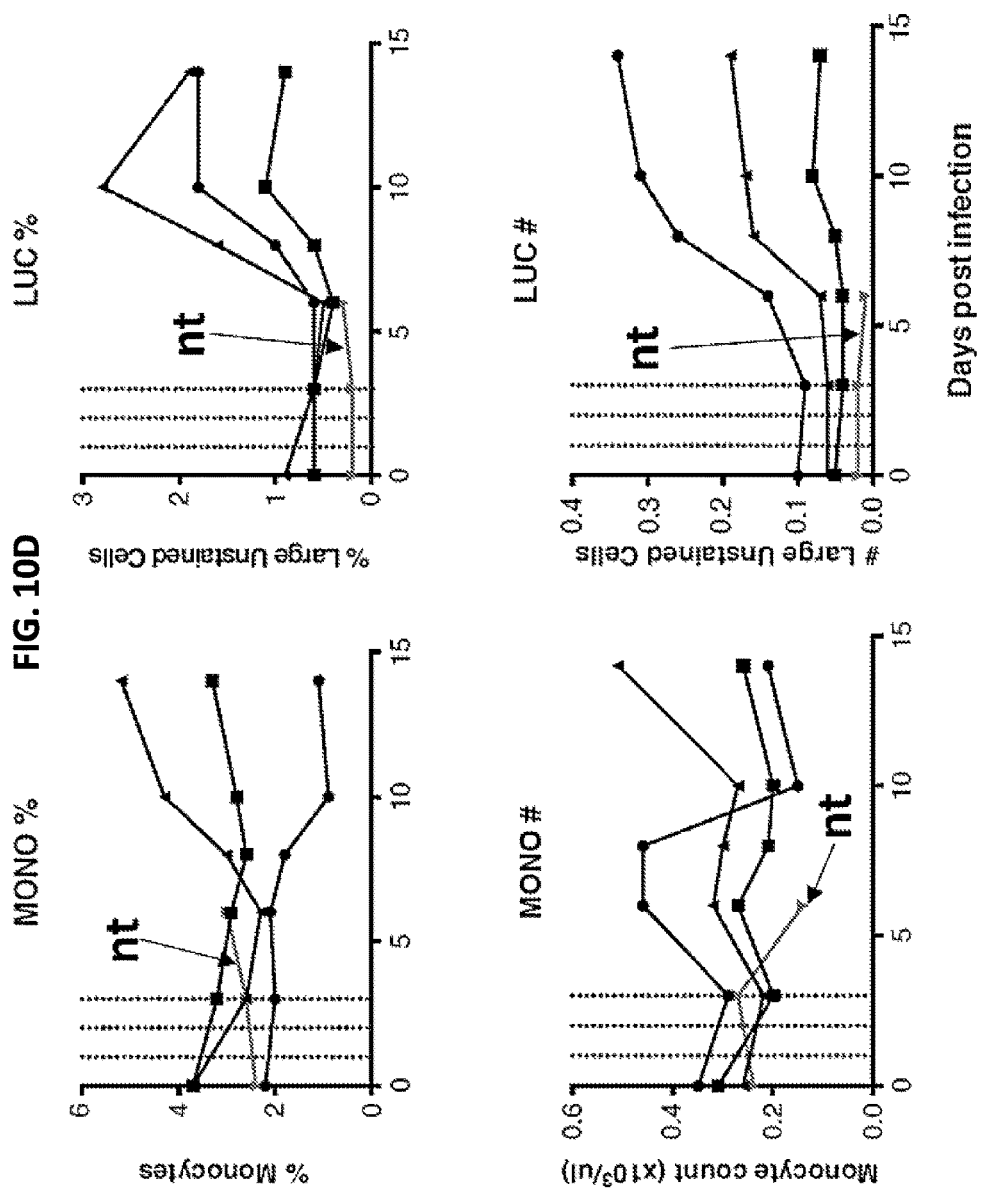
Figure 10E:
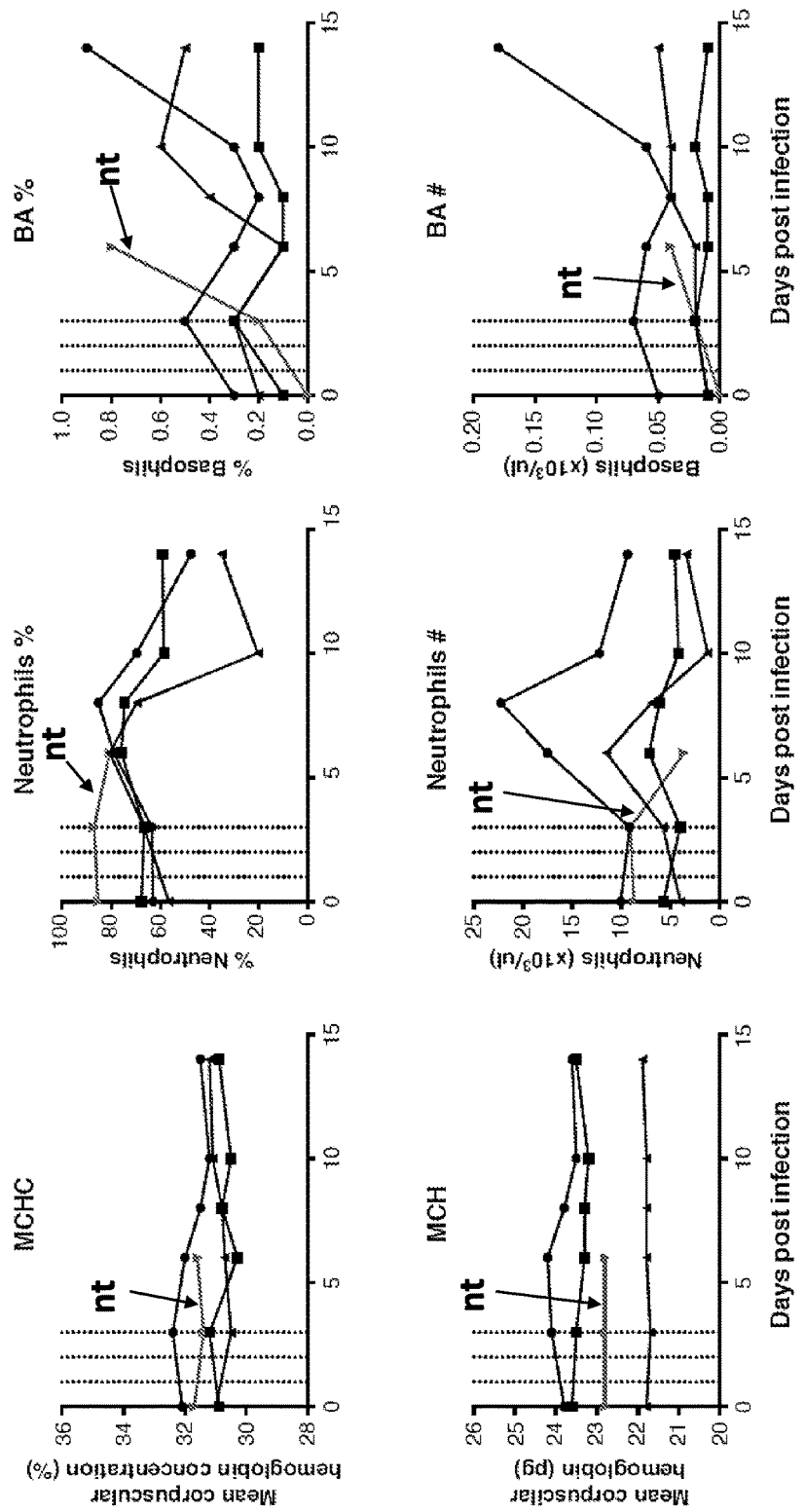
Figure 11A:
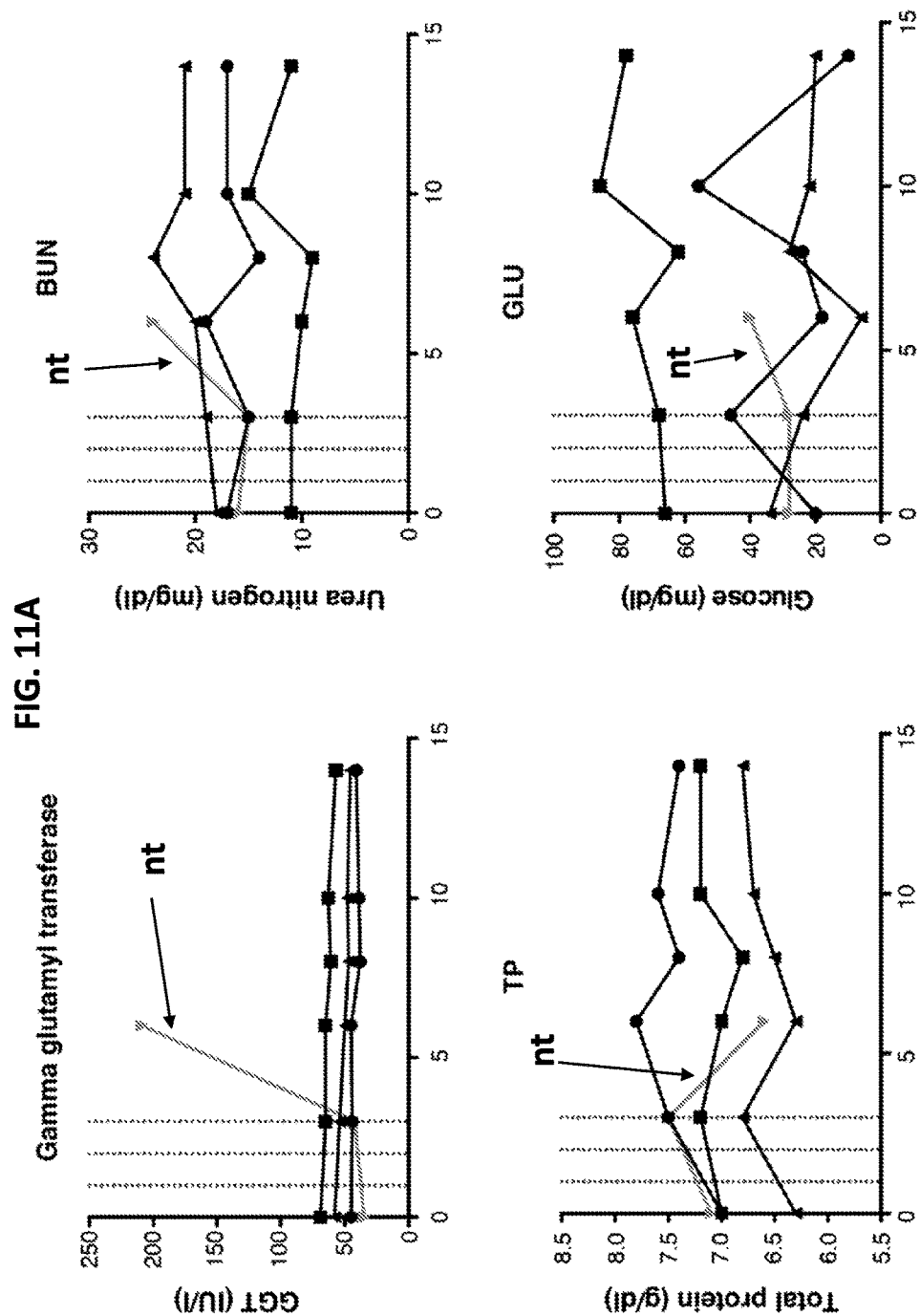
Figure 11B:
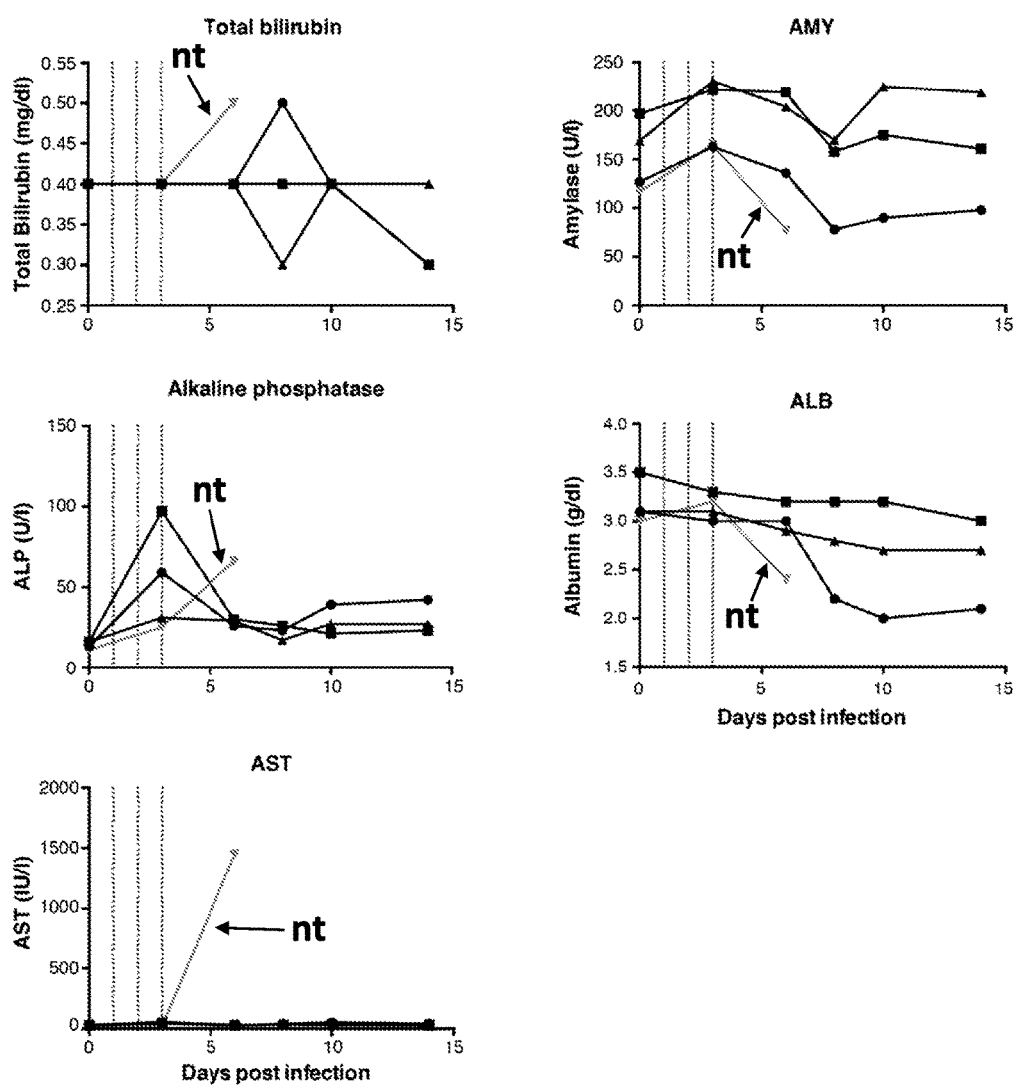

EVB165 and EVB166 both neutralized well and exhibited similar potencies for half maximal inhibition (IC50) concentration of 1.77 and 0.86 µg/ml, respectively. EVB100 and EVB114 resided in the strongest neutralizing group, with IC50 about one-log greater (0.06 and 0.09 µg/ml, respectively) than EVB165 and EVB166. Notably, all four of the neutralizing antibodies inhibited 100% of the input virus unlike KZ52, which consistently displayed only 80-90% maximum inhibition, and 13C6 which neutralized <20% at 10 µg/mL. Importantly, neutralization of the 2014 West African Makona variant was achieved within similar concentration ranges seen for the Mayinga variant (FIG. 5).

Sequence analysis revealed EVB114 and EVB165 to be IgG$_1$ isotypes, and EVB100 and EVB166 to be IgG$_3$ isotypes. Immunoglobulins displayed between 85-95% and 89-97% germline identity for heavy and light chains, respectively (FIG. 2C). Analyses of germline gene usage and V(D)J recombination indicate that they originate from different B-cell lineages. Interestingly, EVB114 utilizes IGHV3-13*01, a rarely used VH gene, and IGKV1-27*01.

Figure 2I:
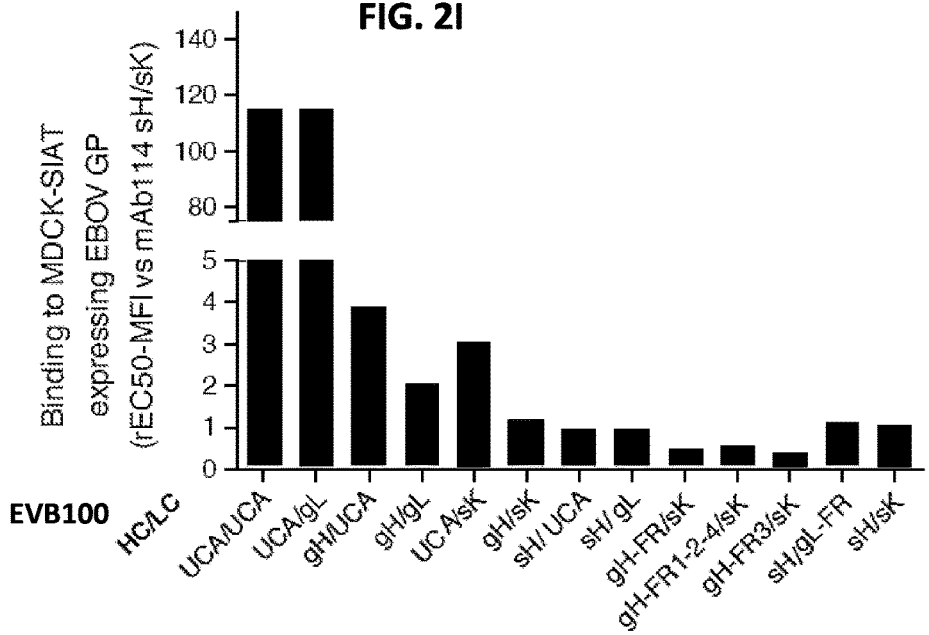

The role of somatic hypermutations for the two most potent antibodies, EVB100 and EVB114, was analyzed using variants that were partially or completely reverted to the unmutated common ancestors (UCAs) (FIGS. 2D to 2G). The fully reverted version of EVB100 (UCA/UCA), as well as a variant with germline VH and a VL with a single change from germline (A89T), recognized cells expressing GP with only a 2- to 4-fold weaker binding compared with the fully matured antibody (FIG. 2H). GP binding comparable to the fully matured EVB100 heavy and light chains (sH/sL) was observed when three HCDR3 mutations (A96V/V103Y/Y114S) were introduced in the reverted germline antibody (gH/UCA), illustrating that those mutations were sufficient to mediate binding observed with fully matured EVB100. The addition of all the other mutations did not contribute further to EVB100 binding to GP. In the case of the EVB114, the fully reverted version of EVB114 (UCA/UCA) demonstrated negligible binding to EBOV GP (FIG. 2I). Introduction of two mutations (A96V and Y108S) in the HCDR3 of EVB114 germline was sufficient to confer an increase in GP binding. It is intriguing that these mutations (A96V and Y108S) are located at the base of the HCDR3 loop which are most likely not in direct contact with GP but may have a stabilizing effect on the whole HCDR3. Indeed, restoration to the binding equivalent of the mature antibody required a fully matured light chain in addition to the two HCDR3 mutations. Inherent uncertainty in determining the germline configuration of the HCDR3 does not appear to apply to this case since the two mutations are located in the V and J regions of the junction and no polymorphisms have been described at those positions. Importantly, the fully mutated light chain gene, as shown in the case of the EVB114 UCA/sK variant, can partially compensate for the lack of somatic mutation in the heavy chain (FIG. 2I). The presence of additional mutations on either VH or VK is required to achieve the level of the fully matured EVB114 binding. These results suggest a rapid pathway of EVB114 affinity maturation through one or two somatic mutations, which became redundant as further mutations accumulated, a finding that is reminiscent of what was recently observed for the generation of broadly neutralizing influenza antibodies (Pappas et al., Nature. 516, 418-22, 2014).

Figure 3A:
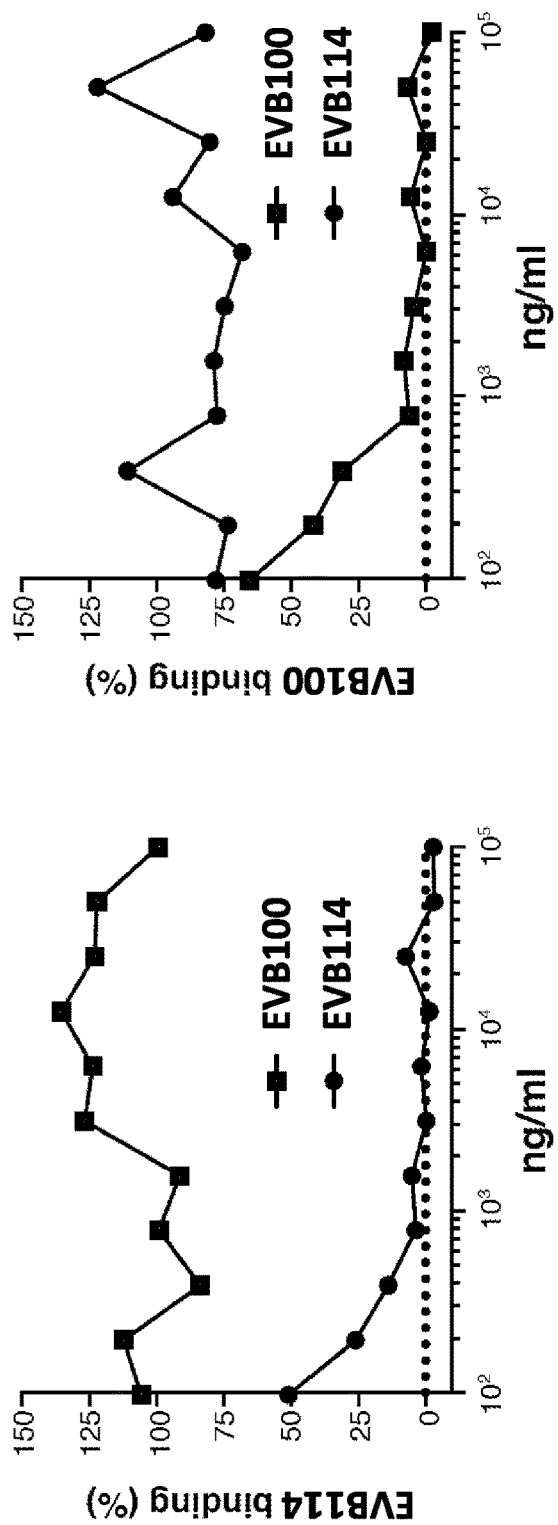
FIGS. 3A-3D are a set of graphs and tables concerning the binding region and effector function of EBOV GP specific antibodies. (3A) Inhibition of binding of biotinylated EVB114 (left) and EVB100 (right) to GP-expressing MDCK-SIAT cells by pre-incubation with increasing amounts of homologous or heterologous unlabeled antibodies. Shown is the percentage of binding of biotinylated antibodies as measured by flow cytometry using fluorophore-conjugated streptavidin. (3B) and (3C) Biolayer interferometry competitive binding assay to soluble EBOV GP using EVB100, EVB114, KZ52, 13C6 and isotype negative control. Biosensors were preloaded with GP followed by the competitor and analyte antibodies as indicated. Analyte binding curves (3B) and quantitated % inhibition (3C) are reported (n=3). (3D) Antibody-dependent cell-mediated cytotoxicity (ADCC) assay was determined at 31.6 ng/mL of EVB100, EVB114 (n=3), control antibody or derivative antibodies with LALA mutations that abrogate Fc365 mediated killing (n=1).
Figure 3B:
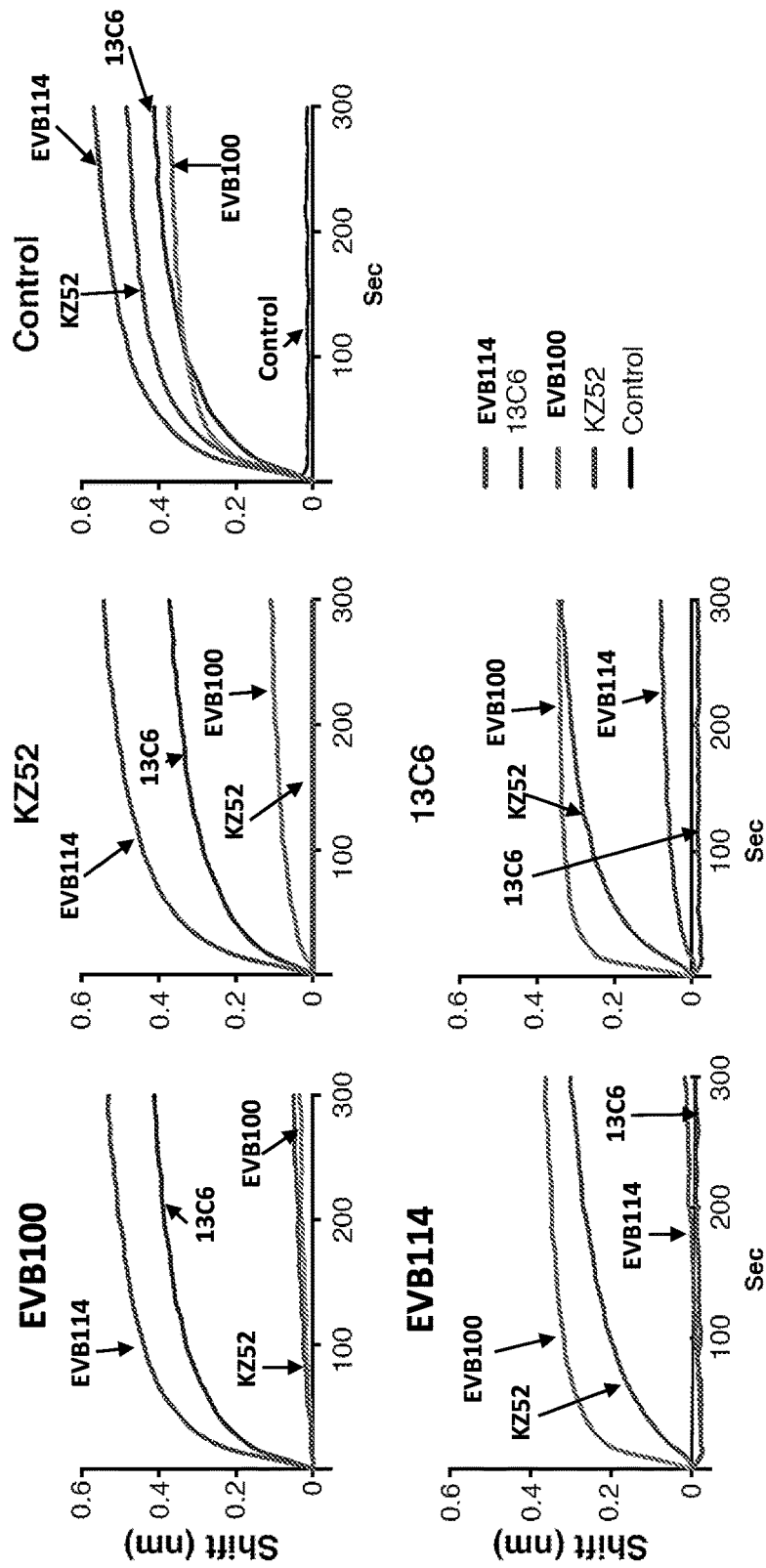
Figures 3C, 3D:
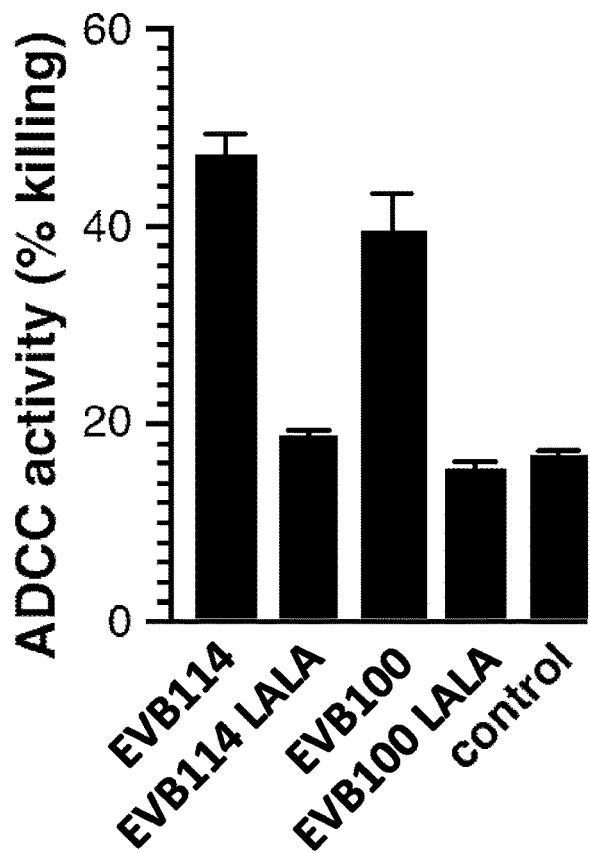

Since EVB100 and EVB114 were the most potently neutralizing antibodies, they were considered optimal candidates for further evaluation. The potential for synergy between these antibodies in the context of combination therapy was assessed. First, to possibility of cross-competition for antigen binding or targeting of a single immunodominant region of GP was assessed. It was found that each antibody bound to GP in the presence of the other, suggesting that they recognize distinct regions on GP (FIG. 3A) and therefore could be used together in combination immunotherapy to improve efficacy and diminish the likelihood of emergence viral escape mutants (Barouch et al., Nature. 503, 224-8, 2013; Shingai et al., Nature. 503, 277-80, 2013). To define the regions targeted by EVB100 and EVB114, biolayer interferometry was employed to assess GP binding in competition with mAbs KZ52 and 13C6, which have known epitopes in the GP base and glycan cap, respectively (Lee et al., Nature. 454, 177-82, 2008; Murin et al., Proc. Natl. Acad. Sci. U.S.A 111, 17182-17187, 2014). It was found that EVB100 competes with KZ52 for binding at the base of GP, while EVB114 recognizes at least in part the glycan cap region, as demonstrated by the partial competition observed with 13C6 (FIGS. 3B and 3C). Since some EBOV GP antibodies have been suggested to mediate antibody dependent cell-mediated cytotoxicity (ADCC) (Olinger et al., Proc. Natl. Acad. Sci. U.S.A 109, 18030-5, 2012) the ADCC activity of EVB100 and EVB114 were determined in a flow cytometry-based assay using GP-expressing target cells (FIG. 3D). It was found that both EVB100 and EVB114 mediated ADCC, and maximum activity was observed at a mAb concentration of 0.03 µg/ml, which is similar to the IC50 values for neutralization Killing of target cells was demonstrated to be mediated through Fc receptors since LALA mutations in the mAb Fc regions (Hezareh et al., J. Virol. 75, 12161-12168, 2001) of the antibodies abrogated ADCC activity. Therefore, in addition to neutralization, these mAbs have the potential to induce direct killing of infected cells in vivo, a key viral clearance mechanism.

Figures 4E, 4F, 4G, 4H:
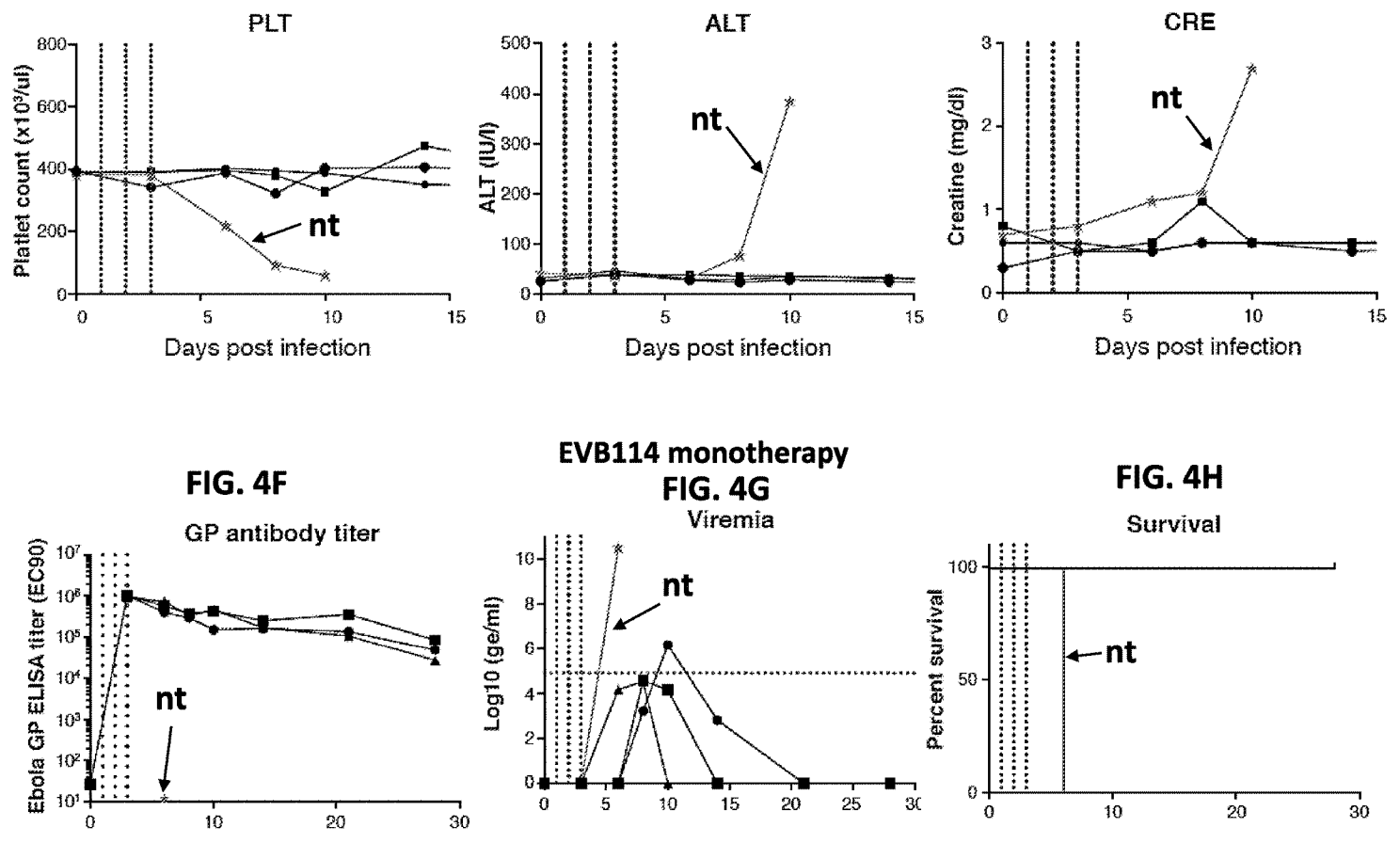

The presence of potent neutralizing and ADCC activity, and the absence of cross competition, supported testing EVB100 and EVB114 in vivo for protective efficacy in macaques. Four rhesus macaques (*Macaca mulatta*) were challenged with a lethal dose of Ebola virus, Kikwit 1995 variant. One day post-challenge, the treatment group (n=3) was given an intravenous injection with a mixture of EVB100 and EVB114 at a total combined dose of 50 mg/kg, and the treatment was repeated twice more at 24-hour intervals (FIG. 4A). Circulating Ebola GP-specific antibody titers in the mAb recipients peaked after the second mAb injection and reciprocal ELISA titers remained above $10^5$ throughout the study, suggesting minimal clearance of the mAbs during the observation period (FIG. 4B). The naive untreated macaque succumbed to EVD on day 10 with a circulating viral load exceeding $10^8$ ge/ml (FIGS. 4C and 4D). In contrast, all three mAb treated macaques survived challenge without detectable systemic viremia. Consistent with historic controls, the untreated animal displayed hallmark indicators of Ebola infection including hematologic, liver and renal dysfunction as indicated by thrombocytopenia and striking elevations in alanine transaminase (ALT) and creatinine from day 6 through the time of death (FIGS. 4E, and 6-8). In contrast, macaques in the treatment group remained within normal ranges for these parameters, and remained free of all EVD symptoms.

Figure 4I:
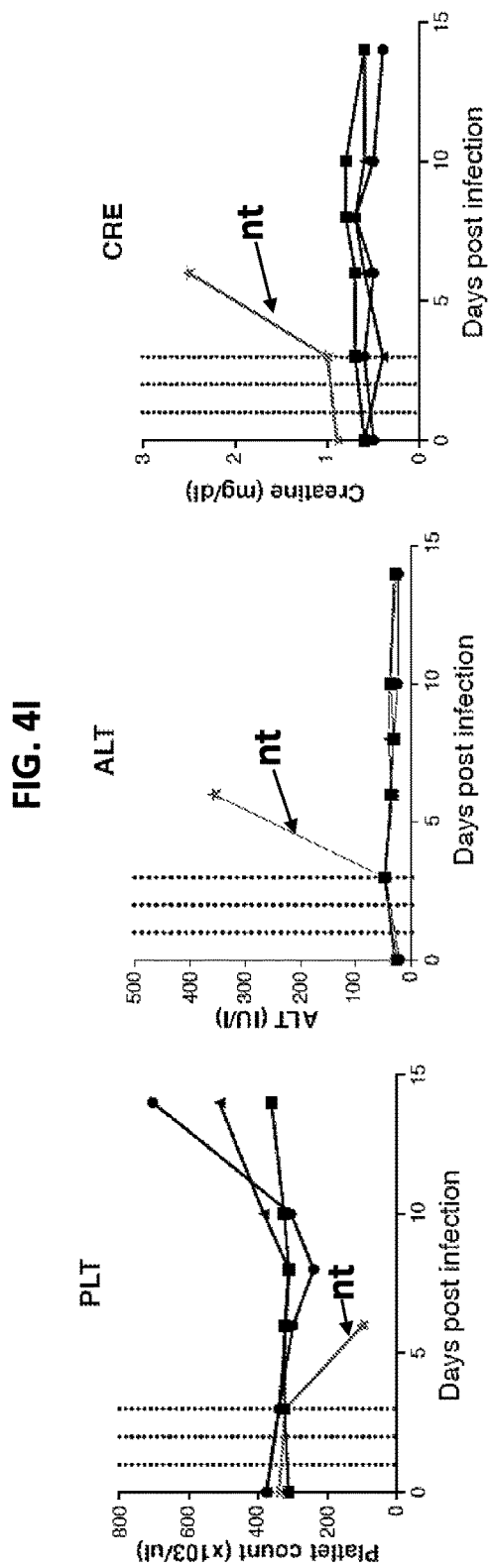

Assays were also performed to determine if mAb monotherapy is sufficient for protection of NHP. Initial testing focused on EVB114, since it showed higher maximal binding than EVB100. As in the first experiment four macaques were exposed to a lethal dose of EBOV and administered 50 mg/kg of EVB114 (n=3) to the treatment group after a one-day delay, followed by two more doses at 24-hour intervals. All treated macaques survived, whereas the control animal succumbed to EVD on day 6 with a peak viral load of $10^{10}$ ge/ml (FIGS. 4F to 4H). In contrast to the previous experiment, transient viremia was observed in the treated animals, but it remained at levels less than 0.1% of the untreated control animal, and returned to undetectable levels. Despite transient viremia, treated animals remained free of clinical and laboratory abnormalities (FIGS. 4I, and 9-11).

The neutralization activity of the EVB100, EVB114, EVB165, and EVB166 antibodies was further assayed in the presence of soluble GP (sGP), which is believed to interfere with the natural immune response to EBOV in human subjects (FIG. 12). The neutralization assay was performed as above and using the IC50 concentration of each antibody in the presence or absence of sGP. As shown in FIG. 12, the neutralization potency of EVB100 was not affected by the presence of sGP; however, neutralization by the EVB114, EVB165, and EVB166 antibodies was diminished in this in vitro assay.

EBOV GP is initially synthesized as precursor protein ($GP_0$) that is cleaved by cellular furin to form the surface glycoprotein $GP_1$ and the membrane anchoring protein $GP_2$. $GP_1$ and $GP_2$ are linked in the mature virion trimer by disulfide bonds. There are other GP forms created during cellular trafficking and processing that may also bind to antibodies in the infected host. Since binding specificity to the various GP forms may influence in vivo efficacy of the antibodies, the EVB100, EVB114, EVB165, and EVB166 antibodies were assayed to determine if they could immunoprecipitate GP (FIG. 13). KZ52 was used as a positive control. As shown in FIG. 13, each of the EVB100, EVB114, EVB165, and EVB166 antibodies can immunoprecipitate GP. EVB114 immunoprecipitated $GP_1$ and $GP_2$, suggesting that it binds to the mature, disulfide-linked trimer. EVB114 also immunoprecipitated the lower molecular weight cathepsin-cleaved form of GP (GPCatL). The EVB100, EVB165, and EVB166 antibodies bind to precursor forms of GP present prior to furin or cathepsin cleavage.

Figure 14A:
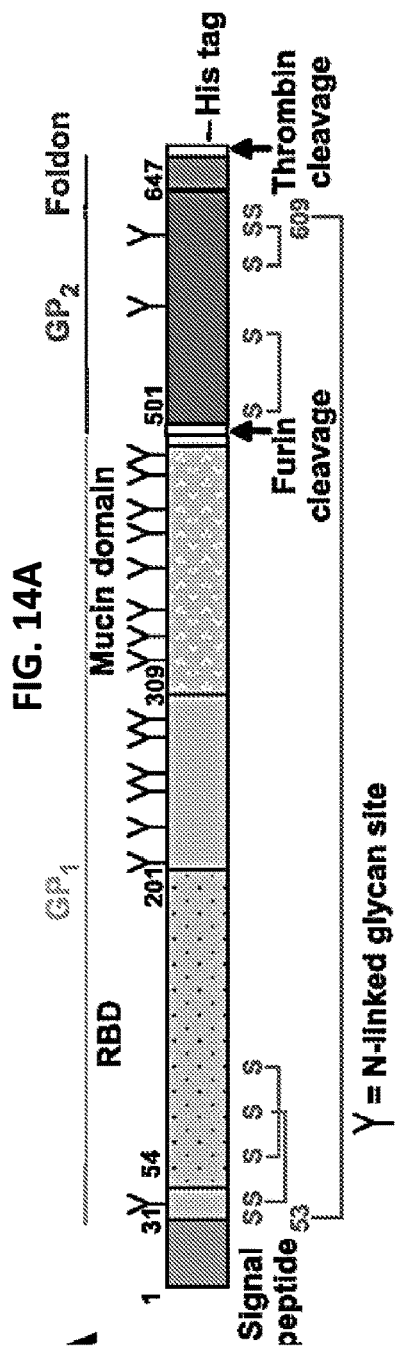
FIGS. 14A and 14B are a set of diagrams illustrating EBOV GP and regions thereof (FIG. 4A) and several deletion mutants of EBOV GP used herein (FIG. 4B).
Figure 14B:
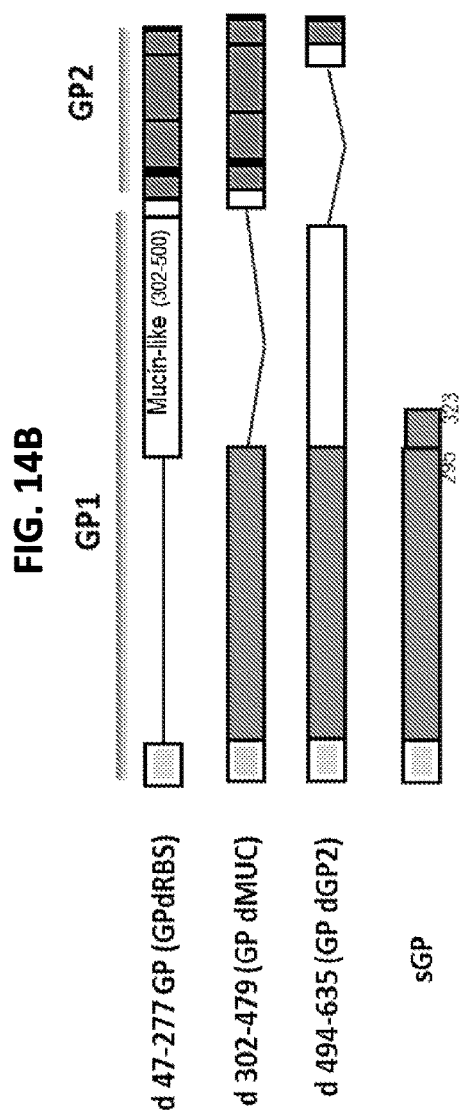
Figure 15:
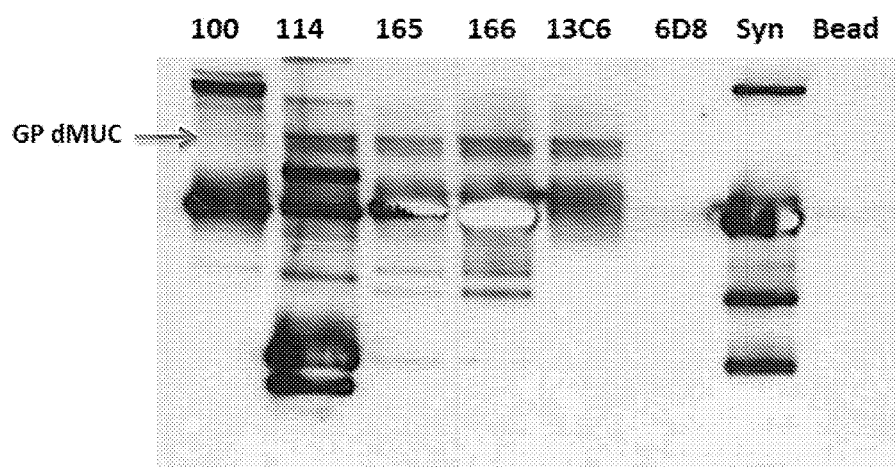
FIGS. 15 and 16 are a set of Western blots illustrating the ability of the EVB100, EVB114, EVB165, and EVB166 antibodies to immunoprecipitate the GP dMUC and GP dGP2 deletion mutants illustrated in FIG. 4B.
Figure 17A:
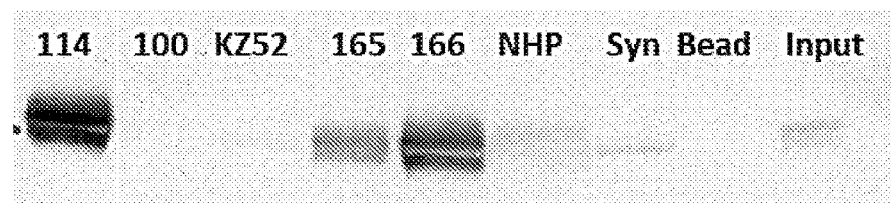
FIGS. 17A and 17B are a set of Western blots illustrating the ability of the EVB100, EVB114, EVB165, and EVB166 antibodies to immunoprecipitate the sGP form of EBOV GP (FIG. 7A) and to recognize the sGP form by direct Western blot (FIG. 7B).
Figure 17B:
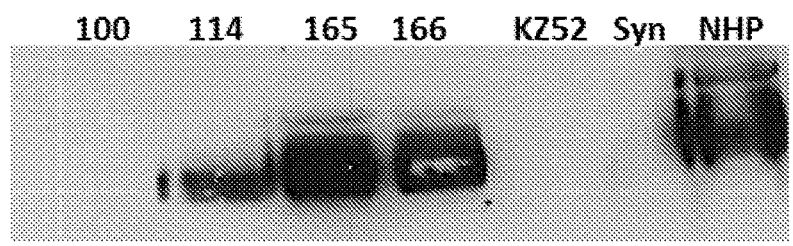

To further assess the binding properties of the EVB100, EVB114, EVB165, and EVB166 antibodies for GP, several GP deletion mutants were assayed for binding to these antibodies (FIGS. 14 and 15). GP deletion mutants were constructed that lack the N-terminus (containing the putative receptor binding domain, (d47-277, "GPδRBS"), the highly glycosylated mucin-like PdMUC"), or the C terminus of EBOV GP (d494-635, "GP dGP2") (see FIG. 14). Additionally, binding to sGP was also assessed (FIGS. 17A and 17B).

Figure 16:

Gross epitope mapping was performed by expressing the GP mutants in mammalian cells, followed by immunoprecipitation using the EVB100, EVB114, EVB165, or EVB166 antibodies and detection of precipitated protein by Western blot with EBOV GP specific antibody (FIGS. 15-17). Deletion of the GP mucin-like domain reduced recognition by EVB100 in immunoprecipitation assays, but the other antibodies recognized GP in the absence of the mucin-like domain (FIG. 15). This finding indicates that deletion of the mucin-like domain alters (or deletes) at least part of the EVB100 epitope on EBOV GP. Further, deletion of $GP_2$ reduced recognition by EVB100 in immunoprecipitation assays, but the other antibodies recognized GP in the absence of the $GP_2$ polypeptide (FIG. 16). This finding indicates that deletion of the $GP_2$ polypeptide alters (or deletes) at least part of the EVB100 epitope on EBOV GP.

The EVB100, EVB114, EVB165, and EVB166 antibodies were also assessed for binding to soluble GP (sGP) by immunoprecipitation (FIG. 17A). sGP contains the GP receptor binding domain; therefore, the N-terminal portions of sGP and GP as found on the viral envelope are homologous in that they each contain putative receptor binding domain. EVB114, EVB165, and EVB166 all immunoprecipitated sGP indicating that each of these antibodies binds to an epitope within the N-terminal portion of the GP protein, which includes the receptor binding domain. Further, recognition by direct WB suggests that binding is to a linear, not conformation-dependent epitope (FIG. 17B). In contrast, EVB100 does not bind to N-terminal GP sequences by either direct WB or IP/WB that preserves conformation. This is consistent with the previous finding that EVB100 binding requires elements in the mucin and $GP_2$ regions of GP.

Figure 18:
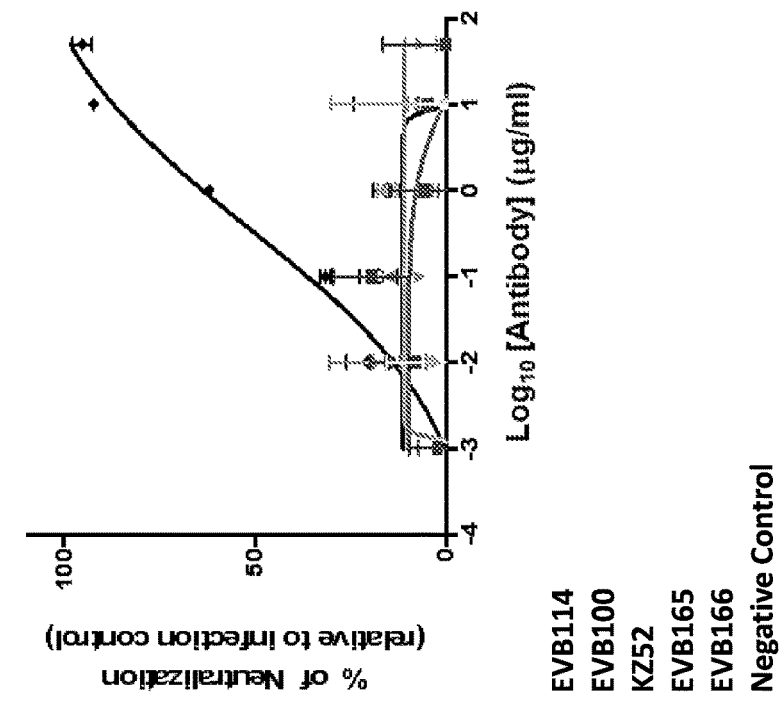
FIG. 18 is a set of graphs illustrating the cross-species neutralization properties of the EVB100, EVB114, EVB165, and EVB166 antibodies. Pseudotyped lentiviral vectors expressing EBOV GP from the Bundibugyo or Sudan EBOV strains were incubated with antibody prior to infection of 293T cells, and infection inhibition was calculated as a percent of infection in the absence of antibody.
Figure 18:
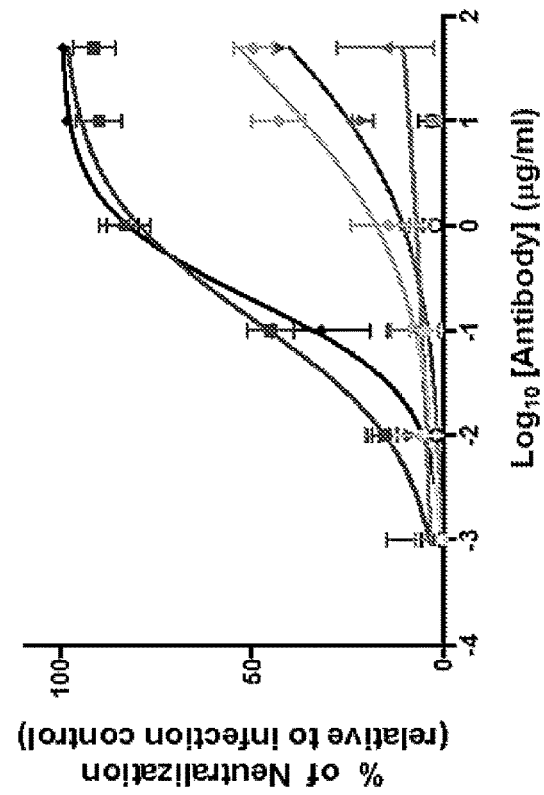

The EVB100, EVB114, EVB165, and EVB166 monoclonal antibodies were further assayed for neutralization of the Bundibugyo (BDBV) and Sudan (SUDV) Ebola virus strains, which have previously causes highly lethal outbreaks in humans (FIG. 18). Cross-species neutralization was assayed using a single-round replication assay with virus pseudotyped with the envelope glycoprotein (GP) from each species. As shown in FIG. 18, the EVB100 and EVB166 antibodies potently neutralized BDBV, while EVB114 and EVB165 displayed modest cross recognition and neutralization. EVB166 was additionally neutralized the SUDV pseudovirus.

EVB114 has several characteristics that may contribute to protection as a monotherapy compared to KZ52 and 13C6, which were non-protective in NHPs (Qiu et al., *Nature.* 514, 47-53, 2014; Oswald et al., *PLoS Pathog.* 3, e9, 2007). Firstly, both KZ52 and EVB114 neutralize with potent IC50s, however EVB114 neutralizes 100% of input virus whereas KZ52 plateaus at 80-90%. Secondly, EVB114 does not require complement for neutralizing activity in contrast to 13C6 (FIG. 2B) (Wilson et al., *Science.* 287, 1664-6, 2000). Based on these observations, one non-limiting conclusion is that protective monotherapy requires both potent binding and complete neutralization in the absence of complement. In addition, ADCC activity may contribute to the unique ability of EVB114 to protect as a monotherapy against lethal Ebola infection of macaques.

Data presented in this example shows that circulating functional antibodies as well as memory B cells specific to Ebola virus are maintained in survivors for more than a decade following infection. mAbs isolated from a survivor of the 1995 Kikwit EVD outbreak exhibited ADCC activity and showed potent neutralizing activity against two other Ebola variants, including one from the recent West Africa outbreak. Macaques who received EVB114 and EVB100 as combination therapy remained healthy with no signs of viremia after EBOV challenge. Strikingly, when a single antibody, EVB114, was therapeutically administered after lethal EBOV challenge of macaques, all treated animals were fully protected and asymptomatic, despite a low transient level of circulating virus being detected.

Materials and Methods

Isolation of Monoclonal Antibodies from EBOV Survivors.

Two subjects who survived the 1995 EBOV Kikwit variant outbreak in the Democratic Republic of Congo were identified and enrolled in VRC200 clinical trial #NCT00067054 after giving signed informed consent. Peripheral blood mononuclear cells (PBMCs) were obtained, stained with directly labeled antibodies to CD22 (Pharmingen) and to immunoglobulin IgM, IgD, and IgA. CD22+IgM-IgD-IgA-B cells were isolated using FACS Aria, pulsed with Epstein-Barr Virus (50% B958 supernatant) and seeded at 30 cells/well (for a total of 2.7×105 purified cells) in replicate cultures in medium supplemented with CpG 2006 and irradiated allogeneic PBMCs, as previously described (Traggiai et al., *Nat. Med.* 10, 871-875, 2004). Culture supernatants were collected after 2 weeks and tested for binding to ELISA plates coated with EBOV GP (Mayinga variant), their specificity was confirmed using an unrelated antigen (tetanus toxoid) and positive cultures were further tested for their ability to neutralize EBOV pseudoviruses. Cultures that scored positive in the EBOV neutralization assay were subcloned by limiting dilution.

Antibody Purification, Labeling, Genetic Analysis, and Reversion to Germline.

The usage of VH and VL gene segments was determined by sequencing, and analysis for homology to known human V, D, and J genes was performed using the IMGT database (http://www.imgt.org/). Human antibodies were affinity purified by protein A chromatography (GE Healthcare) and dialyzed against PBS. Selected antibodies were biotinylated using the EZ-Link NHS-PEO Solid Phase Biotinylation Kit (Pierce).

Antibodies were also produced recombinantly by cloning VH and VL genes via PCR into human Igγ1, Igκ (EVB114, 165, 166), and Igλ (EVB100) expression vectors using gene specific primers (Tiller et al., *J. Immunol. Methods.* 329, 112-124, 2008). Antibodies used for animal studies were produced by transient transfection of suspension cultured 293FreeStyle cells (Invitrogen) with PEI or Expi cells with Expifectamine293 (Invitrogen). Supernatants from transfected cells were collected after 6-10 days of culture and IgGs were affinity purified by Protein A chromatography (GE Healthcare) and dialyzed against PBS. Purified mAbs were then concentrated with Amicon Ultra centrifugal filters and sterilized by 0.22 μm filtration. The purity was assessed by SEC-HPLC and SDS-PAGE. Endotoxin content was measured with the Endpoint Chromogenic LAL assay (QCL-1000 ™ assay, Lonza) according to manufacturing instructions and shown to be below 0.25 EU/ml. Antibody concentrations were determined using the BCA Protein Assay Kit (Thermo Scientific) using Rituximab (Roche) as internal standard or A280 using an Nanodrop (Thermo Scientific). Germlined VH and VL nucleotide sequences were synthesized by Genscript, and their accuracy was confirmed by sequencing.

Antibodies.

KZ52 monoclonal antibody used in ELISA assay a kind gift from Dennis Burton. KZ52 used elsewhere and 13C6 was purchased from IBT Bioservices. Unless otherwise noted isotype control antibody was an anti-HIV gp120 IgG1.

Antibody Neutralization Assay.

Supernatants or purified mAbs from immortalized B cell clones isolated from EVD survivor donors were assessed for neutralization potency using a single-round infection assay with EBOV GP-pseudotyped lentiviruses particles which express a luciferase reporter gene following entry (Sullivan et al., *PLoS Med.* 3, e177, 2006). Unless indicated, all experiments utilized particles bearing GP from the EBOV Mayinga variant. In brief, HEK293T cells were used as infection targets and incubated in a 96-well plate 1 day before infection with pseudovirus in the presence of serially diluted supernatant or purified mAbs. Infected target cells were lysed 72 hours after infection and assayed with the Luciferase Assay System or Bright Glo (Promega), using a Victor X3 Plate Reader (PerkinElmer) to detect luciferase activity.

ELISA for serum antibody titer and GP-binding. Binding of EVD survivor's polyclonal sera, monoclonal antibodies and antibody in non-human primates to EBOV GP was evaluated by enzyme-linked immunosorbent assay (ELISA) as described previously (Sullivan et al., *PLoS Med.* 3, e177, 2006). Titers for survivor and non-human primates were calculated as reciprocal EC90 values (Sullivan et al., *PLoS Med.* 3, e177, 2006).

Ebola Virus GP Vectors.

Plasmid vector pVR1012 WT GP (Z) has been described previously (21). A vector expressing a soluble mucin deleted (ΔMuc) GP, GPΔMucΔTM-GCN4 HisSA (4309-505, Δ657-676), was made using codon optimization and then synthesized and directly cloned in frame to a GCN4 trimerization domain-His-Strep Tactin domains (MKQIEDKIEEILSKIYHIENEIARIKKLIGEVASSSIEGRGSHHHHHHSAWSHPQFEK, SEQ ID NO: 66) and sequence verified by Genscript. EBOV GP variant Makona-005 (Acc#KJ660348) was codon optimized, synthesized and sequence verified by Genscript.

Antibody-Dependent Cell-Mediated Cytotoxicity (ADCC).

rAd5 EBOV GP-transduced and non-transduced HEK293T cells were double labeled with membrane-bound and intracellular stains in order to detect ADCC activity. Cells were incubated with 8 μM Plum stain (Plum cell labeling kit M.T.T.I. CellVue) followed by FBS. The cells were then washed with RPMI 1640, incubated with 5 μM Carboxyflourescein Succinimidyl ester (CFSE) (Vybrant CFDA SE cell tracer kit, Invitrogen), incubated with FBS and washed again with RPMI 1640. Doubly labeled EBOV GP expressing cells were plated in a V-bottomed 96-well plate at 5,000 cells/well. Antibodies were added to duplicate samples at 31.6 ng/ml to the target cells for 20 minutes at room temperature. RSV antibody (palivizumab) was used as a control antibody. Effector cells resuspended in RPMI were then added to the target cells at the effector-to-target cell (ET) ratio 1:50 which was found to give the best signal to noise ratio. Each plate was incubated for 4 hr at 37° C./5% $CO_2$. After 4 hr, plates were centrifuged at 250×g and cells were fixed with 1% Paraformaldehyde (PFA) and analyzed via flow cytometry. As a control, labeled non-transduced HEK293T cells were also used as targets for ADCC activity. Thirty thousand non-gated events were acquired within 6 hr after the ADCC assay using an LSRII cytometer (Becton Dickinson). The CFSE emission channel was read in B515 using a neutral density filter and Plum emission was read in R660. Following acquisition, analysis was performed using FlowJo software (Tree Star). Percent killing was obtained by quantifying dead cells (Plum+,CFSE−) out of the total Plum positive population. For mAbs, ADCC killing was measured by subtracting percent killing of nontransduced cells from percent killing of transduced cells.

Antibody Variants.

UCA sequences of the isolated antibodies were determined with reference to the IMGT database (imgt.org). Antibody variants in which single or multiple mutations were reverted to the germline sequence were produced by gene synthesis (Genscript) and used to produce a large set of EVB114 and EVB100 antibody variants.

Binding of antibody variants to transfected cells.

EVB114 and EVB100 antibody variants were used to stain MDCK-SIAT1 cell lines transduced to express EBOV GP as a stable membrane protein (Makona variant). Binding of antibodies was analysed using a Becton Dickinson FACS Canto2 (BD Biosciences) with FlowJo software (TreeStar). The relative affinities of antibody binding to surface GP were determined by interpolating the concentration of antibody required to achieve 50% maximal binding (EC50) from the plotted binding curves using the mean-fluorescence intensity (MFI) fitted with a 4-parameter nonlinear regression with a variable slope.

Inhibition of Binding Assay on GP-Expressing Cells.

EVB100 and EVB114 were biotinylated using the EZ-Link NHS-PEO solid phase biotinylation kit (Pierce). Labeled antibodies were tested for binding to GP-expressing MDCK-SIAT-1 cells to determine the optimal concentration of each antibody to achieve 70-80% maximal binding. The biotin-labelled antibodies were then used as probes to assess, by flow cytometry, whether their binding (measured using fluorophore-conjugated streptavidin) was inhibited by preincubation of GP cells with homologous or heterologous unlabelled antibodies.

Production of Purified GP.

Expi (Invitrogen) cells were transfected with GP ΔMucΔTM-GCN4 HisSA and pCMV-Sport Furin (7:3 ratio) using 293Fection (Invitrogen) at a ratio of 2 mL 293Fectin: 1mg total DNA. 18-24 hours following transfection, ¹⁄₁₀th volume of AbBooster (ABI Scientific) was added and culture media collected 5 days later. Supernatant was filtered and protein purified as described previously (Cote et al., *Nature*. 477, 344-348, 2011).

Biolayer Interferometry Antibody Cross-Competition Assay.

Antibody cross competition was determined based on biolayer interferometry using a fortéBio Octet HTX instrument. EBOV GP ΔMuc protein was loaded onto HIS biosensors (AR2G, fortéBio) through amine coupling for 600 s. Biosensors were equilibrated for 120 s in 1% BSA in PBS (BSA-PBS) prior to capturing competitor mAbs. GP proteins were diluted to 10 μg/mL; mAbs KZ52, EVB100, EVB114, 13C6, and $IgG_1$ isotype control Ab were diluted to 35 μg/mL in BSA-PBS. Binding of competitor mAbs was assessed for 300 s followed by a brief equilibration for 60 s prior to binding assessment of probing mAbs. Binding of probing mAbs was assessed for 300 s. Percent inhibition (PI) of probing mAbs binding to GP by competitor mAbs was carried out by an equation: PI=100−[(probing mAb binding in the presence competitor mAb)/(probing mAb binding in the absence of competitor mAb)]×100. All the assays were performed in duplicate and with agitation set to 1,000 rpm at 30° C.

Animal Study and Safety.

Research was conducted under an IACUC-approved protocol in compliance with the Animal Welfare Act, PHS Policy, and other Federal statutes and regulations relating to animals and experiments involving animals. The facilities where this research was conducted are accredited by the Association for Assessment and Accreditation of Laboratory Animal Care, International and adhere to principles stated in the Guide for the Care and Use of Laboratory Animals, National Research Council, 2011. Animal study protocols were approved by both the Vaccine Research Center and United States Army Medical Research Institute of Infectious Diseases IACUCs. All animals were Vietnamese-origin rhesus macaques (*Macaca mulatta*), female, approximately 2-5 years of age and were obtained from Covance. Animals were randomly assigned to treatment groups based on sequential selection from a population inventory. Sample sizes of three animals per BSL4 EBOV challenge group provide 80% power to detect a difference in survival rates assuming 100% survival (3/3 treated survive) vs. 0% survival in negative controls at the 95% confidence level (1-tailed Fisher exact test). Prior to blood sampling or treatment, animals were anesthetized with ketamine or telazol.

Antibody Administration.

In the EVB100/EVB114 cocktail challenge, antibodies were mixed in PBS at 4 mg/mL of EVB100 and 46 mg/mL of EVB114 for a total antibody concentration of 50 mg/mL. In the second challenge, animals received 50 mg/mL of EVB114 in PBS. Antibodies were administered via intravenous injection in peripheral veins using ≤20 gauge butterfly needles over a period ≥15 minutes in a single bolus via syringe pump.

EBOV Challenge.

Animal studies conducted at USAMRIID were approved by the IACUC. Animals were transferred one week prior to challenge to the Bio-Safety Level-4 (BSL-4) facility for exposure to a lethal (1000 PFU) i.m. EBOV Kikwit variant challenge. Challenge studies included a single unvaccinated animal (control); the use of historical control (n>50) allows for one untreated control to be used in each challenge experiment. While at USAMRIID the monkeys were fed and checked daily. During the EBOV challenge study, blood was collected from the NHP for hematological, biochemical and virological analyses. Following the development of clinical signs, animals were checked multiple times daily. Institute scoring criteria were used to determine timing of humane euthanasia under anesthesia.

Detection of EBOV.

RNA was isolated from plasma of EBOV-exposed NHP by real time qPCR as described previously (Malhotra et al., *PLoS Negl. Trop. Dis.* 7, e2171, 2013). EDTA plasma was added to TriReagent LS (Sigma), 1 part to 3 parts, in preparation for qRT-PCR. Inactivated samples were Extracted and eluted with AVE Buffer (QIAGEN, Valencia, Calif.) using a QIAamp Viral RNA Mini Kit (Qiagen, Valencia, Calif.). All samples were run on an Applied Biosystems 7500 Fast Dx Real-Time PCR instrument (Life Technologies, Grand Island, N.Y.). Reactions were performed with SuperScript II One-Step RT-PCR System (Life Technologies, Grand Island, N.Y.) with additional MgSO4 added to a final concentration of 3.0 mM. All samples were run in triplicate 5 µL each. The average of the triplicates was multiplied by 200 to obtain genomes equivalents per mL, then multiplied by a dilution factor of 4 for the final reported value. The sequence of the primer and probes for the EBOV glycoprotein are described below. The genomic equivalents were determined using a synthetic RNA standard curve of known concentration. Forward primer: 5'-TTTTCAATCCT-CAACCGTAAGGC (SEQ ID NO: 63)—3'; REVERSE PRIMER: 5'-CAGTCCGGTCCCAGAATGTG (SEQ ID NO: 64)-3'; PROBE: 6FAM—CATGTGCCGC-CCCATCGCTGC (SEQ ID NO: 65)—TAMRA Example 2

Antibodies Specific to EBOV GP for Detecting EBOV in a Sample or a Subject

This example describes an exemplary use of EBOV monoclonal neutralizing antibodies specific to EBOV GP for the detection of EBOV in a sample or a subject. This example further describes the use of these antibodies to confirm the diagnosis of EBOV infection in a subject.

A biological sample, such as a blood sample, is obtained from the patient diagnosed with, undergoing screening for, or suspected of having, an EBOV infection. A blood sample can be taken from a patient who is not infected is used as a control, alternateively, a standard result can also be used as a control. An ELISA is performed to detect the presence of EBOV in the blood sample. Proteins present in the blood samples (the patient sample and control sample) are immobilized on a solid support, such as a 96-well plate, according to methods well known in the art (see, for example, Robinson et al., *Lancet* 362:1612-1616, 2003, incorporated herein by reference). Following immobilization, EBOV monoclonal neutralizing antibodies specific to EBOV GP that are directly labeled with a fluorescent marker are applied to the protein-immobilized plate. The plate is washed in an appropriate buffer, such as PBS, to remove any unbound antibody and to minimize non-specific binding of antibody. Fluorescence can be detected using a fluorometric plate reader according to standard methods. An increase in fluorescence intensity of the patient sample, relative to the control sample, indicates the EBOV GP antibody specifically bound proteins from the blood sample, thus detecting the presence of EBOV protein in the sample. Detection of EBOV protein in the patient sample indicates the patient has EBOV infection, or confirms diagnosis of EBOV in the subject.

Example 3

EBOV Monoclonal Neutralizing Antibodies Specific for EBOV GP for the Treatment of EBOV This example describes a particular method that can be used to treat EBOV infection in a human subject by administration of one or more EBOV GP-specific neutralizing antibodies or antigen binding fragments. Although particular methods, dosages, and modes of administrations are provided, one skilled in the art will appreciate that variations can be made without substantially affecting the treatment.

Screening Subjects

In particular examples, the subject is first screened to determine if they have an EBOV infection. Examples of methods that can be used to screen for EBOV infection include evaluating the patient for EBOV symptoms (e.g., hemorrhagic fever), determining prior exposure to EBOV infected subjects or EBOV materials (e.g., bodily fluids from an EBOV infected patient), and/or measuring the levels of one or more EBOV proteins or nucleic acid in a biological sample from the subject (e.g., assaying for EBOV sGP in a blood sample from the subject).

In some examples, EBOV testing consists of initial screening with an enzyme-linked immunosorbent assay (ELISA) to detect antibodies to an EBOV protein, such as to EBOV GP. Specimens with a reactive ELISA result are retested in duplicate. If the result of the duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered EBOV-positive and indicative of EBOV infection. In additional examples, nucleic acid testing (e.g., viral RNA or proviral DNA amplification method) can also help diagnosis in certain situations.

The detection of EBOV protein in a subject's blood is indicative that the subject is infected with EBOV and is a candidate for receiving the therapeutic compositions disclosed herein. However, pre-screening is not required prior to administration of the therapeutic compositions disclosed herein.

Administration of Therapeutic Compositions

Following subject selection, a therapeutically effective amount of an EBOV GP-specific neutralizing mAb described herein (e.g., EVB114 or EVB100) or a combination of such mAbs is administered to the subject (such as an adult human either at risk for contracting EBOV or known to be infected with EBOV). Additional agents, such as anti-viral agents, can also be administered to the subject simultaneously or prior to or following administration of the disclosed mAb. Typically the antibody is administered intravenously.

The amount of the antibody administered to prevent, reduce, inhibit, and/or treat EBOV or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., EBOV or EVD) in a subject without causing a substantial cytotoxic effect in the subject. An effective amount can be readily determined by one skilled in the art, for example using routine trials establishing dose response curves. As such, these compositions may be formulated with an inert diluent or with a pharmaceutically acceptable carrier.

In one specific example, a subject known to have an EBOV infection is administered 50 mg/kg of a disclosed antibody (or combination thereof) every day for 3 days following initial diagnosis of EBOV infection. In another example, the antibodies are administered continuously.

Assessment

Following the administration of one or more therapies, subjects with EBOV can be monitored for a reduction in EBOV levels (such as viral titer or the EBOV GP level in serum), or reductions in one or more clinical symptoms associated with EBOV infection. Subjects can be monitored using any method known in the art. For example, biological samples from the subject, including blood, can be obtained and alterations in EBOV levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in EBOV infection (e.g., as measured by EBOV GP level or viral titer in serum), EBOV replication, or combination thereof.

It will be apparent that the precise details of the methods or compositions described may be varied or modified without departing from the spirit of the described embodiments. We claim all such modifications and variations that fall within the scope and spirit of the claims below.

We claim:

1. An isolated monoclonal antibody, comprising:
a heavy chain variable region (V$_H$) comprising a heavy chain complementarity determining region (HCDR)1, a HCDR2, and a HCDR3 of the V$_H$ set forth as SEQ ID NO: 1 (EVB114 V$_H$), and a light chain variable region (V$_L$) comprising a light chain complementarity determining region (LCDR)1, a LCDR2, and a LCDR3 of the V$_L$ set forth as SEQ ID NO: 2 (EVB114 V$_L$); or
a V$_H$ comprising a HCDR1, a HCDR2, and a HCDR3 of the V$_H$ set forth as SEQ ID NO: 3 (EVB100 V$_H$), and a V$_L$ comprising a LCDR1, a LCDR2, and a LCDR3 of the V$_L$ set forth as SEQ ID NO: 4 (EVB100 V$_L$); and
wherein the monoclonal antibody or antigen binding fragment specifically binds to Ebola virus glycoprotein (GP).

2. The antibody of claim 1, wherein:
the HCDR1, the HCDR2, and the HCDR3 comprise amino acids 26-33, 51-57, and 96-108 of SEQ ID NO: 1, respectively, and the LCDR1, the LCDR2, and the LCDR3 comprise amino acids 27-32, 50-52, and 89-97 of SEQ ID NO: 2, respectively; or
the HCDR1, the HCDR2, and the HCDR3 comprise amino acids 26-33, 51-57, and 96-114 of SEQ ID NO: 3, respectively, and the LCDR1, the LCDR2, and the LCDR3 comprise amino acids 26-31, 49-51, and 88-95 of SEQ ID NO: 4, respectively.

3. The antibody of claim 1, wherein:
the V$_H$ comprises an amino acid sequence at least 80% identical to the sequence set forth as SEQ ID NO: 1 and/or the V$_L$ comprises an amino acid sequence at least 80% identical to the sequence set forth as SEQ ID NO: 2; or
the V$_H$ comprises an amino acid sequence at least 80% identical to the sequence set forth as SEQ ID NO: 3, and/or the V$_L$ comprises an amino acid sequence at least 80% identical to the sequence set forth as SEQ ID NO: 4.

4. The antibody of claim 1, wherein:
the V$_H$ comprises the amino acid sequence set forth as SEQ ID NO: 1, and/or the V$_L$ comprises the amino acid sequence set forth as SEQ ID NO: 2; or
the V$_H$ comprises the amino acid sequence set forth as SEQ ID NO: 3, and/or the V$_L$ comprises the amino acid sequence set forth as SEQ ID NO: 4.

5. The antibody of claim 1, wherein the V$_H$ and V$_L$ comprise or consist of the amino acid sequences set forth as SEQ ID NOs: 1 and 2, respectively, or SEQ ID NOs: 3 and 4, respectively.

6. The antibody of claim 1, comprising the V$_H$ comprising the HCDR1, the HCDR2, and the HCDR3 of the V$_H$ set forth as SEQ ID NO: 1, and the V$_L$ comprising the LCDR1, the LCDR2, and the LCDR3 of the V$_L$ set forth as SEQ ID NO: 2, and further comprising
a M31S substitution according to kabat positioning in the V$_H$;
a D30S substitution according to kabat positioning in the V$_L$; or
a M31S substitution according to kabat positioning in the V$_H$ and a D30S substitution according to kabat positioning in the V$_L$.

7. The antibody of claim 6, wherein the HCDR1, the HCDR2, the HCDR3, the LCDR1, the LCDR2, and the LCDR3 comprise SEQ ID NOs: 38, 33, 34, 35, 36, and 37, respectively, SEQ ID NOs: 32, 33, 34, 39, 36, and 37, respectively, or SEQ ID NOs: 38, 33, 34, 39, 36, and 37, respectively.

8. The antibody of claim 6, wherein the V$_H$ and the V$_L$ comprises the amino acid sequences set forth as SEQ ID NOs: 28 and 2, respectfully, SEQ ID NOs: 1 and 29, respectfully, or SEQ ID NOs: 28 and 29, respectfully.

9. The antibody of claim 1, comprising a human framework region.

10. The antibody of claim 1, comprising a human constant region.

11. The antibody of claim 1, wherein the antibody is an IgG, IgM or IgA.

12. The antibody of claim 1, wherein the antibody is an IgG1 and comprises a human constant region.

13. The antibody of claim 1, comprising a recombinant constant region comprising one or more modifications that increase binding to the neonatal Fc receptor and/or increase antibody-dependent cell cytotoxicity (ADCC).

14. The antibody of claim 13, wherein the antibody is a human IgG1 and comprises a recombinant constant region comprising M428L and N434S mutations to increase binding to the neonatal Fc receptor.

15. An antigen binding fragment that specifically binds to the extracellular domain Ebola virus GP, comprising the V$_H$ and the V$_L$ of the antibody of claim 1.

16. The antigen binding fragment of claim 15, wherein the antigen binding fragment is a Fv, Fab, F(ab')$_2$, scFV or a scFV$_2$ fragment.

17. A bispecific antibody that specifically binds to the extracellular domain Ebola virus GP, comprising the V$_H$ and the V$_L$ of the antibody of claim 1.

18. The antibody or antigen binding fragment of claim 1, wherein the monoclonal antibody or antigen binding fragment neutralizes Ebola virus.

19. The antibody or antigen binding fragment of claim 14, wherein the Ebola virus is Zaire Ebola virus.

20. The antibody or antigen binding fragment of claim 1, wherein the Ebola virus GP is a Zaire Ebola virus GP.

21. The antibody or antigen binding fragment of claim 16, wherein the Zaire Ebola virus GP comprises the amino acid sequence set forth as SEQ ID NO: 15.

22. The antibody or antigen binding fragment of claim 1, linked to an effector molecule or a detectable marker.

23. The antibody or antigen binding fragment of claim 22, wherein the detectable marker is a fluorescent, enzymatic, or radioactive marker.

24. An antibody or an antigen binding fragment thereof that binds to the same epitope as the antibody of claim 1, wherein the antibody or antigen binding fragment thereof neutralizes Ebola virus.

25. An isolated nucleic acid molecule encoding the $V_H$ and/or the $V_L$ of the antibody or antigen binding fragment of claim 1.

26. The nucleic acid molecule of claim 25, wherein the nucleic acid molecule is a recombinant nucleic acid molecule.

27. The nucleic acid molecule of claim 25, comprising a cDNA molecule encoding the antibody or antigen binding fragment.

28. The nucleic acid molecule of claim 25, wherein the $V_H$ and/or the $V_L$ of the antibody or antigen binding fragment comprise the nucleic acid sequences set forth as
SEQ ID NOs: 7 and 8, respectively, or degenerate variants thereof; or
SEQ ID NOs: 9 and 10, respectively, or degenerate variants thereof.

29. The nucleic acid molecule of claim 25, operably linked to a promoter.

30. An expression vector comprising the nucleic acid molecule of claim 25.

31. A pharmaceutical composition for use in treating or inhibiting an Ebola virus infection, comprising:
a therapeutically effective amount of the antibody of claim 1, an antigen binding fragment thereof, a nucleic acid molecule encoding the antibody or antigen binding fragment, or an expression vector comprising the nucleic acid molecule; and
a pharmaceutically acceptable carrier.

32. The pharmaceutical composition of claim 31, wherein the composition is sterile and/or is in unit dosage form or a multiple thereof.

33. A method of detecting an Ebola virus infection in a subject, comprising:
contacting a biological sample from the subject with the antibody of claim 1 or an antigen binding fragment thereof under conditions sufficient to form an immune complex; and
detecting the presence of the immune complex on the sample, wherein the presence of the immune complex on the sample indicates that the subject has the Ebola virus infection.

34. A method of preventing or treating an Ebola virus infection in a subject, comprising administering to the subject a therapeutically effective amount of the antibody of claim 1, an antigen binding fragment thereof, a nucleic acid molecule encoding the antibody or antigen binding fragment, or an expression vector comprising the nucleic acid molecule, thereby preventing or treating the Ebola virus infection.

35. The method of claim 34, further comprising administering to the subject one or more additional antibodies or antigen binding fragments that specifically bind to Ebola virus GP and neutralize Ebola virus, or one or more nucleic acid molecules encoding the additional antibodies or antigen binding fragments.

36. The method of 35, comprising administering to the subject a pharmaceutical composition comprising a first antibody and a second antibody, wherein
the first antibody comprises the $V_H$ comprising the HCDR1, the HCDR2, and the HCDR3 of the $V_H$ set forth as SEQ ID NO: 1, and the $V_L$ comprising the LCDR1, the LCDR2, and the LCDR3 of the $V_L$ set forth as SEQ ID NO: 2; and
the second antibody comprises the $V_H$ comprising the HCDR1, the HCDR2, and the HCDR3 of the $V_H$ set forth as SEQ ID NO: 3, and the $V_L$ comprising the LCDR1, the LCDR2, and the LCDR3 of the $V_L$ set forth as SEQ ID NO: 4.

37. The method of claim 36, wherein the first antibody comprises the $V_H$ and $V_L$ set forth as SEQ ID NOs: 1 and 2, respectively, and the second antibody comprises the $V_H$ and $V_L$ set forth as SEQ ID NOs: 3 and 4, respectively.

38. The method of claim 34, wherein the Ebola virus is Ebola virus Zaire.

39. A method of producing an antibody or antigen binding fragment that specifically binds to Ebola virus GP, comprising:
expressing in a host cell:
one or more nucleic acid molecules encoding antibody heavy and light chains comprising the $V_H$ and the $V_L$ of the antibody of claim 1; or
one or more nucleic acid molecules encoding an antigen binding fragment comprising the $V_H$ and the $V_L$; and
purifying the antibody or antigen binding fragment;
thereby producing the antibody or antigen binding fragment.

* * * * *

SEQUENCE LISTING

```
<160> NUMBER OF SEQ ID NOS: 66

<210> SEQ ID NO 1
<211> LENGTH: 119
<212> TYPE: PRT
<213> ORGANISM: homo sapiens

<400> SEQUENCE: 1

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ala Leu Arg Met Tyr
            20                  25                  30

Asp Met His Trp Val Arg Gln Thr Ile Asp Lys Arg Leu Glu Trp Val
        35                  40                  45

Ser Ala Val Gly Pro Ser Gly Asp Thr Tyr Tyr Ala Asp Ser Val Lys
    50                  55                  60

Gly Arg Phe Ala Val Ser Arg Glu Asn Ala Lys Asn Ser Leu Ser Leu
65                  70                  75                  80

Gln Met Asn Ser Leu Thr Ala Gly Asp Thr Ala Ile Tyr Tyr Cys Val
                85                  90                  95

Arg Ser Asp Arg Gly Val Ala Gly Leu Phe Asp Ser Trp Gly Gln Gly
            100                 105                 110

Ile Leu Val Thr Val Ser Ser
        115

<210> SEQ ID NO 2
<211> LENGTH: 107
<212> TYPE: PRT
<213> ORGANISM: homo sapiens

<400> SEQUENCE: 2

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ala Phe Asp Asn Tyr
            20                  25                  30

Val Ala Trp Tyr Gln Gln Arg Pro Gly Lys Val Pro Lys Leu Leu Ile
        35                  40                  45

Ser Ala Ala Ser Ala Leu His Ala Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Leu
                85                  90                  95

Thr Phe Gly Gly Gly Thr Lys Val Glu Ile Lys
            100                 105
```

-continued

```
<210> SEQ ID NO 3
<211> LENGTH: 125
<212> TYPE: PRT
<213> ORGANISM: homo sapiens

<400> SEQUENCE: 3
```

Gln Val Gln Leu Gln Glu Ser Gly Pro Gly Leu Val Lys Pro Ser Asp
1               5                   10                  15

Thr Leu Ser Leu Thr Cys Thr Val Ser Gly Gly Ser Leu Ser Ser Phe
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Pro Asn Tyr Ser Pro Ser Leu Glu
    50                  55                  60

Ser Arg Val Thr Met Ser Val Asp Thr Thr Arg Asn Gln Ile Ser Leu
65                  70                  75                  80

Lys Leu Asp Ser Val Thr Ala Ala Asp Thr Ala Val Tyr Tyr Cys Val
                85                  90                  95

Arg Ala Ser Arg Ser Tyr Tyr Trp Gly Ser Tyr Arg Pro Thr Ala Phe
            100                 105                 110

Asp Ser Trp Gly Gln Gly Thr Leu Val Thr Val Ser Ser
        115                 120                 125

```
<210> SEQ ID NO 4
<211> LENGTH: 105
<212> TYPE: PRT
<213> ORGANISM: homo sapiens

<400> SEQUENCE: 4
```

Ser Tyr Glu Leu Thr Gln Pro Leu Ser Val Ser Val Ser Pro Gly Gln
1               5                   10                  15

Thr Ala Ile Phe Thr Cys Ser Gly Asp Asn Leu Gly Asp Lys Tyr Val
            20                  25                  30

Cys Trp Phe Gln Gln Arg Pro Gly Gln Ser Pro Met Leu Leu Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ser Thr
65                  70                  75                  80

Asp Glu Ala Asp Tyr Tyr Cys Gln Thr Trp Asp Ser Thr Val Val Phe
                85                  90                  95

Gly Gly Gly Thr Lys Leu Thr Val Leu
            100                 105

```
<210> SEQ ID NO 5
<211> LENGTH: 123
<212> TYPE: PRT
<213> ORGANISM: homo sapiens

<400> SEQUENCE: 5
```

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Leu Ser Asn Tyr
            20                  25                  30

Ala Ile Ser Trp Val Arg Gln Ala Pro Gly Gln Gly Leu Glu Trp Met
        35                  40                  45

Gly Gly Thr Ile Pro Thr Leu Gly Met Ser Thr Tyr Ala Pro Asn Phe
    50                  55                  60

Gln Gly Arg Val Ala Ile Thr Ala Asp Lys Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Thr Met Gly Ser Ala Asp Thr Ser Phe Tyr Phe Tyr Met Asp Val
            100                 105                 110

Trp Gly Lys Gly Thr Thr Val Thr Val Ser Ser
        115                 120

<210> SEQ ID NO 6
<211> LENGTH: 108
<212> TYPE: PRT
<213> ORGANISM: homo sapiens

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Tyr Ser Pro
                85                  90                  95

Phe Thr Phe Gly Pro Gly Thr Lys Val Asp Ile Lys
            100                 105

<210> SEQ ID NO 7
<211> LENGTH: 358
<212> TYPE: DNA
<213> ORGANISM: homo sapiens

<400> SEQUENCE: 7
gaggtgcagc tggtggagtc tgggggaggt ttaattcagc cggggggtc cctgagactc      60 tcctgtgcag cctctggatt cgccctcaga atgtacgaca tgcactgggt ccgtcagaca     120
atagataaac gtctcgagtg gtctcagct gtgggtcctt ctggtgacac ctactatgca     180
gactccgtga agggccgatt cgccgtctcc agagagaatg ccaagaactc cttgtctctt     240
cagatgaaca gcctgacagc cggggacacg gctatatact attgtgtaag gtctgaccga     300
ggagtggctg ccttttttga cagctggggc cagggaatcc tggtcaccgt ctcttcag      358

<210> SEQ ID NO 8
<211> LENGTH: 322
<212> TYPE: DNA
<213> ORGANISM: homo sapiens

<400> SEQUENCE: 8
gacatccaga tgacccagtc tccatcatcc ctgtctgcat ctgtgggaga cagaatcacc      60
atcacttgcc gggcgagtca ggcctttgac aattatgtag cctggtatca acagagacca     120
gggaaggttc ctaagctcct gatctctgct gcatccgctt tgcacgcagg ggtcccatct     180
cgcttcagcg gcagtggctc tgggacacat ttcactctca ccatcagcag cctgcagcct     240
gaagatgttg caacttatta ctgtcaaaac tataacagtg ccccgctcac tttcggcgga     300

```
gggaccaagg tggagatcaa ac                                              322

<210> SEQ ID NO 9
<211> LENGTH: 376
<212> TYPE: DNA
<213> ORGANISM: homo sapiens

<400> SEQUENCE: 9
caggtgcagc tgcaggagtc gggcccagga ctggtgaagc cttcggatac cctgtccctc       60
acctgtactg tctctggtgg ctccctcagt agtttctact ggagctggat ccggcagccc      120
ccagggaagg gactggagtg gattgggtat atctattaca gtgggagccc caactacagc      180
ccctccctcg agagtcgagt caccatgtca gtagacacga ccaggaacca gatctccctg      240
aagttggact ctgtgaccgc ggcggacacg gccgtgtatt actgtgtgag agcctcccga      300
agttactatt gggggagtta tcgcccaacg gcttttgact cctggggcca gggaaccctg      360
gtcaccgtct cctcag                                                     376

<210> SEQ ID NO 10
<211> LENGTH: 316
<212> TYPE: DNA
<213> ORGANISM: homo sapiens

<400> SEQUENCE: 10
tcctatgagc tgactcagcc actctcagtg tccgtgtccc caggccagac agccatcttc       60
acctgctctg gagataattt gggggataag tatgtttgct ggtttcaaca gaggccaggc      120
cagtccccta tgctgctcat ctatcaagac aataagcggc cctcggggat ccctgagcga      180
ttctctggct ccaactctgg gaacacagcc actctgacta tcagcgggac ccagtctaca      240
gatgaggctg actattactg tcagacgtgg gacagcaccg tggtgttcgg cggagggacc      300
aaactgaccg tcctgg                                                     316

<210> SEQ ID NO 11
<211> LENGTH: 370
<212> TYPE: DNA
<213> ORGANISM: homo sapiens

<400> SEQUENCE: 11
caggtccagc tggtgcagtc tggggctgag gtgaagaagc ctgggtcctc ggtgaaagtc       60
tcctgcaaga cttctggagg caccctcagc aactatgcta tcagctgggt gcgacaggcc      120
cctggacaag gccttgagtg gatgggaggc accattccta cccttggtat gtccacctac      180
gcaccgaact tccagggcag agtcgcgatt accgcggaca aatccacgag cacagcctac      240
atggagttga gtagtctgag gtctgacgac acggccgttt attattgtgc gactatgggc      300
agtgcggaca ctagtttcta cttctacatg gacgtctggg gcaaagggac cacggtcacc      360
gtctcctcag                                                            370

<210> SEQ ID NO 12
<211> LENGTH: 325
<212> TYPE: DNA
<213> ORGANISM: homo sapiens

<400> SEQUENCE: 12
gaaattgtgt tgacgcagtc tccaggcacc ctgtctttgt ctccagggga gagagccacc       60
ctctcctgca gggccagtca gagtgttagt agcagctact tagcctggta ccagcagaaa      120
```

```
cctggccagg ctcccagact cctcatctat ggtacatcca gcagggccac tggcatccca       180
gacaggttca gtggcagtgc gtctgggaca gacttcactc tcaccatcag cagactggag       240
cctgaagatt ttgcagtgta ttactgtcag cagtatgctt actcaccatt cactttcggc       300
cctgggacca cagtggatat caaac                                             325
```

<210> SEQ ID NO 13
<211> LENGTH: 676
<212> TYPE: PRT
<213> ORGANISM: Ebola virus

<400> SEQUENCE: 13

```
Met Val Thr Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Pro
            20                  25                  30

Ile Pro Leu Gly Val Val His Asn Asn Thr Leu Gln Val Ser Asp Ile
        35                  40                  45

Asp Lys Leu Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Tyr Glu Ala Gly Glu Trp Ala Glu Asn Cys Tyr Asn Leu Asp
            100                 105                 110

Ile Lys Lys Ala Asp Gly Ser Glu Cys Leu Pro Glu Ala Pro Glu Gly
        115                 120                 125

Val Arg Gly Phe Pro Arg Cys Arg Tyr Val His Lys Val Ser Gly Thr
    130                 135                 140

Gly Pro Cys Pro Glu Gly Tyr Ala Phe His Lys Glu Gly Ala Phe Phe
145                 150                 155                 160

Leu Tyr Asp Arg Leu Ala Ser Thr Ile Ile Tyr Arg Ser Thr Thr Phe
                165                 170                 175

Ser Glu Gly Val Val Ala Phe Leu Ile Leu Pro Glu Thr Lys Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Val Thr Leu Asn Tyr Val Ala Asp Asn
    210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
                245                 250                 255

Asn Glu Thr Ile Tyr Thr Asn Gly Arg Arg Ser Asn Thr Thr Gly Thr
            260                 265                 270

Leu Ile Trp Lys Val Asn Pro Thr Val Asp Thr Gly Val Gly Glu Trp
        275                 280                 285

Ala Phe Trp Glu Asn Lys Lys Asn Phe Thr Lys Thr Leu Ser Ser Glu
    290                 295                 300

Glu Leu Ser Val Ile Phe Val Pro Arg Ala Gln Asp Pro Gly Ser Asn
305                 310                 315                 320

Gln Lys Thr Lys Val Thr Pro Ser Phe Ala Asn Asn Gln Thr Ser
                325                 330                 335
```

```
Lys Asn His Glu Asp Leu Val Pro Glu Asp Pro Ala Ser Val Val Gln
            340                 345                 350

Val Arg Asp Leu Gln Arg Glu Asn Thr Val Pro Thr Pro Pro Pro Asp
        355                 360                 365

Thr Val Pro Thr Thr Leu Ile Pro Asp Thr Met Glu Glu Gln Thr Thr
    370                 375                 380

Ser His Tyr Glu Pro Pro Asn Ile Ser Arg Asn His Gln Glu Arg Asn
385                 390                 395                 400

Asn Thr Ala His Pro Glu Thr Leu Ala Asn Asn Pro Pro Asp Asn Thr
                405                 410                 415

Thr Pro Ser Thr Pro Pro Gln Asp Gly Glu Arg Thr Ser Ser His Thr
            420                 425                 430

Thr Pro Ser Pro Arg Pro Val Pro Thr Ser Thr Ile His Pro Thr Thr
        435                 440                 445

Arg Glu Thr His Ile Pro Thr Thr Met Thr Thr Ser His Asp Thr Asp
    450                 455                 460

Ser Asn Arg Pro Asn Pro Ile Asp Ile Ser Glu Ser Thr Glu Pro Gly
465                 470                 475                 480

Pro Leu Thr Asn Thr Thr Arg Gly Ala Ala Asn Leu Leu Thr Gly Ser
                485                 490                 495

Arg Arg Thr Arg Arg Glu Ile Thr Leu Arg Thr Gln Ala Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Ile Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Ile Asp Lys Pro Leu Pro Asp Gln Thr Asp
625                 630                 635                 640

Asn Asp Asn Trp Trp Thr Gly Trp Arg Gln Trp Val Pro Ala Gly Ile
                645                 650                 655

Gly Ile Thr Gly Val Ile Ile Ala Val Ile Ala Leu Leu Cys Ile Cys
            660                 665                 670

Lys Phe Leu Leu
        675

<210> SEQ ID NO 14
<211> LENGTH: 676
<212> TYPE: PRT
<213> ORGANISM: Ebola virus

<400> SEQUENCE: 14

Met Glu Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30
```

```
Met Pro Leu Gly Val Val Thr Asn Ser Thr Leu Glu Val Thr Glu Ile
         35                  40                  45

Asp Gln Leu Val Cys Lys Asp His Leu Ala Ser Thr Asp Gln Leu Lys
     50                  55                  60

Ser Val Gly Leu Asn Leu Glu Gly Ser Gly Val Ser Thr Asp Ile Pro
 65                  70                  75                  80

Ser Ala Thr Lys Arg Trp Gly Phe Arg Ser Gly Val Pro Pro Lys Val
                 85                  90                  95

Phe Ser Tyr Glu Ala Gly Glu Trp Ala Glu Asn Cys Tyr Asn Leu Glu
                100                 105                 110

Ile Lys Lys Pro Asp Gly Ser Glu Cys Leu Pro Pro Pro Asp Gly
             115                 120                 125

Val Arg Gly Phe Pro Arg Cys Arg Tyr Val His Lys Ala Gln Gly Thr
         130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
             180                 185                 190

Phe Leu Gln Ser Pro Pro Ile Arg Glu Ala Val Asn Tyr Thr Glu Asn
         195                 200                 205

Thr Ser Ser Tyr Tyr Ala Thr Ser Tyr Leu Glu Tyr Glu Ile Glu Asn
     210                 215                 220

Phe Gly Ala Gln His Ser Thr Thr Leu Phe Lys Ile Asn Asn Asn Thr
225                 230                 235                 240

Phe Val Leu Leu Asp Arg Pro His Thr Pro Gln Phe Leu Phe Gln Leu
                245                 250                 255

Asn Asp Thr Ile His Leu His Gln Gln Leu Ser Asn Thr Thr Gly Lys
             260                 265                 270

Leu Ile Trp Thr Leu Asp Ala Asn Ile Asn Ala Asp Ile Gly Glu Trp
         275                 280                 285

Ala Phe Trp Glu Asn Lys Lys Asn Leu Ser Glu Gln Leu Arg Gly Glu
     290                 295                 300

Glu Leu Ser Phe Glu Thr Leu Ser Leu Asn Glu Thr Glu Asp Asp Asp
305                 310                 315                 320

Ala Thr Ser Ser Arg Thr Thr Lys Gly Arg Ile Ser Asp Arg Ala Thr
                325                 330                 335

Arg Lys Tyr Ser Asp Leu Val Pro Lys Asp Ser Pro Gly Met Val Ser
             340                 345                 350

Leu His Val Pro Glu Gly Glu Thr Thr Leu Pro Ser Gln Asn Ser Thr
         355                 360                 365

Glu Gly Arg Arg Val Asp Val Asn Thr Gln Glu Thr Ile Thr Glu Thr
     370                 375                 380

Thr Ala Thr Ile Ile Gly Thr Asn Gly Asn Asn Met Gln Ile Ser Thr
385                 390                 395                 400

Ile Gly Thr Gly Leu Ser Ser Ser Gln Ile Leu Ser Ser Ser Pro Thr
                405                 410                 415

Met Ala Pro Ser Pro Glu Thr Gln Thr Ser Thr Tyr Thr Pro Lys
             420                 425                 430

Leu Pro Val Met Thr Thr Glu Glu Ser Thr Thr Pro Pro Arg Asn Ser
         435                 440                 445
```

```
Pro Gly Ser Thr Thr Glu Ala Pro Thr Leu Thr Thr Pro Glu Asn Ile
    450                 455                 460
Thr Thr Ala Val Lys Thr Val Leu Pro Gln Glu Ser Thr Ser Asn Gly
465                 470                 475                 480
Leu Ile Thr Ser Thr Val Thr Gly Ile Leu Gly Ser Leu Gly Leu Arg
                485                 490                 495
Lys Arg Ser Arg Arg Gln Val Asn Thr Arg Ala Thr Gly Lys Cys Asn
                500                 505                 510
Pro Asn Leu His Tyr Trp Thr Ala Gln Glu Gln His Asn Ala Ala Gly
            515                 520                 525
Ile Ala Trp Ile Pro Tyr Phe Gly Pro Gly Ala Glu Gly Ile Tyr Thr
530                 535                 540
Glu Gly Leu Met His Asn Gln Asn Ala Leu Val Cys Gly Leu Arg Gln
545                 550                 555                 560
Leu Ala Asn Glu Thr Thr Gln Ala Leu Gln Leu Phe Leu Arg Ala Thr
                565                 570                 575
Thr Glu Leu Arg Thr Tyr Thr Ile Leu Asn Arg Lys Ala Ile Asp Phe
                580                 585                 590
Leu Leu Arg Arg Trp Gly Gly Thr Cys Arg Ile Leu Gly Pro Asp Cys
            595                 600                 605
Cys Ile Glu Pro His Asp Trp Thr Lys Asn Ile Thr Asp Lys Ile Asn
610                 615                 620
Gln Ile Ile His Asp Phe Ile Asp Asn Pro Leu Pro Asn Gln Asp Asn
625                 630                 635                 640
Asp Asp Asn Trp Trp Thr Gly Trp Arg Gln Trp Ile Pro Ala Gly Ile
                645                 650                 655
Gly Ile Thr Gly Ile Ile Ile Ala Ile Ile Ala Leu Leu Cys Val Cys
            660                 665                 670
Lys Leu Leu Cys
        675

<210> SEQ ID NO 15
<211> LENGTH: 676
<212> TYPE: PRT
<213> ORGANISM: Ebola virus

<400> SEQUENCE: 15

Met Gly Val Thr Gly Ile Leu Gln Leu Pro Arg Asp Arg Phe Lys Lys
1               5                   10                  15
Thr Ser Phe Phe Leu Trp Val Ile Ile Leu Phe Gln Arg Thr Phe Ser
                20                  25                  30
Ile Pro Leu Gly Val Ile His Asn Ser Thr Leu Gln Val Ser Asp Val
            35                  40                  45
Asp Lys Leu Val Cys Arg Asp Lys Leu Ser Ser Thr Asn Gln Leu Arg
        50                  55                  60
Ser Val Gly Leu Asn Leu Glu Gly Asn Gly Val Ala Thr Asp Val Pro
65                  70                  75                  80
Ser Ala Thr Lys Arg Trp Gly Phe Arg Ser Gly Val Pro Pro Lys Val
                85                  90                  95
Val Asn Tyr Glu Ala Gly Glu Trp Ala Glu Asn Cys Tyr Asn Leu Glu
            100                 105                 110
Ile Lys Lys Pro Asp Gly Ser Glu Cys Leu Pro Ala Ala Pro Asp Gly
        115                 120                 125
Ile Arg Gly Phe Pro Arg Cys Arg Tyr Val His Lys Val Ser Gly Thr
    130                 135                 140
```

```
Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
            165                 170                 175

Ala Glu Gly Val Val Ala Phe Leu Ile Leu Pro Gln Ala Lys Lys Asp
        180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
        210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
            275                 280                 285

Ala Phe Trp Glu Thr Lys Lys Asn Leu Thr Arg Lys Ile Arg Ser Glu
290                 295                 300

Glu Leu Ser Phe Thr Ala Val Ser Asn Arg Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
            355                 360                 365

Ala Thr Ile Ser Thr Ser Pro Gln Pro Pro Thr Thr Lys Pro Gly Pro
        370                 375                 380

Asp Asn Ser Thr His Asn Thr Pro Val Tyr Lys Leu Asp Ile Ser Glu
385                 390                 395                 400

Ala Thr Gln Ala Glu Gln His His Arg Arg Thr Asp Asn Asp Ser Thr
                405                 410                 415

Thr Ser Asp Thr Pro Pro Ala Met Thr Ala Ala Gly Pro Pro Lys Ala
            420                 425                 430

Glu Asn Thr Asn Thr Ser Lys Gly Thr Asp Leu Pro Asp Pro Ala Thr
            435                 440                 445

Thr Thr Ser Pro Gln Asn His Ser Glu Thr Ala Gly Asn Asn Asn Thr
        450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
        530                 535                 540

Glu Gly Leu Met His Asn Gln Asp Gly Leu Ile Cys Gly Leu Arg Gln
545                 550                 555                 560
```

```
Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
                660                 665                 670

Lys Phe Val Phe
            675

<210> SEQ ID NO 16
<211> LENGTH: 677
<212> TYPE: PRT
<213> ORGANISM: Ebola virus

<400> SEQUENCE: 16

Met Gly Ser Gly Tyr Gln Leu Leu Gln Leu Pro Arg Glu Arg Phe Arg
1               5                   10                  15

Lys Thr Ser Phe Leu Val Trp Val Ile Ile Leu Phe Gln Arg Ala Ile
                20                  25                  30

Ser Met Pro Leu Gly Ile Val Thr Asn Ser Thr Leu Lys Ala Thr Glu
            35                  40                  45

Ile Asp Gln Leu Val Cys Arg Asp Lys Leu Ser Ser Thr Ser Gln Leu
        50                  55                  60

Lys Ser Val Gly Leu Asn Leu Glu Gly Asn Gly Ile Ala Thr Asp Val
65                  70                  75                  80

Pro Ser Ala Thr Lys Arg Trp Gly Phe Arg Ser Gly Val Pro Pro Lys
                85                  90                  95

Val Val Ser Tyr Glu Ala Gly Glu Trp Ala Glu Asn Cys Tyr Asn Leu
                100                 105                 110

Glu Ile Lys Lys Ser Asp Gly Ser Glu Cys Leu Pro Leu Pro Pro Asp
            115                 120                 125

Gly Val Arg Gly Phe Pro Arg Cys Arg Tyr Val His Lys Val Gln Gly
        130                 135                 140

Thr Gly Pro Cys Pro Gly Asp Leu Ala Phe His Lys Asn Gly Ala Phe
145                 150                 155                 160

Phe Leu Tyr Asp Arg Leu Ala Ser Thr Val Ile Tyr Arg Gly Thr Thr
                165                 170                 175

Phe Thr Glu Gly Val Val Ala Phe Leu Ile Leu Ser Glu Pro Lys Lys
                180                 185                 190

His Phe Trp Lys Ala Thr Pro Ala His Glu Pro Val Asn Thr Thr Asp
            195                 200                 205

Asp Ser Thr Ser Tyr Tyr Met Thr Leu Thr Leu Ser Tyr Glu Met Ser
        210                 215                 220

Asn Phe Gly Gly Lys Glu Ser Asn Thr Leu Phe Lys Val Asp Asn His
225                 230                 235                 240

Thr Tyr Val Gln Leu Asp Arg Pro His Thr Pro Gln Phe Leu Val Gln
                245                 250                 255
```

```
Leu Asn Glu Thr Leu Arg Arg Asn Asn Arg Leu Ser Asn Ser Thr Gly
            260                 265                 270

Arg Leu Thr Trp Thr Leu Asp Pro Lys Ile Glu Pro Asp Val Gly Glu
        275                 280                 285

Trp Ala Phe Trp Glu Thr Lys Lys Asn Phe Ser Gln Gln Leu His Gly
        290                 295                 300

Glu Asn Leu His Phe Gln Ile Leu Ser Thr His Thr Asn Asn Ser Ser
305                 310                 315                 320

Asp Gln Ser Pro Ala Gly Thr Val Gln Gly Lys Ile Ser Tyr His Pro
                325                 330                 335

Pro Thr Asn Asn Ser Glu Leu Val Pro Thr Asp Ser Pro Val Val
            340                 345                 350

Ser Val Leu Thr Ala Gly Arg Thr Glu Glu Met Ser Thr Gln Gly Leu
        355                 360                 365

Thr Asn Gly Glu Thr Ile Thr Gly Phe Thr Ala Asn Pro Met Thr Thr
    370                 375                 380

Thr Ile Ala Pro Ser Pro Thr Met Thr Ser Glu Val Asp Asn Asn Val
385                 390                 395                 400

Pro Ser Glu Gln Pro Asn Asn Thr Ala Ser Ile Glu Asp Ser Pro Pro
                405                 410                 415

Ser Ala Ser Asn Glu Thr Ile Asp His Ser Glu Met Asn Pro Ile Gln
            420                 425                 430

Gly Ser Asn Asn Ser Ala Gln Ser Pro Gln Thr Lys Thr Thr Pro Ala
        435                 440                 445

Pro Thr Ala Ser Pro Met Thr Gln Asp Pro Gln Glu Thr Ala Asn Ser
    450                 455                 460

Ser Lys Leu Gly Thr Ser Pro Gly Ser Ala Ala Glu Pro Ser Gln Pro
465                 470                 475                 480

Gly Phe Thr Ile Asn Thr Val Ser Lys Val Ala Asp Ser Leu Ser Pro
                485                 490                 495

Thr Arg Lys Gln Lys Arg Ser Val Arg Gln Asn Thr Ala Asn Lys Cys
            500                 505                 510

Asn Pro Asp Leu His Tyr Trp Thr Ala Val Asp Glu Gly Ala Ala Val
        515                 520                 525

Gly Leu Ala Trp Ile Pro Tyr Phe Gly Pro Ala Ala Glu Gly Ile Tyr
    530                 535                 540

Ile Glu Gly Val Met His Asn Gln Asn Gly Leu Ile Cys Gly Leu Arg
545                 550                 555                 560

Gln Leu Ala Asn Glu Thr Thr Gln Ala Leu Gln Leu Phe Leu Arg Ala
                565                 570                 575

Thr Thr Glu Leu Arg Thr Tyr Ser Leu Leu Asn Arg Lys Ala Ile Asp
            580                 585                 590

Phe Leu Leu Gln Arg Trp Gly Gly Thr Cys Arg Ile Leu Gly Pro Ser
        595                 600                 605

Cys Cys Ile Glu Pro His Asp Trp Thr Lys Asn Ile Thr Asp Glu Ile
    610                 615                 620

Asn Gln Ile Lys His Asp Phe Ile Asp Asn Pro Leu Pro Asp His Gly
625                 630                 635                 640

Asp Asp Leu Asn Leu Trp Thr Gly Trp Arg Gln Trp Ile Pro Ala Gly
                645                 650                 655

Ile Gly Ile Ile Gly Val Ile Ile Ala Ile Ala Leu Leu Cys Ile
            660                 665                 670
```

```
Cys Lys Ile Leu Cys
        675

<210> SEQ ID NO 17
<211> LENGTH: 676
<212> TYPE: PRT
<213> ORGANISM: Ebola virus

<400> SEQUENCE: 17

Met Gly Ala Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Ser
            20                  25                  30

Ile Pro Leu Gly Val Val His Asn Asn Thr Leu Gln Val Ser Asp Ile
        35                  40                  45

Asp Lys Phe Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
        115                 120                 125

Val Arg Asp Phe Pro Arg Cys Arg Tyr Val His Lys Val Ser Gly Thr
    130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175

Ala Glu Gly Val Ile Ala Phe Leu Ile Leu Pro Lys Ala Arg Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Thr Ile Asn Tyr Val Val Asp Asn
    210                 215                 220

Phe Gly Thr Asn Thr Thr Glu Phe Leu Phe Gln Val Asp His Leu Thr
225                 230                 235                 240

Tyr Val Gln Leu Glu Ala Arg Phe Thr Pro Gln Phe Leu Val Leu Leu
                245                 250                 255

Asn Glu Thr Ile Tyr Ser Asp Asn Arg Arg Ser Asn Thr Thr Gly Lys
            260                 265                 270

Leu Ile Trp Lys Ile Asn Pro Thr Val Asp Thr Ser Met Gly Glu Trp
        275                 280                 285

Ala Phe Trp Glu Asn Lys Lys Asn Phe Thr Lys Thr Leu Ser Ser Glu
    290                 295                 300

Glu Leu Ser Phe Val Pro Val Pro Glu Thr Gln Asn Gln Val Leu Asp
305                 310                 315                 320

Thr Thr Ala Thr Val Ser Pro Pro Ile Ser Ala His Asn His Ala Ala
                325                 330                 335

Glu Asp His Lys Glu Leu Val Ser Glu Asp Ser Thr Pro Val Val Gln
            340                 345                 350

Met Gln Asn Ile Lys Gly Lys Asp Thr Met Pro Thr Thr Val Thr Gly
        355                 360                 365
```

Val Pro Thr Thr Thr Pro Ser Pro Phe Pro Ile Asn Ala Arg Asn Thr
            370                 375                 380

Asp His Thr Lys Ser Phe Ile Gly Leu Glu Gly Pro Gln Glu Asp His
385                 390                 395                 400

Ser Thr Thr Gln Pro Ala Lys Thr Thr Ser Gln Pro Thr Asn Ser Thr
                405                 410                 415

Glu Ser Thr Thr Leu Asn Pro Thr Ser Glu Pro Ser Ser Arg Gly Thr
            420                 425                 430

Gly Pro Ser Ser Pro Thr Val Pro Asn Thr Thr Glu Ser His Ala Glu
                435                 440                 445

Leu Gly Lys Thr Thr Pro Thr Thr Leu Pro Glu Gln His Thr Ala Ala
            450                 455                 460

Ser Ala Ile Pro Arg Ala Val His Pro Asp Glu Leu Ser Gly Pro Gly
465                 470                 475                 480

Phe Leu Thr Asn Thr Ile Arg Gly Val Thr Asn Leu Leu Thr Gly Ser
                485                 490                 495

Arg Arg Lys Arg Arg Asp Val Thr Pro Asn Thr Gln Pro Lys Cys Asn
                500                 505                 510

Pro Asn Leu His Tyr Trp Thr Ala Leu Asp Glu Gly Ala Ala Ile Gly
            515                 520                 525

Leu Ala Trp Ile Pro Tyr Phe Gly Pro Ala Ala Glu Gly Ile Tyr Thr
            530                 535                 540

Glu Gly Ile Met Glu Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro Gln Asp Trp Thr Lys Asn Ile Thr Asp Lys Ile Asp
            610                 615                 620

Gln Ile Ile His Asp Phe Val Asp Asn Leu Pro Asn Gln Asn Asp
625                 630                 635                 640

Gly Ser Asn Trp Trp Thr Gly Trp Lys Gln Trp Val Pro Ala Gly Ile
                645                 650                 655

Gly Ile Thr Gly Val Ile Ile Ala Ile Ala Leu Leu Cys Ile Cys
                660                 665                 670

Lys Phe Met Leu
            675

<210> SEQ ID NO 18
<211> LENGTH: 364
<212> TYPE: PRT
<213> ORGANISM: Ebola virus

<400> SEQUENCE: 18

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg

```
            50                  55                  60
Ser Val Gly Leu Asn Leu Glu Gly Asn Gly Val Ala Thr Asp Val Pro
 65                  70                  75                  80

Ser Ala Thr Lys Arg Trp Gly Phe Arg Ser Gly Val Pro Pro Lys Val
                 85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
        130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Thr Ser Leu Glu Lys Phe Ala Val Lys
        290                 295                 300

Ser Cys Leu Ser Gln Leu Tyr Gln Thr Glu Pro Lys Thr Ser Val Val
305                 310                 315                 320

Arg Val Arg Arg Glu Leu Leu Pro Thr Gln Gly Pro Thr Gln Gln Leu
                325                 330                 335

Lys Thr Thr Lys Ser Trp Leu Gln Lys Ile Pro Leu Gln Trp Phe Lys
            340                 345                 350

Cys Thr Val Lys Glu Gly Lys Leu Gln Cys Arg Ile
        355                 360
```

<210> SEQ ID NO 19
<211> LENGTH: 128
<212> TYPE: PRT
<213> ORGANISM: homo sapiens

<400> SEQUENCE: 19

```
Asp Val Gln Leu Val Glu Ser Gly Gly Gly Val Val Gln Pro Gly Gly
 1               5                  10                  15

Ser Leu Lys Leu Ala Cys Val Val Ser Gly Phe Arg Phe Ser Asp Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Gly Lys Tyr Tyr Val Asp Ser Val
        50                  55                  60
```

```
Lys Gly Arg Phe Thr Val Ser Arg Asp Asn Ala Lys Asn Ser Leu Tyr
 65                  70                  75                  80

Leu His Met Thr Ser Leu Gly Ala Glu Asp Thr Ala Val Tyr Phe Cys
                     85                  90                  95

Ala Arg Ala Ala Pro Thr Gly Ser Tyr Thr Asn Ile Leu Val Asp Asn
                100                 105                 110

Val His Phe Asp Tyr Trp Gly Gln Gly Ile Leu Val Ala Val Ser Ser
            115                 120                 125

<210> SEQ ID NO 20
<211> LENGTH: 107
<212> TYPE: PRT
<213> ORGANISM: homo sapiens

<400> SEQUENCE: 20

Gly Ile Gln Leu Thr Gln Ser Pro Gly Ser Leu Ser Ala Ser Val Gly
  1               5                  10                  15

Asp Ser Val Thr Ile Thr Cys Arg Pro Asn Gln Asn Ile Ala Thr Tyr
                 20                  25                  30

Ile Asn Trp Tyr Gln Gln Thr Pro Gly Lys Ala Pro Lys Leu Leu Ile
             35                  40                  45

Tyr Ala Ala Ser Ile Leu Gln Ser Gly Val Pro Ser Arg Phe Ser Gly
 50                  55                  60

Ala Gly Ser Gly Thr His Phe Thr Leu Ile Ile Ser Thr Leu Gln Pro
 65                  70                  75                  80

Glu Asp Ser Ala Thr Tyr Tyr Cys Gln Gln Ser Tyr Ser Thr Pro Trp
                 85                  90                  95

Thr Phe Gly Gln Gly Thr Lys Val Glu Ile Lys
                100                 105

<210> SEQ ID NO 21
<211> LENGTH: 385
<212> TYPE: DNA
<213> ORGANISM: homo sapiens

<400> SEQUENCE: 21
gatgtgcagt tggtggagtc tgggggaggc gtggtccagc cggggggtc cctgaaactc      60 gcctgtgtag tctctggatt caggtttagt gactactgga tgagttgggt ccgccaggcc   120
ccagggaagg ggctggaatg ggtggccaac ataaaacaag atggaagtgg aagtactat    180 gtggactccg tgaagggccg attcaccgtc tccagagaca acgccaagaa ctcactgtat   240
ctacacatga ccagcctggg agccgaggac acggccgtat acttctgcgc gagagcagcc   300
cccaccggct cctacactaa tatcctagtc gacaacgtcc acttcgacta ctggggccag   360
ggaatcctgg tcgccgtctc ctcag                                         385

<210> SEQ ID NO 22
<211> LENGTH: 322
<212> TYPE: DNA
<213> ORGANISM: homo sapiens

<400> SEQUENCE: 22
ggcatccagc tgacccagtc tccaggctcc ctgtctgcat ctgtaggaga cagtgtcacc    60
atcacttgcc ggccaaatca gaacatcgcc acctatataa attggtatca gcagacacca   120
gggaaagccc ctaagctcct gatctatgcc gcatccattt tgcagagtgg ggtcccatca   180
aggttcagtg gcgctggatc tgggacacat ttcactctca tcatcagtac cctacaacct   240
```
gaggattctg caacttacta ctgccaacag agttacagta ccccgtggac attcggccaa        300
gggaccaaag tggaaatcaa ac                                                 322

<210> SEQ ID NO 23
<211> LENGTH: 113
<212> TYPE: PRT
<213> ORGANISM: homo sapiens

<400> SEQUENCE: 23

Ala Val Gln Leu Val Gln Ser Gly Ala Glu Val Lys Lys Pro Gly Thr
1               5                   10                  15

Thr Val Lys Ile Ser Cys Lys Val Ser Gly Tyr Thr Phe Ile Gln Glu
            20                  25                  30

Tyr Ile His Trp Val Gln Gln Ala Pro Gly Lys Gly Leu Val Trp Met
        35                  40                  45

Gly Leu Gly Asp Pro Glu Asn Asn Glu Thr Leu Tyr Ser Glu Asp Phe
    50                  55                  60

Gln Gly Arg Val Thr Met Thr Ala Asp Thr Ser Ser Asp Thr Ala Tyr
65                  70                  75                  80

Leu Glu Leu Arg Ser Leu Thr Phe Ala Asp Thr Ala Val Tyr Phe Cys
                85                  90                  95

Thr Ser Arg Lys Ser Trp Trp Gly Gln Gly Thr Leu Val Thr Val Ala
            100                 105                 110

Ser

<210> SEQ ID NO 24
<211> LENGTH: 111
<212> TYPE: PRT
<213> ORGANISM: homo sapiens

<400> SEQUENCE: 24

Glu Leu Val Leu Thr Gln Ser Pro Gly Thr Leu Ser Leu Ser Pro Gly
1               5                   10                  15

Glu Ser Ala Thr Leu Ser Cys Arg Ala Ser Gln Ser Leu Ser Ser Asp
            20                  25                  30

Ser Val Ser Trp Phe Gln Gln Lys Pro Gly Gln Ala Pro Arg Leu Val
        35                  40                  45

Ile His Gly Thr Ser Lys Arg Ala Thr Gly Ile Pro Asp Arg Phe Ser
    50                  55                  60

Gly Gly Gly Ser Gly Thr Asp Phe Thr Leu Thr Ile Ala Arg Leu Glu
65                  70                  75                  80

Pro Glu Asp Phe Ala Val Tyr Tyr Cys Gln Arg Ser Gly Tyr Gly Met
                85                  90                  95

Ser Val Thr Trp Thr Phe Gly Gln Gly Thr Thr Val Glu Ile Lys
            100                 105                 110

<210> SEQ ID NO 25
<211> LENGTH: 340
<212> TYPE: DNA
<213> ORGANISM: homo sapiens

<400> SEQUENCE: 25
gcggtccagt tggtacaatc tggggctgag gtgaagaagc tgggaccacc gtcaaaatc         60 tcctgcaaag tttctggata caccttcatt caagaataca tacactgggt gcaacaggcc       120
cctggaaaag gcttgtgtg gatgggactt ggtgaccctg aaaataatga gactctatat       180
tcagaggatt tccaaggcag agtcaccatg accgcggaca catcctcaga cacagcctat       240

```
ctggaactgc gcagcctgac atttgcagac acggccgtct atttctgtac atcacgaaag    300
tcctggtggg gccagggaac cctggtcacc gtcgcctcag                          340
```

<210> SEQ ID NO 26
<211> LENGTH: 334
<212> TYPE: DNA
<213> ORGANISM: homo sapiens

<400> SEQUENCE: 26

```
gaacttgtgt tgacgcagtc tccaggcacc ctgtctttgt ctccagggga aagcgccacc    60
ctctcctgta gggccagtca gagtcttagc agcgactctg tatcttggtt ccagcagaaa   120
cctggccagg ctcccaggct cgtcatccat ggtacatcaa agagggccac tggcatccca   180
gacaggttca gtggcggtgg gtctgggaca gacttcactc tcaccatcgc cagactggag   240
cctgaggatt ttgcagtcta ttattgtcag cggtctgggt atggtatgtc agtcacgtgg   300
acgttcggcc aagggaccac ggtggagatc aaac                               334
```

<210> SEQ ID NO 27
<211> LENGTH: 334
<212> TYPE: DNA
<213> ORGANISM: homo sapiens

<400> SEQUENCE: 27

```
gaacttgtgt tgacgcagtc tccaggcacc ctgtctttgt ctccagggga aagcgccacc    60
ctctcctgta gggccagtca gagtcttagc agcgactctg tatcttggtt ccagcagaaa   120
cctggccagg ctcccaggct cgtcatccat ggtacatcaa agagggccac tggcatccca   180
gacaggttca gtggcggtgg gtctgggaca gacttcactc tcaccatcgc cagactggag   240
cctgaggatt ttgcagtcta ttattgtcag cggtctgggt atggtatgtc agtcacgtgg   300
acgtttggcc aagggaccac ggtggagatc aaac                               334
```

<210> SEQ ID NO 28
<211> LENGTH: 119
<212> TYPE: PRT
<213> ORGANISM: homo sapiens

<400> SEQUENCE: 28

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ala Leu Arg Ser Tyr
            20                  25                  30

Asp Met His Trp Val Arg Gln Thr Ile Asp Lys Arg Leu Glu Trp Val
        35                  40                  45

Ser Ala Val Gly Pro Ser Gly Asp Thr Tyr Ala Asp Ser Val Lys
    50                  55                  60

Gly Arg Phe Ala Val Ser Arg Glu Asn Ala Lys Asn Ser Leu Ser Leu
65                  70                  75                  80

Gln Met Asn Ser Leu Thr Ala Gly Asp Thr Ala Ile Tyr Tyr Cys Val
                85                  90                  95

Arg Ser Asp Arg Gly Val Ala Gly Leu Phe Asp Ser Trp Gly Gln Gly
            100                 105                 110

Ile Leu Val Thr Val Ser Ser
        115

<210> SEQ ID NO 29

```
<211> LENGTH: 106
<212> TYPE: PRT
<213> ORGANISM: homo sapiens

<400> SEQUENCE: 29

Asp Ile Gln Met Thr Gln Ser Pro Ser Leu Ser Ala Ser Val Gly
1               5                   10                  15

Asp Arg Ile Thr Ile Thr Cys Arg Ala Ser Gln Ala Phe Ser Asn Tyr
            20                  25                  30

Val Ala Trp Tyr Gln Gln Arg Pro Gly Lys Val Pro Lys Leu Leu Ile
        35                  40                  45

Ser Ala Ala Ser Ala Leu His Ala Gly Val Pro Ser Arg Phe Ser Gly
50                  55                  60

Ser Gly Ser Gly Thr His Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Leu
                85                  90                  95

Thr Phe Gly Gly Gly Thr Lys Val Glu Ile
            100                 105

<210> SEQ ID NO 30
<211> LENGTH: 357
<212> TYPE: DNA
<213> ORGANISM: homo sapiens

<400> SEQUENCE: 30
gaagtgcagc tggtggagtc tggaggaggt ctgattcagc cgggggttc cctgcgtctg       60 agttgtgccg catctggatt tgctctgcga agctacgaca tgcactgggt gagacagact      120
atcgataagc gcctggagtg ggtgtctgct gtcggcccca gtggagacac ctactatgca      180
gattcagtga aggggaggtt cgcagtctcc cgggaaaacg ccaaaaattc cctgagcctg      240
cagatgaact ctctgaccgc cggcgacaca gctatctact attgcgtcag gagcgataga      300
ggggtcgcag gactgtttga ttcatggggt cagggtattc tggtcaccgt gtcttca        357

<210> SEQ ID NO 31
<211> LENGTH: 318
<212> TYPE: DNA
<213> ORGANISM: homo sapiens

<400> SEQUENCE: 31
gatattcaga tgactcagag cccttcctca ctgtccgcat ccgtgggaga ccgtattact       60
attacttgta gagcttctca ggcttttttct aactacgtgg cttggtatca gcagaggccc     120
ggcaaggtcc ctaaactgct gatctccgcc gcttctgcac tgcatgctgg agtgccaagc     180
cggttctctg gaagtggatc agggactcac ttcaccctga caatttccag cctgcagccc     240
gaggatgtcg caacctacta ttgccagaac tacaacagtg ctcccctgac attcggtggt     300
ggaacaaagg tcgagatc                                                    318

<210> SEQ ID NO 32
<211> LENGTH: 8
<212> TYPE: PRT
<213> ORGANISM: homo sapiens

<400> SEQUENCE: 32

Gly Phe Ala Leu Arg Met Tyr Asp
1               5
```

```
<210> SEQ ID NO 33
<211> LENGTH: 7
<212> TYPE: PRT
<213> ORGANISM: homo sapiens

<400> SEQUENCE: 33

Val Gly Pro Ser Gly Asp Thr
1               5

<210> SEQ ID NO 34
<211> LENGTH: 13
<212> TYPE: PRT
<213> ORGANISM: homo sapiens

<400> SEQUENCE: 34

Val Arg Ser Asp Arg Gly Val Ala Gly Leu Phe Asp Ser
1               5                   10

<210> SEQ ID NO 35
<211> LENGTH: 6
<212> TYPE: PRT
<213> ORGANISM: homo sapiens

<400> SEQUENCE: 35

Gln Ala Phe Asp Asn Tyr
1               5

<210> SEQ ID NO 36
<211> LENGTH: 3
<212> TYPE: PRT
<213> ORGANISM: homo sapiens

<400> SEQUENCE: 36

Ala Ala Ser
1

<210> SEQ ID NO 37
<211> LENGTH: 9
<212> TYPE: PRT
<213> ORGANISM: homo sapiens

<400> SEQUENCE: 37

Gln Asn Tyr Asn Ser Ala Pro Leu Thr
1               5

<210> SEQ ID NO 38
<211> LENGTH: 8
<212> TYPE: PRT
<213> ORGANISM: homo sapiens

<400> SEQUENCE: 38

Gly Phe Ala Leu Arg Ser Tyr Asp
1               5

<210> SEQ ID NO 39
<211> LENGTH: 6
<212> TYPE: PRT
<213> ORGANISM: homo sapiens

<400> SEQUENCE: 39

Gln Ala Phe Ser Asn Tyr
1               5

<210> SEQ ID NO 40
<211> LENGTH: 8
```

```
<212> TYPE: PRT
<213> ORGANISM: homo sapiens

<400> SEQUENCE: 40

Gly Gly Ser Leu Ser Ser Phe Tyr
1               5

<210> SEQ ID NO 41
<211> LENGTH: 7
<212> TYPE: PRT
<213> ORGANISM: homo sapiens

<400> SEQUENCE: 41

Ile Tyr Tyr Ser Gly Ser Pro
1               5

<210> SEQ ID NO 42
<211> LENGTH: 19
<212> TYPE: PRT
<213> ORGANISM: homo sapiens

<400> SEQUENCE: 42

Val Arg Ala Ser Arg Ser Tyr Tyr Trp Gly Ser Tyr Arg Pro Thr Ala
1               5                   10                  15

Phe Asp Ser

<210> SEQ ID NO 43
<211> LENGTH: 6
<212> TYPE: PRT
<213> ORGANISM: homo sapiens

<400> SEQUENCE: 43

Asn Leu Gly Asp Lys Tyr
1               5

<210> SEQ ID NO 44
<211> LENGTH: 3
<212> TYPE: PRT
<213> ORGANISM: homo sapiens

<400> SEQUENCE: 44

Gln Asp Asn
1

<210> SEQ ID NO 45
<211> LENGTH: 8
<212> TYPE: PRT
<213> ORGANISM: homo sapiens

<400> SEQUENCE: 45

Gln Thr Trp Asp Ser Thr Val Val
1               5

<210> SEQ ID NO 46
<211> LENGTH: 8
<212> TYPE: PRT
<213> ORGANISM: homo sapiens

<400> SEQUENCE: 46

Gly Phe Arg Phe Ser Asp Tyr Trp
1               5

<210> SEQ ID NO 47
<211> LENGTH: 8
```

<212> TYPE: PRT
<213> ORGANISM: homo sapiens

<400> SEQUENCE: 47

Ile Lys Gln Asp Gly Ser Gly Lys
1               5

<210> SEQ ID NO 48
<211> LENGTH: 21
<212> TYPE: PRT
<213> ORGANISM: homo sapiens

<400> SEQUENCE: 48

Ala Arg Ala Ala Pro Thr Gly Ser Tyr Thr Asn Ile Leu Val Asp Asn
1               5                   10                  15

Val His Phe Asp Tyr
            20

<210> SEQ ID NO 49
<211> LENGTH: 6
<212> TYPE: PRT
<213> ORGANISM: homo sapiens

<400> SEQUENCE: 49

Gln Asn Ile Ala Thr Tyr
1               5

<210> SEQ ID NO 50
<211> LENGTH: 9
<212> TYPE: PRT
<213> ORGANISM: homo sapiens

<400> SEQUENCE: 50

Gln Gln Ser Tyr Ser Thr Pro Trp Thr
1               5

<210> SEQ ID NO 51
<211> LENGTH: 8
<212> TYPE: PRT
<213> ORGANISM: homo sapiens

<400> SEQUENCE: 51

Gly Gly Thr Leu Ser Asn Tyr Ala
1               5

<210> SEQ ID NO 52
<211> LENGTH: 8
<212> TYPE: PRT
<213> ORGANISM: homo sapiens

<400> SEQUENCE: 52

Thr Ile Pro Thr Leu Gly Met Ser
1               5

<210> SEQ ID NO 53
<211> LENGTH: 16
<212> TYPE: PRT
<213> ORGANISM: homo sapiens

<400> SEQUENCE: 53

Ala Thr Met Gly Ser Ala Asp Thr Ser Phe Tyr Phe Tyr Met Asp Val
1               5                   10                  15

<210> SEQ ID NO 54

```
<211> LENGTH: 7
<212> TYPE: PRT
<213> ORGANISM: homo sapiens

<400> SEQUENCE: 54

Gln Ser Val Ser Ser Ser Tyr
1               5

<210> SEQ ID NO 55
<211> LENGTH: 3
<212> TYPE: PRT
<213> ORGANISM: homo sapiens

<400> SEQUENCE: 55

Gly Thr Ser
1

<210> SEQ ID NO 56
<211> LENGTH: 9
<212> TYPE: PRT
<213> ORGANISM: homo sapiens

<400> SEQUENCE: 56

Gln Gln Tyr Ala Tyr Ser Pro Phe Thr
1               5

<210> SEQ ID NO 57
<211> LENGTH: 8
<212> TYPE: PRT
<213> ORGANISM: homo sapiens

<400> SEQUENCE: 57

Gly Tyr Thr Phe Ile Gln Glu Tyr
1               5

<210> SEQ ID NO 58
<211> LENGTH: 8
<212> TYPE: PRT
<213> ORGANISM: homo sapiens

<400> SEQUENCE: 58

Gly Asp Pro Glu Asn Asn Glu Thr
1               5

<210> SEQ ID NO 59
<211> LENGTH: 6
<212> TYPE: PRT
<213> ORGANISM: homo sapiens

<400> SEQUENCE: 59

Thr Ser Arg Lys Ser Trp
1               5

<210> SEQ ID NO 60
<211> LENGTH: 7
<212> TYPE: PRT
<213> ORGANISM: homo sapiens

<400> SEQUENCE: 60

Gln Ser Leu Ser Ser Asp Ser
1               5

<210> SEQ ID NO 61
<211> LENGTH: 12
<212> TYPE: PRT
```

<213> ORGANISM: homo sapiens

<400> SEQUENCE: 61

Gln Arg Ser Gly Tyr Gly Met Ser Val Thr Trp Thr
1               5                   10

<210> SEQ ID NO 62
<211> LENGTH: 108
<212> TYPE: PRT
<213> ORGANISM: homo sapiens

<400> SEQUENCE: 62

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Thr Ser Ser Arg Ala Thr Gly Ile Pro Asp Arg Phe Ser
50                  55                  60

Gly Ser Ala Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Tyr Ser Pro
                85                  90                  95

Phe Thr Phe Gly Pro Gly Thr Thr Val Asp Ile Lys
            100                 105

<210> SEQ ID NO 63
<211> LENGTH: 23
<212> TYPE: DNA
<213> ORGANISM: Artificial sequence
<220> FEATURE:
<223> OTHER INFORMATION: DNA primer

<400> SEQUENCE: 63
ttttcaatcc tcaaccgtaa ggc                                       23

<210> SEQ ID NO 64
<211> LENGTH: 20
<212> TYPE: DNA
<213> ORGANISM: Artificial sequence
<220> FEATURE:
<223> OTHER INFORMATION: DNA primer

<400> SEQUENCE: 64
cagtccggtc ccagaatgtg                                           20

<210> SEQ ID NO 65
<211> LENGTH: 21
<212> TYPE: DNA
<213> ORGANISM: Artificial sequence
<220> FEATURE:
<223> OTHER INFORMATION: DNA primer

<400> SEQUENCE: 65
catgtgccgc cccatcgctg c                                         21

<210> SEQ ID NO 66
<211> LENGTH: 58
<212> TYPE: PRT
<213> ORGANISM: Artificial sequence
<220> FEATURE:
<223> OTHER INFORMATION: Modified Ebola virus GP

```
<400> SEQUENCE: 66

Met Lys Gln Ile Glu Asp Lys Ile Glu Ile Leu Ser Lys Ile Tyr
1               5                   10                  15

His Ile Glu Asn Glu Ile Ala Arg Ile Lys Lys Leu Ile Gly Glu Val
                20                  25                  30

Ala Ser Ser Ser Ile Glu Gly Arg Gly Ser His His His His His His
                35                  40                  45

Ser Ala Trp Ser His Pro Gln Phe Glu Lys
    50                  55
```